US008637237B2

(12) United States Patent
Henrich et al.

(10) Patent No.: US 8,637,237 B2
(45) Date of Patent: Jan. 28, 2014

(54) METHODS, COMPOSITIONS, AND SYSTEMS FOR THE IDENTIFICATION OF SPECIES-SPECIFIC OR DEVELOPMENTAL STAGE-SPECIFIC INSECTICIDES

(75) Inventors: Vincent C. Henrich, Greensboro, NC (US); Cary Alan Weinberger, Carrboro, NC (US)

(73) Assignee: The University of North Carolina at Greensboro, Greensboro, NC (US)

( * ) Notice: Subject to any disclaimer, the term of this patent is extended or adjusted under 35 U.S.C. 154(b) by 1553 days.

(21) Appl. No.: 11/543,682

(22) Filed: Oct. 5, 2006

(65) Prior Publication Data
US 2008/0020381 A1 Jan. 24, 2008

Related U.S. Application Data

(63) Continuation-in-part of application No. 10/929,090, filed on Aug. 27, 2004, now Pat. No. 7,790,377.

(60) Provisional application No. 60/723,724, filed on Oct. 5, 2005, provisional application No. 60/498,847, filed on Aug. 29, 2003.

(51) Int. Cl.
*C12Q 1/68* (2006.01)
*C12N 15/63* (2006.01)
*C07H 21/04* (2006.01)
*C12N 5/00* (2006.01)

(52) U.S. Cl.
USPC ............................. 435/6.1; 435/455; 536/23.4

(58) Field of Classification Search
None
See application file for complete search history.

(56) References Cited

U.S. PATENT DOCUMENTS

| | | | |
|---|---|---|---|
| 5,849,320 A | 12/1998 | Turnblad et al. | |
| 5,891,431 A | 4/1999 | Palli et al. | |
| 5,942,542 A | 8/1999 | Killick et al. | |
| 6,063,610 A * | 5/2000 | Silver et al. | 435/197 |
| 6,265,173 B1 | 7/2001 | Evans et al. | |
| 6,326,165 B1 | 12/2001 | Wilson et al. | |
| 6,333,318 B1 | 12/2001 | Evans et al. | |
| 6,362,394 B1 | 3/2002 | Crossland et al. | |
| 6,586,470 B1 | 7/2003 | Lojek et al. | |
| 6,603,044 B1 | 8/2003 | Tohnishi et al. | |
| 6,617,341 B1 | 9/2003 | Iwataki et al. | |
| 6,630,465 B2 | 10/2003 | Treacy et al. | |
| 6,737,382 B1 | 5/2004 | Iwataki et al. | |
| 6,737,383 B1 | 5/2004 | Annis et al. | |
| 7,790,377 B2 | 9/2010 | Henrich et al. | |
| 2003/0211455 A1 | 11/2003 | Tran et al. | |
| 2005/0049230 A1 | 3/2005 | Henrich et al. | |

FOREIGN PATENT DOCUMENTS

| | | |
|---|---|---|
| WO | WO 91/13167 | 5/1991 |
| WO | WO-98/46724 | 10/1998 |
| WO | WO 99/36520 | 7/1999 |
| WO | WO 99/36520 A | 7/1999 |
| WO | WO 01/70816 A | 9/2001 |
| WO | WO 01/70816 A2 | 9/2001 |

OTHER PUBLICATIONS

Clayton, G. et al., The Structure of the Ultraspiracle Ligand-Binding Domain Reveals a Nuclear Receptor locked in an Inactive Conformation, Proc. Natl., Acad. Sci. USA, vol. 98, pp. 1549-1554, 2001.
Carney, G. et al., Creation of EcR Isoform-Specific Mutations in *Drosophila melanogaster* via local P Element Transposition, Imprecise P Element Excision, and Male Recombination, Mol. Genet. Genomics, vol. 271, pp. 282-290, 2004.
Oro, A. et al., The *Drosophila* Retinoid X Receptor Homolog Ultraspiracle Functions in Both Female Reproduction and Eye Morphogenesis, Development, vol. 115, pp. 449-462, 1992.
Perrimon, N. et al., Developmental Genetics of the 2C-D Region of the *Drosophila* X Chromosome, Genetics, vol. 111, pp. 23-41, 1985.
Przibilla, S. et al., Functional Studies on the Ligand-Binding Domain of Ultraspiracle from *Drosophila melanogaster*, Biol. Chem., vol. 385, pp. 21-30, 2004.
Schubiger, M. et al., Isoform Specific Control of Gene Activity In-Vivo by the *Drosophila* Ecdysone Receptor, Mech. Dev., vol. 120, pp. 909-918, 2003.
Truman, J. et al., Ecdysone Receptor Expression in the CNS Correlates with Stage-Specific Responses to Ecydsteroids during *Drosophila* and *Manduca* Development, Development, vol. 120, pp. 219-234, 1994.
Robinow, S. et al., Programmed Cell Death in the *Drosophilia* CNS is Ecdysone-Regulated and Coupled with a Specific Ecdysone Receptor Isoform, Development, vol. 119, pp. 1251-1259, 1993.
Schubiger, M. et al., The RXR Ortholog USP Suppresses Early Metamorphic Processes in *Drosophila* in the Absence of Ecdysteroids, Development, vol. 127, pp. 1151-1159, 2000.
Ghbeish, N. et al., The Dual Role of Ultraspiracle, the *Drosophila* Retinoid X Receptor, in the Ecdysone Response, PNAS, vol. 98, No. 7, pp. 3867-3872, 2001.
Ghbeish, N. et al., Analyzing the Repressive Function of Untraspiracle, the *Drosophila* RXR, in *Drosophila* Eye Development, Mechanisms of Development, vol. 111, pp. 89-98, 2002.
Needleman, S. et al., A General Method Applicable to the Search for Similarities in the Amino Acid Sequence of Two Proteins, J. Mol. Biol., vol. 48, pp. 443-453, 1970.
Bergman, T. et al., Ligand Control of Interaction In Vivo Between Ecdysteroid Receptor and Ultraspiracle Ligand-Binding Domain, Biochem. Society, vol. 378, pp. 779-784, 2004.
Grebe, M. et al., Characterization of the Ligand-Binding Domain of the Ecdysteroid Receptor from *Drosophila melanogaster*, Biol. Chem., vol. 384, pp. 105-116, 2003.

(Continued)

*Primary Examiner* — Catherine Hibbert
(74) *Attorney, Agent, or Firm* — Kilpatrick Townsend & Stockton LLP

(57) ABSTRACT

Ecdysteroid action in *Drosophila melanogaster* and other insects is mediated by the dimerization of two nuclear receptors, the ecdysone receptor (EcR) and Ultraspiracle (USP), which regulate the transcription of target genes. Disclosed are nucleic acid constructs to identify insecticides having the ability to modify insect development and growth in a developmental stage-specific and/or species-specific manner.

6 Claims, 20 Drawing Sheets

(56) References Cited

OTHER PUBLICATIONS

Characterization of *Drosophila* EcR and USP in a Mammalian Cell Culture System, National *Drosophila* Research Conference in San Diego (Mar. 30-Apr. 3, 2005).

Beatty, J. et al., Analysis of Transcriptional Activity mediated by the *Drosophila melanogaster* Ecdysone Receptor Isoforms in a Heterologous Cell Culture System, Insect Mol. Biol., vol. 15, pp. 785-795, 2006.

Wurtz, J. et al., A Canonical Structure for the Ligand-Binding Domain of Nuclear Receptors, Nature Structural Biology, vol. 3, No. 1, pp. 87-94, 1996.

Wurtz, J. et al., A Canonical Structure for the Ligand-Binding Domain of Nuclear Receptors, Nature Structural Biology, vol. 3, No. 2, pp. 206, 1996.

Billas, I. et al., Structural Adaptability in the Ligand-Binding Pocket of the Ecdysone Hormone Receptor, Nature, vol. 426, pp. 91-96, 2003.

Tobe, S. et al., Juvenile Hormone Titre and Regulation in the Cockroach *Diploperapunctata*, Experientia, vol. 41, pp. 1028-1034, 1985.

Roller, H. et al., The Chemistry and Biology of Juvenile Hormone, Recent Prog. Horm. Res., vol. 24, pp. 651-680, 1968.

NCBI Accession No. U18374, Identification of a Nuclear Receptor that is Activated by Farnesol Metabolites, Cell, vol. 81, No. 5, pp. 687-693, 1995.

Schooley, D. et al., Juvenile hormone biosynthesis. In: *Comprehensive Insect Physiology, Biochemistry, and Pharmacology* Edited by GA Kerkut, LI Gilbert, vol. 7. pp. 363-389. Oxford: Pergamon Press; 1985: 363-389.

Crowell, P. et al., Chemoprevention and Therapy of Cancer by d-Limonene, Critical Reviews in Oncogenesis, vol. 5, No. 1, pp. 1-22, 1994.

Machicao, F. et al., Mechanism of the Stimulation of RNA Synthesis in Rat Liver Nuclei by Silybin, Hoppe-Seyler's Z Physiol. Chem., vol. 358, pp. 141-147, 1977.

Krecman, V. et al., Silymarin Inhibits the Development of Diet-Induced Hypercholersterolemia in Rats, Planta Med., vol. 64, pp. 138-142, 1998.

Bowers, W., Toxicology of the Precocenes. In: *Insecticide Mode of Action* Edited by JR Coats. New York: Academic Press; 1982.

Isoform and Interspecies Comparision of Ecdysteroid Receptor in a Cell Culture System, XVI International Ecdysone Workshop, Jul. 13, 2006, Ghent, Belgium.

The Drosophilia Ecdysteroid Receptor: Not a Trigger for Developmental Processes, Endocrinology Workshop, Oct. 6, 2005, University of Ulm, Germany.

Olson, R., Biosynthesis of Ubiquinones in Animals, Vitam. Horm., vol. 24, pp. 551-574, 1966.

Li, T. et al., A Conditional Rescue System reveals Essential Functions for the Ecdysone Receptor (EcR) Gene during Molting and Metamorphosis in *Drosophila*, Development, vol. 127, pp. 2897-2905, 2000.

Hu, X. et al., Transcription Activation by the Ecdysone Receptor (EcR/USP): identification of Activation Functions, Molecular Endocrinology, vol. 17, No. 4, pp. 716-731, 2003.

Gilbert, L. et al., The Juvenile Hormones: Historical Facts and Speculations on Future Research Directions, Insect Biochemistry and Molecular Biology, vol. 30, pp. 617-644, 2000.

Hall, B. et al., The RXR Homolog Ultraspiracle is an Essential Component of the *Drosophila* Ecdysone Receptor, Development, vol. 125, pp. 4709-4717, 1998.

Riddiford, L. et al., Ecdysone Receptors and Their Biological Actions, Vitamins and Hormones, vol. 60, pp. 1-73, 2000.

Sung, C. et al., Characterization of the Regulatory Elements Controlling Neuronal Expression of the A-Isoform of the Ecdysone Recepor Gene of *Drosophila melanogaster*, Mechanisms of Development, vol. 91, pp. 237-248, 2000.

Schubiger, M. et al., *Drosophila* EcR-B Ecdysone Receptor Isoforms are Required for Larval Molting and for Neuron Remodeling during Metamorphosis, Development, vol. 125, pp. 2053-2062, 1998.

Antoniewski, C. et al., Structural Features Critical to the Activity of an Ecdysone Receptor Binding Site, Insect Biochem. Mol. Biol., vol. 23, pp. 105-114, 1993.

Bowers, W. et al., Discovery of Insect Anti-Juvenile Hormones in Plants, Science, vol. 193, pp. 542-547, 1976.

Office Action mailed Jul. 24, 2008 for U.S. Appl. No. 10/929,090.

Office Action mailed Feb. 14, 2008 for U.S. Appl. No. 10/929,090.

Office Action mailed Dec. 5, 2008 for U.S. Appl. No. 10/929,090.

Agric, University of Missouri, Plant Sciences,( Award Type—HATCH .c H), "Characterization of the Upstream Regulator(s) of S6 Kinase and of Ecdysone Receptor Complex (citation)." Printed Aug. 12, 2003.

Allgood, V. et al., "Modulation by Vitamin $B_6$ of Glucocorticoid Receptor-Mediated Gene Expression Requires Transcription Factors in Addition to the Glucocorticoid Receptor." J. Biol. Chem., 1993, vol. 268, No. 28, 20870-20876.

Arbeitman, et al., "Molecular Chaperones Activate the *Drosophila* Ecdysone Receptor, an RXR Heterodimer." Cell, vol. 101, No. 1, pp. 67-77, 2000.

Bak, A. et al., "The Effect of Serum Cholesterol Levels of Coffee Brewed by Filtering and Boiling." N. Engl. J. Med., 1989, vol. 321, No. 21, 1432-1437.

Baker, K. et al., "Transcriptional Activation of the *Drosophila* Ecdysone Receptor by Insect and Plant Ecdysteroids." Insect Biochem. Mol. Biol., 2000, 30:1037-1043.

Baker, K. et al., "The *Drosophila* Orphan Nuclear Receptor DHR38 Mediates an Atypical Ecdysteroid Signaling Pathway." Cell, 2003, 113:731-742.

Bender, M. et al. "*Drosophila* Ecdysone Receptor Mutations Reveal Functional Differences among Receptor Isoforms." Cell, 1997, 91:777-788.

Biggers, W. et al., "Detection of Juvenile Hormone-Active Compounds by Larvae of the Marine Annelid *Capitella* Sp. I." Arch. of Insect Biochem. Physiol., 1996, 32:475-484.

Birkett, M. et al., "New Roles for Cis-Jasmone as an Insect Semiochemical and in Plant Defense." Proc. Natl. Acad. Sci. USA, 2000, vol. 97, No. 16, 9329-9334.

Bonning, B. et al., "Development of a Recombinant Baculovirus Expressing a Modified Juvenile Hormone Esterase with Potential for Insect Control." Arch. Insect Biochem. and Physiol., 1995, 30:177-194.

Bowers, W., "Juvenile Hormone: Activity of Natural and Synthetic Synergists." Science, 1968, vol. 161, No. 3844, 895-897.

Bowers, W., "Juvenile Hormone: Activity of Aromatic Terpenoid Ethers." Science, 1969, vol. 164, No. 3877, 323-325.

Bowers, W. et al., "Juvenile Hormone: Identification of an Active Compound from Balsam Fir." Science, 1966, vol. 154, No. 3752, 1020-1021.

Bowers, W. et al., "Juvocimenes: Potent Juvenile Hormone Mimics from Sweet Basil." Science, 1980, vol. 209, No. 4460, 1030-1032.

Bowers, W. et al., "Discovery of Insect Anti-Juvenile Hormones in Plants". Science, 1976, vol. 193, No. 4253, 542-547.

Bowers, W. et. al., "Natural and Synthetic Allatotoxins: Suicide Substrates for Juvenile Hormone Biosynthesis." Science, 1982, vol. 217, No. 4560, 647-648.

Brooks, G. et al., "The Action of Precocenes in Milkweed Bugs (*Oncopeltus fasciatus*) and Locusts (*Locusta migratoria*)." Nature, 1979, 281:570-572.

Bruenger, E. et al., "Determination of Isopentenyl Diphosphate and Farnesyl Diphosphate in Tissue Samples with a Comment on Secondary Regulation of Polyisoprenoid Biosynthesis." Anal. Biochem., 1988, 173:321-327.

Buckingham, S. et al., "Imidacloprid Actions on Insect Neuronal Acetylcholine Receptors." J. Exp. Biol., 1997, 200:2685-2692.

Burke, Y. et al., "Inhibition of Pancreatic Cancer Growth by the Dietary Isoprenoids Farnesol and Geraniol." Lipids, 1997, vol. 32, No. 2, 151-156.

Carchman, R. et al., "The Inhibition of DNA Synthesis by Cannabinoids." Cancer Res., 1976, 36:95-100.

Carney, G. et al., "The *Drosophila* Ecdysone Receptor (EcR) Gene is Required Maternally for Normal Oogenesis." Genetics, 2000, 154:1203-1211.

(56) References Cited

OTHER PUBLICATIONS

Carlisle, D. et al., "Insect Hormones: Olive Oil is not an Inert Vehicle for Hormone Injection into Locusts." Science, 1968, vol. 162, No. 3860, 1393-1394.
Carlson, G. et al., "The Chemical and Biological Properties of Methoxyfenozide, A New Insecticidal Ecdysteroid Agonist." Pest Manag. Sci., 2001, 57:115-119.
Case, G. et al., "Induction of Geranyl Pyrophosphate Pyrophosphatase Activity by Cholesterol-Suppressive Isoprenoids." Lipids, 1995, vol. 30, No. 4, 357-359.
Chance, B. et al., "Inhibition of Electron and Energy Transfer in Mitochondria. Effects of Amytal, Thiopental, Rotenone, Progesterone, and Methylene Glycol." J. Biol. Chem., 1963, vol. 278, No. 1, 418-431.
Chen, J. et al. "Molecular Cloning and Induction of Nuclear Receptors from Insect Cell Lines." Insect Biochem. Mol. Biol., 2002, 32:657-667.
Cherbas, L. et al., "Effects of Juvenile Hormone on the Ecdysone Response in *Drosophila* Kc Cells." Dev. Genet., 1989, 10:177-188.
Cherbas, L. et al., "EcR Isoforms in *Drosophila*: Testing Tissue-Specific Requirements by Targeted Blockade and Rescue." Development, 2003, 130:271-284.
Chiang, J. et al., "Farnesoid X Receptor Responds to Bile Acids and Represses Cholesterol 7 α-Hydroxylase Gene (CYP7A1) Transcription." J. Biol Chem., 2000, vol. 275, No. 15, 10918-10924.
Chihara, C. et al., "Effects and Interactions of Juvenile Hormone and β-Ecdysone on *Drosophila* Imaginal Discs Cultured In Vitro." Dev. Biol., 1973, 35:36-46.
Christophe, J. et al., "Studies on the Biosynthesis of Cholesterol. XIV. The Origin of Prenoic Acids from Allyl Pyrophosphates in Liver Enzyme Systems." J. Lipid Res., 1961, vol. 2, No. 3, 244-257.
Christopherson, K. et al., "Ecdysteroid-Dependent Regulation of Genes in Mammalian Cells by a *Drosophila* Ecdysone Receptor and Chimeric Transactivators." Proc. Natl. Acad. Sci. USA, 1992, 89:6314-6318.
Dai, J. et al., "Metamorphosis of the Corpus Allatum and Degeneration of the Prothoracic Glands during the Larval-Pupal-Adult Transformation of *Drosophila melanogaster*: A Cytophysiological Analysis of the Ring Gland." Dev. Biol., 1991, 144:309-326.
Daves, G. et al., "Discovery of Ubiquinones-1, -2, -3, and -4 and the Nature of Biosynthetic Isoprenylation." Biochemistry, 1967, vol. 6, No. 9, 2861-2866.
Dela-Cruz, et al., "*Drosophila* Ecdysone Receptor Functions as a Constitutive Activator in Yeast." J. Steroid Biochem. Molec. Biol., vol. 62, No. 4, pp. 353-359, 1997.
Dinan, et al., "Cucurbitacins are Insect Steroid Hormone Antagonists acting at the Ecdysteroid Receptor." Biochemical J., vol. 327, No. 3, pp. 643-650, 1997.
Dubrovsky, E. et al. "Juvenile Hormone Signaling During Oogenesis in *Drosophila melanogaster*." Insect Biochem. Mol. Biol., 2002, 32:1555-1565.
Elegbede, J. et al., "Inhibition of DMBA-Induced Mammary Cancer by the Monoterpene D-Limonene." Carcinogenesis, 1984, vol. 5, No. 5, 661-664.
Elekonich, M. et al., "Juvenile Hormone Levels in Honey Bee (*Apis mellifera* L.) Foragers: Foraging Experience and Diurnal Variation." J. Insect Physiol., 2001, 47:1119-1125.
Farkas, R. et al., "Ecdysone-Modulated Response of *Drosophila* Cytosolic Malate Dehydrogenase to Juvenile Hormone." Arch. Insect Biochem. Physiol., 1997, 35:71-83.
Forman, B. et al., "Identification of a Nuclear Receptor that is Activated by Farnesol Metabolites." Cell, 1995, 81:687-695.
Fukami, J. et al., "Metabolism of Rotenone In Vitro by Tissue Homogenates from Mammals and Insects." Science, 1967, vol. 155, No. 3763, 713-716.
Goldstein, J. et al., "Regulation of the Mevalonate Pathway." Nature, 1990, 343:425-430.
Giguere, V. et al., "Identification of a Receptor for the Morphogen Retinoic Acid." Nature, 1987, 330:624-629.

Grober, et al., "Identification of a Bile Acid-responsive Element in the Human Ileal Bile Acid-Binding Protein Gene: Involvement of the Farnesoid X Receptor/9-cis-Retinoic Acid Receptor Heterodimer." J. Biol. Chem., 1999, vol. 274, No. 42, 29749-29754.
Guzelian, P. et al., "Drug Metabolism in Adult Rat Hepatocytes in Primary Monolayer Culture." Gastroenterology, 1977, 72:1232-1239.
Hall, B. et al., "Nuclear Receptors and the Hormonal Regulation of *Drosophila* Metamorphosis." Amer. Zoologist, 1999, 39:714-721.
Haller, H. et al., "The Synergisict Action of Sesamin with Pyrethrum Insecticides." J. Org. Chem., 1942, 7:183-184.
Hanley, K. et al., "Activators of the Nuclear Hormone Receptors PPARα and FXR Accelerate the Development of the Fetal Epidermal Permeability Barrier." J. Clin. Invest., 1997, vol. 100, No. 3, 705-712.
Harmon, M. et al., "Activation of Mammalian Retonid X Receptors by the Insect Growth Regulator Methoprene." Proc. Natl. Acad. Sci. USA, 1995, vol. 92, No. 13, 6157-6160.
He, L. et al., "Isoprenoids Suppress the Growth of Murine B16 Melanomas In Vitro and In Vivo." J. Nutr., 1997, 127:668-674.
Henrich, V. et al., "Expression and Function of the Ultraspiracle (usp) Gene during Development of *Drosophila melanogaster*." Dev. Biol., 1994, 165:38-52.
Henrich, V. et al. "Effect of FXR Activators on Ecdysteroid Receptor Activity (abstract)." Proceedings of the International Ecdysone Workshop 2000, Rapperswil, Switzerland.
Henrich, et al., "Juvenile Hormone Potentiates Ecdysone Receptor-Dependent Transcription in a Mammalian Cell Culture System." Insect Biochemistry and Molecular Biology, vol. 33, No. 12, pp. 1239-1247, 2003.
Henrich, V. "Strategies for Identifying Molecular Targets to Insect Ecdysteroid Receptors (Abstract)." Agric, University of North Carolina, Biology (Award Type—NRI Competitive Grant .c C), printed Aug. 12, 2003.
Henrick, C. et al., "Alkyl 3,7,11-Trimethyl-2,4-Dodecadienoates, A New Class of Potent Insect Growth Regulators with Juvenile Hormone Activity." J. Agr. Food Chem., 1973, vol. 21, No. 3, 354-359.
Hiruma, K. et al., "Juvenile Hormone Modulates 20-Hydroxyecdysone-Inducible Ecdysone Receptor and Ultraspiracle Gene Expression in the Tobacco Hornworm, *Manduca sexta*." Dev. Genes Evol., 1999, 209:18-30.
Hosie, A. et al., "Actions of the Insecticide Fipronil, on Dieldrin-Sensative and- Resistant GABA Receptors of *Drosophila melanogaster*." Br. J. Pharmacol., 1995, 115:909-912.
Howard, W. et al., "Catabolites of Cholesterol Synthesis Pathways and Forskolin as Activators of the Farnesoid X-Activated Nuclear Receptor." Tox. Appl. Pharm., 2000, 163:195-202.
Huang, M. et al., "Inhibition of Skin Tumorigenesis by Rosemary and its Constituents Carnosol and Ursolic Acid." Cancer Res., 1994, 54:701-708.
Jacobson, M. et al., "Naturally Occurring Insect Growth Regulators. III. Echinolone, a Highly Active Juvenile Hormone Mimic from *Echinacea angustifolia* Roots." Lloydia, 1975, vol. 38, No. 6, 473-476.
Jarvis, D. et al., "Construction and Characterization of Immediate Early Baculovirus Pesticides." Biol. Control, 1996, 7:228-235.
Johnson, J. et al., "Two-Year Toxicity and Carcinogencity Study of Methyleugenol in F344/N Rats and B6C3F, Mice." J. Agric. Food Chem., 2000, 48:3620-3632.
Jones, G. et al., "Ultraspiracle: An Invertebrate Nuclear Receptor for Juvenile Hormones." Proc. Natl. Acad. Sci. USA, 1997, vol. 94, No. 25, 13499-13503.
Jones, G. et al., "Juvenile Hormone III-Dependent Conformational Changes of the Nuclear Receptor Ultraspiracle." Insect Biochem. Mol. Biol., 2001, 32:33-49.
Katiyar, S. et al., "Protective Effects of Silymarin against Photocarcinogenesis in a Mouse Skin Model." J. Natl. Cancer Inst., 1997, vol. 89, No. 8, 556-566.
Kitareewan, S. et al., "Phytol Metabolites are Circulating Dietary Factors that Activate the Nuclear Receptor RXR." Mol. Biol. Cell, 1996, 7:1153-1166.
Koelle, M. et al., "The *Drosophila* EcR Gene Encodes an Ecdysone Receptor, A New Member of the Steroid Receptor Superfamily." Cell, 1991, 67:59-77.

(56) References Cited

OTHER PUBLICATIONS

Kumar, R. et al., "The Structure of the Nuclear Hormone Receptors." Steroids, 1999, 64:310-9.

Kunkel, et al., "Rapid and Efficient Site-Specific Mutagenesis without Phenotypic Selection." Proc. Natl. Acad. Sci. USA, 1985, vol. 82, No. 2, 488-492.

Law, J. et al., "Synthesis of a Material with High Juvenile Hormone Activity." Proc. Natl. Acad. Sci. USA, 1966, vol. 55, No. 3, 576-578.

Lefebvre, P. et al., "Two Regions of the Mouse Mammary Tumor Virus Long Terminal Repeat Regulate the Activity of its Promoter in Mammary Cell Lines." Mol. Cell Biol., 1991, vol. 11, No. 5, 2529-2537.

Lezzi, M. et al., "The Ecdysone Receptor Puzzle." Archives of Insect Biochem. and Physiol., 1999, 41:99-106.

Li, S. et al. -"Developmental Changes in the Ability to Synthesize Juvenile Hormone In Vitro by Corpora Allata from the Eri Silkworm, Samia Cynthia Ricini (Lepidoptera: Saturniidae) (citation)." Euro. J. Entomol., 2002, vol. 99, No. 4, 413-419.

Louvion, J. et al., "Fusion of GAL4-VP16 to a Steroid-Binding Domain Provides a Tool for Gratuitous Induction of Galactose-Responsive Genes in Yeast." Gene, 1993, 131:129-134.

Mangelsdorf et al., "The Nuclear Receptor Superfamily: The Second Decade." Cell, 1995, 83:835-839.

Martinez, et al., "Transcriptional Activation of the Cloned *Heliothis virescens* (Lepidoptera) Ecdysone Receptor (HvEcR) by Muristerone A." Insect Biochemistry and Molecular Biology, vol. 29, No. 10, pp. 915-930, 1999.

McNamee, D., "Limonene Trial in Cancer." Lancet, 1993, 342:801.

Meyer, A. et al., "A Highly Purified Preparation of Juvenile Hormone from the Silk Moth *Hyalophora cecropia* L." Nature 1965, 206:272-275.

Miesfeld et al., "Genetic Complementation of a Glucocorticoid Receptor Deficiency by Expression of Cloned Receptor cDNA." Cell, 1986, 46:389-399.

Miller, E. et al., "Structure-Activity Studies of the Carcinogenicities in the Mouse and Rat of Some Naturally Occurring and Synthetic Alkenylbenzene Derivatives Related to Safrole and Estragole." Cancer Res., 1983, 43:1124-1134.

Minakuchi, M. et al., "Molecular Cloning and Expression Analysis of Ultraspiracle (USP) from the Rice Stem Borer *Chilo suppressalis*." Insect Biochem. Mol. Biol., 2003, 33:41-49.

Mouillet, J. et al., "Differential Control of Gene Activity by Isoforms A, B1, and B2 of the *Drosophila* Ecdysone Receptor." Eur. J. Biochem., 2001, 268:1811-1819.

Munson, A. et al., "Antineoplastic Activity of Cannabinoids." JNCI, 1975, vol. 55, No. 3, 597-602.

Nathanson, J., "Caffeine and Related Methylxanthines: Possible Naturally Occurring Pesticides." Science, 1984, vol. 226, No. 4671, 184-187.

Nishino, H. et al., "Inhibition of the Tumor-Promoting Action of 12-O-Tetradecanoylphorbol-13-Acetate by some Oleanane-Type Triterpenoid Compounds." Cancer Res., 1988, 48:5210-5215.

No, D. et al., "Ecdysone-Inducible Gene Expression in Mammalian Cells and Transgenic Mice." Proc. Natl. Acad. Sci. USA, 1996, 93:3346-3351.

Oberdorster, E. et al., "Interaction of PAHs and PCBs with Ecdysone-Dependent Gene Expression and Cell Proliferation." Tox. Appl. Pharm., 1999, 160:101-108.

Oro, A. et al., "Relationship between the Product of the *Drosophila* Ultraspiracle Locus and the Vertebrate Retinoid X Receptor." Nature, 1990, 347:298-301.

Palli, S. et al., "Improved Ecdysone Receptor Based Inducible Gene Regulation System." Eur. J. Biochem., 2003, 270:1308-1315.

Pearson et al., "Improved Tools for Biological Sequence Comparison." Proc. Natl. Acad. Sci. USA, 1988, vol. 85, No. 8, 2444-2448.

Pratt, G. et al., "Lethal Metabolism of Precocene-I to a Reactive Epoxide by Locust Corpora Allata." Nature, 1980, 284:320-323.

Ratnayake, W. et al., "Investigation of the Effect of Coffee Lipids on Serum Cholesterol in Hamsters." Food Chem. Toxicol., 1995, vol. 33, No. 3, 195-201.

Richards, G. "Sequential Gene Activation by Ecdysone in Polytene Chromosomes of *Drosophila melanogaster*." Dev. Biol., 1978, 66:32-42.

Riddiford, L. "Cellular and Molecular Actions of Juvenile Hormone I. General Considerations and Premetamorphic Actions." Adv. Insect Physiol., 1994, 24:213-274.

Riddiford, L. et al., "Regulation and Role of Nuclear Receptors during Larval Molting and Metamorphosis of Lepidoptera." Amer. Zoologist, 1999, vol. 39, No. 4, 736-746.

Riddiford, L., "Hormone Receptors and the Regulation of Insect Metamorphosis." Receptor, 1993, 3:203-209.

Riddiford, L., "Juvenile Hormone: The Status of its "Status Quo" Action." Arch. Insect Biochem. Physiol., 1996, 32:271-286.

Riddihough, G. et al., "An Ecdysone Response Element in the *Drosophila* hsp27 Promoter." EMBO J., 1987, vol. 6, No. 12, 3729-3734.

Sacklin, J. et al., "Effect of DDT on Enzymatic Oxidation and Phosphorylation." Science, 1955, vol. 122, No. 3165, 377-378.

Saez, et al., "Identification of Ligands and Coligands for the Ecdysone-Regulated Gene Switch." Proceedings of the National Academy of Sciences of the United States of America, vol. 97, No. 26, pp. 14512-14517, 2000.

Sasorith, S. et al., "Structure-Based Analysis of the Ultraspiracle Protein and Docking Studies of Putative Ligands." J. of Insect Sci., 2002, 2:1-11.

Schneiderman, H. et al., "Control of Growth and Development in Insects." Science, 1964, vol. 143, No. 3604, 325-333.

Shonouda, M. et al., "Efficacy of the Botanical Extract (MYRRA), Chemical Insecticides and their Combinations on the Cotton Leafworm, *Spodoptera littoralis* Boisd (Lepidoptera : Noctuidae)." J. Environ. Sci. Health, 2000, B35, vol. 3, 347-356.

Smagghe, G. et al., "Comparative Toxicity and Ecdysone Receptor Affinity of Non-Steroidal Ecdysone Agonists and 20-Hydroxyecdysone in *Chironomus tentans*." Insect Biochem. Mol. Biol., 2002, 32:187-192.

Smith, T. et al., "Comparison of Biosequences." Adv. Appl. Math, 1981, 2:482.

Soderlund, D. et al., "Precocene II Metabolism in Insects: Synthesis of Potential Metabolites and Identification of Initial In Vitro Biotransformation Products." J. Agric. Food Chem., 1980, 28:724-731.

Soderlund, D., "Pyrethroid-Receptor Interactions: Stereospecific Binding and Effects on Sodium Channels in Mouse Brain Preparations." Neurotoxicology, 1985, vol. 6, No. 2, 35-46.

Soderlund, D. et al., "Mechanisms of Pyrethroid Neurotoxicity: Implications for Cumulative Risk Assessment." Toxicology, 2002, 171:3-59.

Sugano, S. et al., "Identification of Intermediates in the Conversion of Cholesterol to Pregnenolone with a Reconstituted Cytochrome $P-450_{scc}$ System: Accumulation of the Intermediate Modulated by the Adrenodoxin Level." J. Biochem., 1996, 120:780-787.

Suhr, S. et al., "High Level Transactivation by a Modified Bombyx Ecdysone Receptor in Mammalian Cells without Exogenous Retinoid X Receptor." Proc. Natl. Acad. Sci. USA, 1998, vol. 95, No. 14, 7999-8004.

Sun, X. et al., "Effect of Ecdysone Agonists on Vitellogenesis and the Expression of EcR and USP in Codling Moth (*Cydia pomonella*)." Arch. Insect Biochem. Physiol., 2003, 52:115-129.

Terpstra, A. et al., "The Hypercholesterolemic Effect of Cafestol in Coffee Oil in Gerbils and Rats." J. Nutr. Biochem., 2000, 11:311-317.

Thelle, D. et al., "The Tromso Heart Study. Does Coffee Raise Serum Cholesterol?" N. Engl. J. Med., 1983, 308:1454-1457.

Theriault, A. et al., "Modulation of Hepatic Lipoprotein Synthesis and Secretion by Taxifolin, A Plant Flavonoid." J. Lipid Res., 2000, 41:1969-1979.

Thomas, H. et al., "Heterodimerization of the *Drosophila* Ecdysone Receptor with Retinoid X Receptor and Ultraspiracle." Nature,1993, 362: 471-475.

Thummel, C., "Ecdysone-Regulated Puff Genes-2000." Insect Biochem. Mol. Biol., 2002, 32, 113-120.

Unger, E. et al., "A Chimeric Ecdysone Receptor Facilitates Methoxyfenozide-Dependant Restoration of Male Fertility in Ms45 Maize." Transgenic Res., 2002, 11:455-465.

(56) References Cited

OTHER PUBLICATIONS

Urizar, N. et al., "A Natural Product that Lowers Cholesterol as an Antagonist Ligand for FXR." Science, 2002, 296:1703-1706.
Vogtli, M. et al., "High Levels Transactivation by the Ecdysone Receptor Complex at the Core Recognition Motif." Nuc. Acids Res., 1998, vol. 26, No. 10, 2407-2414.
Wachs, H. "Synergistic Insecticides." Science, 1947, vol. 105, No. 2733, 530-531.
Weinberger, C. "A Model for Farnesoid Feedback Control in the Mevalonate Pathway." TEM, 1996, vol. 7, No. 1, 1-6.
Weusten-Van Der Wouw, M. et al., "Identity of the Cholesterol-Raising Factor from Boiled Coffee and its Effects on Liver Function Enzymes." J. Lipid Res., 1994, 35:721-735.
Wigglesworth, V., "The Juvenile Hormone." Nature, 1965, 208:522-524.
Wiseman, R. et al., "Structure-Activity Studies of the Hepatocarcinogenicities of Alkenylbenzene Derivatives Related to Estragole and Safrole on Administration to Preweanling Male C57BL/6J × C3H/HeJ F1 Mice." Cancer Res., 1987, 47:2275-2283.
Wolfgang, W., "Larval Cuticular Morphogenesis in the Tobacco Hornworm, *Manduca sexta*, and its Hormonal Regulation." Dev. Biol., 1986, 113:305-316.
Wu, J. et al., "The Hypolipidemic Natural Product Guggulsterone Acts as an Antagonist of the Bile Acid Receptor." Mol. Endocrinol., 2002, vol. 16, No. 7, 1590-1597.
Wurtz, J. et al., "Structure-Based Analysis of the Ultraspiracle Protein and Docking Studies of Putative Ligands." J. of Insect. Sci. 2002, 2:1-11.
Wyatt, G. et al., "Cellular and Molecular Actions of Juvenile Hormone. II. Roles of Juvenile Hormone in Adult Insects." Adv. Insect Physiol., 1996, 26, 1-155.
Xu, Y. et al., "Activation of Transcription Through the Ligand-Binding Pocket of the Orphan Nuclear Receptor Ultraspiracle." Eur. J. Biochem., 2002, 269:6026-6036.
Yao, T. et al., "*Drosophila* Ultraspiracle Modulates Ecdysone Receptor Function Via Heterodimer Formation." Cell, 1992, 71:63-72.
Yao, T. et al., "Functional Ecdysone Receptor is the Product of EcR and Ultraspiracle Genes." Nature, 1993, 366: 476-479.
Zhou, X. et al., "Broad Specifies Pupal Development and Mediates the 'Status Quo' Action of Juvenile Hormone on the Pupal-Adult Transformation in *Drosophila* and *Manduca*." Development, 2002, 1290: 2259-2269.
Zi, X. et al., "Silibinin Decreases Prostate-Specific Antigen with Cell Growth Inhibition Via $G_1$ Arrest, Leading to Differentiation of Prostate Carcinoma Cells: Implications for Prostate Cancer Intervention." Proc. Natl. Acad. Sci. USA, 1999, vol. 96, No. 13, 7490-7495.
NCBI Sequence, Accession No. S63761, "EcR=EcR-A {EcR-A specific region, alternatively spliced}[*Drosophila melanogaster*, Genomic/mRNA, 1070 nt]." Cell 1993, 73:1323-1337.
NCBI Sequence, Accession No. S63762, "EcR=Ecdysone Receptor {5' region, EcR-B specific region}[*Drosophila melanogaster*, Genomic, 282 nt]." Cell 1993, 73:1323-1337.
NCBI Sequence, Accession No. AF045891, "*Chironomus tentans* Ultraspiracle (USP-1) mRNA, Complete Cds." Insect Biochem. Mol. Biol., 1999, 29:931-942.
NCBI Sequence, Accession No. M74078, "*Drosophila melanogaster* Ecdysone Receptor (EcR) mRNA, Complete Cds." Cell, 1991, 67:59-77.
NCBI Sequence, Accession No. RNU18374, "*Rattus norvegicus* Farnesoid X Activated Receptor mRNA, Complete Cds." Cell, 1995, 81:687-693.
Patent Cooperation Treaty, International Search Report, International Application No. PCT/US2004/028113, mailed on Mar. 7, 2005, 8 pages.
Feyereisen. R , "Juvenile Hormone Resistance: no PASaran," Proc Natl. Acad. Sci., vol. 95, pp. 2725-2726, 1998.
Meyers et al , "Estrogen Receptor Subtype-Selective Ligands: Asymmetric Synthesis and Biological Evaluation of Cis- and Trans- 5,11-Dialkyl- 5,6,11. 12-Tetrahydrochrysenes," *J. Med. Chem.*, 1999, 42: 2456-2468.

Sheng et al.(Abstract), "Developmental Changes in the Ability to Synthesize Juvenile Hormone In Vitro by Corpora Allata from the Eri Silkworm, Samia Cynthia Ricini (Lepidoplera: Saturniidae) (citation)." Euro. J. Entomol., 2002, vol. 99, No. 4, 413-419.
Office Action mailed Jul. 11, 2007 for U.S. Appl. No. 10/929,090.
Office Action mailed Apr. 24, 2007 for U.S. Appl. No. 10/929,090.
Office Action mailed Dec. 28, 2006 for U.S. Appl. No. 10/929,090.
Amendment and Response mailed to USPTO on Nov. 13, 2007 for U.S. Appl. No. 10/929,090.
Election and Response mailed to USPTO on Jun. 18, 2007 for U.S. Appl. No. 10/929,090.
Election and Response mailed to USPTO on Jan. 31, 2007 for U.S. Appl. No. 10/929,090.
Interview Summary mailed Oct. 22, 2007 for U.S. Appl. No. 10/929,090.
International Search Report and Written Opinion mailed Jul. 12, 2005 for Patent Cooperation Treaty Application Serial No. PCT/US2004/028113.
International Search Report mailed Mar. 7. 2005 for Patent Cooperation Treaty Application Serial No. PCT/US2004/028113.
Office Action dated Jun. 19, 2009 for corresponding U.S. Appl. No. 10/929,090.
Office Action dated Nov. 17, 2009 corresponding U.S. Appl. No. 10/929,090.
Office Action dated Mar. 9, 2009 corresponding to U.S. Appl. No. 10/929,090.
Henrich, V. et al., "A steroid/thyroid hormone receptor superfamily member in *Drosophila melanogaster* that shares extensive sequence similarity with a mammalian homologue," Nucleic Acids Research, 1990, 18:4143-4148.
Talbot, W. et al., "*Drosophila* Tissues with Different Metamorphic Responses to Ecdysone Express Different Ecdysone Receptor Isoforms," Cell, 1993, 73:1323-1337.
Zhang, Y. et al., "Natural Structural Variants of the Nuclear Receptor Farnesoid X Receptor Affect Transcriptional Activation," Biol. Chem., 2003, 278:104-110.
Wisconsin Genetics Software Package Release 7.0, Genetics Computer Group, 575 Science Drive, Madison, WI (1982).
Alyokhin, A. et al., "Resistance and cross-resistance to imidacloprid and thiamethoxam in the Colorado potato beetle *Leptinotarsa decemlineata*," 2007, Pest Management, 63:32-41.
Azoitei, A. and Spindler-Barth, M., "DNA affects ligand binding of the ecdysone receptor of *Drosophila melanogaster*," 2009, Mol. Cell. Endocrinol., 303:91-99.
Billas, I. and Moras, D., "Ligand-Binding Pocket of the Ecdysone Receptor," 2005, Vitam. Horm., 73:101-129.
Braun, S. et al., "DNA-Binding Properties of *Drosophila* Ecdysone Receptor Isoforms and Their Modification by the Heterodimerization Partner Ultraspiracle," 2009, Arch. Insect Biochem. Physiol., 72:172-191.
Dinan, L. et al., "On the distribution of phytoecdysteroids in plants," 2001, Cell. Mol. Life Sci., 58:1121-1132.
Elbrecht, A., et al., "8-O-Acetylharpagide is a Nonsteroidal Ecdysteroid Agonist," 1996, Insect Biochem. Molec. Biol., 26:519-523.
Graham, L. et al., "Ligand binding by recombinant domains from insect ecdysone receptors," 2007, Insect Biochem. Molec. Biol., 37:611-626.
Graham, L. et al., "Purification and characterization of recombinant ligand-binding domains from the ecdysone receptors of four pest insects," 2007, Protein Express. Purif., 53:309-324.
Henrich, V. et al., "Developmental Effects of a Chimeric *ultraspiracle* Gene Derived from *Drosophila* and *Chironomus*," 2000, Genesis, 28:125-133.
Henrich, V. and Weinberger, C., "Effect of FXR activators on ecdysteroid receptor activity," 2000, Proceedings of the International Ecdysone Workshop, Rapperswil, Switzerland.
Henrich, V. at al., "The Multidimensional Partnership of EcR and USP," 2009, In: Ecdysone, structures and fundtions, G. Smagghe, ed., Ch. 14, pp. 359-373.

(56) References Cited

OTHER PUBLICATIONS

Henrich, V., "Strategies for Identifying Molecular Targets to Insect Ecdysteroid Receptors," Agric. University of North Carolina, Biology (Award Type—NCI Competitive Grant .cC), printed Aug. 12, 2003.

Henrich, V., "The Ecdysteroid Receptor," 2005, In: Comprehensive Insect Physiology, Biochemistry and Molecular Biology, 3:243-286.

Hiruma, K. and Riddiford, L., "Differential control of MHR3 promoter activity by isoforms of the ecdysone receptor and inhibitory effects of E75A and MHR3," 2004, Develop. Biol., 272:510-521.

Hormann, R. et al., "Multidimensional Quantitative Structure—Activity Relationships of Diacylhydrazine Toxicity to Lepidopteran and Coleopteran Insect Pests," 2008, QSAR Comb. Sci., 27:1098-1112.

Khelifi, M. et al., "Physical Control of Colorado Potato Beetle: A Review," 2007, Applied Engineering in Agric., 23:557-569.

Laudet, V. and Bonneton, F., "Evolution of Nuclear Hormone Receptors in Insects," 2005, In: Comprehensive Insect Physiology, Biochem. Molec. Biol., L. Gilbert et al., eds., 3:287-318.

Minakuchi, C. et al., "Effects of the structures of ecdysone receptor (EcR) and ultraspiracle (USP) on the ligand-binding activity of the EcR/USP heterodimer," 2007, J. Pestic. Sci., 32:379-384.

Nakagawa, Y., "Nonsteroidal Ecdysone Agonists," 2005, Vitam. Horm., 73:131-173.

Nakagawa, Y. et al., "Inhibition of [$^3$H][ponasterone A binding by ecdysone agonists in the intact Kc cell line," 2002, Insect Biochem. Molec. Biol., 32:175-180.

Nakagawa, Y. et al., "Quantitative structure-activity studies of insect growth regulators" XVI. Substituent effects of dibenzoylhydrazines on the insecticidal activity to Colorado potato beetle *Leptinotarsa decemlineata*, 1999, Pestic. Sci., 55:909-918.

Nakagawa, Y. et al., "Quantitative structure-activity studies of insect growth regulators: XVIII. Effects of substitutents on the aromatic moiety of dibenzoylhydrazines on larvicidal activity against the Colorado potato beetle *Leptinotarsa decemlineata*," 2001, Pest Manag. Sci., 57:858-865.

Nieva, C. et al., "Ultraspiracle promotes the nuclear localization of ecdysteroid receptor in mammalian cells," 2005, Biol. Chem., 386:463-470.

Palli, S. et al., "Ecdysteroid Receptors and Their Applications in Agriculture and Medicine," 2005, Vitamins and Hormones, 73:59-100.

Riddiford, L. et al., "Ecdysone Receptors and Their Biological Actions," 2001, Vitamins and hormones, 60:1-73.

Riddihough, G. and Pelham, H., "An ecdysone response element in the *Drosophila* hsp27 promoter," 1987, EMBO J., 6:3729-3734.

Ruff, H. et al., "Transcriptional Activity of Ecdysone Receptor Isoforms is Regulated by Modulation of Receptor Stability and Interaction with AB- and C-Domains of the Heterodimerization Partner Ultraspiracle," 2009, Arch. Insect Biochem. Physiol., 72:154-171.

Smagghe, G. and Degheele, D., "The Significance of Pharmacokinetics and Metabolism to the Biological Activity of RH-5992 (Tebufenozide) in *Spodoptera exempta, Spodoptera exigua*, and *Leptinotarsa decemlineata*," 1994, Pesticide Biochem. Physiol., 49:224-234.

Smagghe, G. and Degheele, D., "Action of a Novel Nonsteroidal Ecdysteroid Mimic, Tebufenozide (RH-5992), on Insects of Different Orders," 1994, Pesticide Science, 42:85-92.

Staal, G., "Anti Juvenile Hormone Agents," 1986, Ann. Reg. Entomol., 31:391-429.

Tal, D. et al., "Bile Acids. LXX. Preparative Separation of Kryptogenin from Companion Sapogennis by High Performance Liquid Chromatography," 1984, J. Liquid Chromatogr., 7:2591-2603.

Wheelock, C., et al., "High-throughput screening of ecdysone agonists using a reporter gene assay followed by 3-D QSAR analysis of the molting hormonal activity," 2006, Bioorganic & Medicinal Chemistry, 14:1143-1159.

Yao, T. et al., "Functional ecdysone receptor is the product of *EcR and Ultraspiracle* genes," 1993, Nature, 366:475-479.

Carmichael, J. et al., "The X-ray Structure of a Hemipteran Ecdysone Receptor Ligand-binding Domain," 2005, J. Biol. Chem., 280:22258-22269.

Iwema, T. et al., "Structural and functional characterization of a novel type of ligand-independent RXR-USP receptor," 2007, EMBO J., 26:3770-3782.

Jones, G. et al., "The retinoid-X receptor ortholog, ultraspiracle, binds with nanomolar affinity to an endogenous morphogenetic ligand," 2006, FEBS J., 273:1-14.

Li, Y. et al., "Identification and Characterization of a Juvenile Hormone Response Element and Its Binding Proteins," 2007, J. Biol. Chem., 282:37605-37617.

Miura, K. et al., "Characterization of the *Drosophila* Methoprene-tolerant gene product," 2005, FEBS J., 272:1169-1178.

Ogura, T. et al., "Molecular cloning, expression analysis and functional confirmation of ecdysone receptor and ultraspiracle from the Colorado potato beetle *Leptinotarsa decemlineata*," 2005, FEBS J., 272:4114-4128.

Reinking, J., et al., "The *Drosophila* Nuclear Receptor E75 Contains Heme and Is Gas Responsive," 2005, Cell, 122:195-207.

Smagghe, G., et al., "Comparative toxicity and ecdysone receptor affinity of non-steroidal ecdysone agonists and 20-hydroxyecdysone in *Chironomus tentans*," 2002, Insect Biochem. Mol. Biol., 32:187-192.

Notice of Allowance mailed May 4, 2010 corresponding to U.S. Appl. No. 10/929,090.

\* cited by examiner

SEQUENCE LISTING

<160> NUMBER OF SEQ ID NOS: 26

<210> SEQ ID NO 1
<211> LENGTH: 28
<212> TYPE: DNA
<213> ORGANISM: Artificial Sequence
<220> FEATURE:
<223> OTHER INFORMATION: Artificial = Synthetic construct

<400> SEQUENCE: 1
ggaatgattg catcatcgat aaaattcg                                    28

<210> SEQ ID NO 2
<211> LENGTH: 24
<212> TYPE: DNA
<213> ORGANISM: Artificial Sequence
<220> FEATURE:
<223> OTHER INFORMATION: Artificial = synthetic construct

<400> SEQUENCE: 2
gaggtctcga gtgagactcc tgta                                        24

<210> SEQ ID NO 3
<211> LENGTH: 33
<212> TYPE: DNA
<213> ORGANISM: Artificial Sequence
<220> FEATURE:
<223> OTHER INFORMATION: Artificial = synthetic construct

<400> SEQUENCE: 3
ctcgagtgta tgtatacagg tttgttaact gaa                              33

<210> SEQ ID NO 4
<211> LENGTH: 25
<212> TYPE: DNA
<213> ORGANISM: Artificial Sequence
<220> FEATURE:
<223> OTHER INFORMATION: Artificial = synthetic construct

<400> SEQUENCE: 4
aacaaacctg tatacataca ctcga                                       25

<210> SEQ ID NO 5
<211> LENGTH: 40
<212> TYPE: PRT
<213> ORGANISM: Artificial Sequence
<220> FEATURE:
<223> OTHER INFORMATION: Artificial = synthetic construct

<400> SEQUENCE: 5

Gly Met Asn Leu Glu Ala Arg Lys Thr Lys Lys Ile Lys Gly Ile
1               5                   10                  15

Gln Gln Ala Thr Thr Gly Val Ser Gln Glu Cys Met Tyr Thr Gly Leu
            20                  25                  30

Leu Thr Glu Ile Gln Cys Lys Ser
        35                  40

<210> SEQ ID NO 6
<211> LENGTH: 33
<212> TYPE: DNA
<213> ORGANISM: Artificial Sequence
<220> FEATURE:
<223> OTHER INFORMATION: Artificial = synthetic construct

<400> SEQUENCE: 6

-continued

```
cctgcgccac ggcggccgcc ggagctgtgc ctg                                33

<210> SEQ ID NO 7
<211> LENGTH: 29
<212> TYPE: DNA
<213> ORGANISM: Artificial Sequence
<220> FEATURE:
<223> OTHER INFORMATION: Artificial = synthetic construct

<400> SEQUENCE: 7
gtgggtatgc gcctcgagtg cgtcgtccc                                    29

<210> SEQ ID NO 8
<211> LENGTH: 29
<212> TYPE: DNA
<213> ORGANISM: Artificial Sequence
<220> FEATURE:
<223> OTHER INFORMATION: Artificial = synthetic construct

<400> SEQUENCE: 8
gatccgacaa gggttcaatg cacttgtca                                    29

<210> SEQ ID NO 9
<211> LENGTH: 35
<212> TYPE: DNA
<213> ORGANISM: Artificial Sequence
<220> FEATURE:
<223> OTHER INFORMATION: Artificial = synthetic construct

<400> SEQUENCE: 9
cacccggatc caccatgttg acgacgagtg gacaa                             35

<210> SEQ ID NO 10
<211> LENGTH: 32
<212> TYPE: DNA
<213> ORGANISM: Artificial Sequence
<220> FEATURE:
<223> OTHER INFORMATION: Artificial = synthetic construct

<400> SEQUENCE: 10
acctctctag actatgcagt cgtcgagtgg tc                                32

<210> SEQ ID NO 11
<211> LENGTH: 35
<212> TYPE: DNA
<213> ORGANISM: Artificial Sequence
<220> FEATURE:
<223> OTHER INFORMATION: Artificial = synthetic construct

<400> SEQUENCE: 11
cacccggatc caccatgaag cggcgctggt cgaac                             35

<210> SEQ ID NO 12
<211> LENGTH: 35
<212> TYPE: DNA
<213> ORGANISM: Artificial Sequence
<220> FEATURE:
<223> OTHER INFORMATION: Artificial = synthetic construct

<400> SEQUENCE: 12
cacccggatc caccatggat acttgtggat tagta                             35

<210> SEQ ID NO 13
<211> LENGTH: 35
```

```
<212> TYPE: DNA
<213> ORGANISM: Artificial Sequence
<220> FEATURE:
<223> OTHER INFORMATION: Artificial = synthetic construct

<400> SEQUENCE: 13
cacccggatc caccatgaag aagggacctg cgcca                              35

<210> SEQ ID NO 14
<211> LENGTH: 31
<212> TYPE: DNA
<213> ORGANISM: Artificial Sequence
<220> FEATURE:
<223> OTHER INFORMATION: Artificial = synthetic construct

<400> SEQUENCE: 14
ttttgaattc agcggcagca agcacctctg c                                  31

<210> SEQ ID NO 15
<211> LENGTH: 30
<212> TYPE: DNA
<213> ORGANISM: Artificial Sequence
<220> FEATURE:
<223> OTHER INFORMATION: Artificial = synthetic construct

<400> SEQUENCE: 15
ttttaagctt tagagtcggg accctactcc                                    30

<210> SEQ ID NO 16
<211> LENGTH: 31
<212> TYPE: DNA
<213> ORGANISM: Artificial Sequence
<220> FEATURE:
<223> OTHER INFORMATION: Artificial = synthetic construct

<400> SEQUENCE: 16
ttttgaattc tgctctattt gcggggatcg g                                  31

<210> SEQ ID NO 17
<211> LENGTH: 31
<212> TYPE: DNA
<213> ORGANISM: Artificial Sequence
<220> FEATURE:
<223> OTHER INFORMATION: Artificial = synthetic construct

<400> SEQUENCE: 17
ttttgaattc aagcgcgaag cggtccagga g                                  31

<210> SEQ ID NO 18
<211> LENGTH: 31
<212> TYPE: DNA
<213> ORGANISM: Artificial
<220> FEATURE:
<223> OTHER INFORMATION: Artificial = synthetic construct

<400> SEQUENCE: 18
ttttgaattc tgctcgattt gcggggacaa g                                  31

<210> SEQ ID NO 19
<211> LENGTH: 31
<212> TYPE: DNA
<213> ORGANISM: Artificial
<220> FEATURE:
<223> OTHER INFORMATION: Artificial = synthetic construct
```

```
<400> SEQUENCE: 19
ttttaagctt ctaagtatcc gactggtttt c                              31

<210> SEQ ID NO 20
<211> LENGTH: 31
<212> TYPE: DNA
<213> ORGANISM: Artificial
<220> FEATURE:
<223> OTHER INFORMATION: Artificial = synthetic construct

<400> SEQUENCE: 20
ttttgaattc aagcgggagg cggttcaaga a                              31

<210> SEQ ID NO 21
<211> LENGTH: 34
<212> TYPE: DNA
<213> ORGANISM: Artificial
<220> FEATURE:
<223> OTHER INFORMATION: Artificial = synthetic construct

<400> SEQUENCE: 21
ttttggatcc accatgacca ccatacactc gatc                           34

<210> SEQ ID NO 22
<211> LENGTH: 31
<212> TYPE: DNA
<213> ORGANISM: Artificial
<220> FEATURE:
<223> OTHER INFORMATION: Artificial = synthetic construct

<400> SEQUENCE: 22
tttttctaga ctatgtcttc atgtcgacgt c                              31

<210> SEQ ID NO 23
<211> LENGTH: 31
<212> TYPE: DNA
<213> ORGANISM: Artificial
<220> FEATURE:
<223> OTHER INFORMATION: Artificial = synthetic construct

<400> SEQUENCE: 23
cagatcacgt tactagaggc ctgctcgtcg g                              31

<210> SEQ ID NO 24
<211> LENGTH: 28
<212> TYPE: DNA
<213> ORGANISM: Artificial
<220> FEATURE:
<223> OTHER INFORMATION: Artificial = synthetic construct

<400> SEQUENCE: 24
ctcgtcggag gtgaggatgc tgcgtatg                                  28

<210> SEQ ID NO 25
<211> LENGTH: 41
<212> TYPE: DNA
<213> ORGANISM: Artificial
<220> FEATURE:
<223> OTHER INFORMATION: Artificial = synthetic construct

<400> SEQUENCE: 25
gtttgctaaa ggtctaccaa cgtttacaaa gatacccccag g                  41

<210> SEQ ID NO 26
<211> LENGTH: 25
```

```
<212> TYPE: DNA
<213> ORGANISM: Artificial
<220> FEATURE:
<223> OTHER INFORMATION: Artificial = synthetic construct

<400> SEQUENCE: 26
agcgacaagg gttcaatgca cttgt                                            25
```

METHODS, COMPOSITIONS, AND SYSTEMS FOR THE IDENTIFICATION OF SPECIES-SPECIFIC OR DEVELOPMENTAL STAGE-SPECIFIC INSECTICIDES

STATEMENT OF RELATED APPLICATIONS

The present application claims priority to U.S. Provisional Patent Application 60/723,724, filed Oct. 5, 2005, and is a continuation-in-part of U.S. patent application Ser. No. 10/929,090, filed Aug. 27, 2004, now U.S. Pat. No. 7,790,377 entitled "Compounds That Act To Modulate Insect Growth And Methods And Systems For Identifying Such Compounds," which claims priority to U.S. Provisional Patent Application Ser. No. 60/498,847, filed Aug. 29, 2003. U.S. patent application Ser. Nos. 10/929,090, 60/498,847, and 60/723,724 are incorporated by reference herein in their entireties.

FEDERAL SUPPORT

The work described herein was supported at least in part by Federal grants from the U.S. Department of Agriculture Competitive Grants program (00-35302-9327 and 03-35302-13474) and the National Institute of Environmental Health Sciences. Thus, the Federal government may have rights in this invention.

FIELD OF THE INVENTION

The present invention relates to compounds that act to modulate insect growth and methods and systems for identifying such compounds.

BACKGROUND

Insect development appears to be driven by the action of at least two hormone classes, the ecdysteroids and the juvenile hormones (JHs, juvenoids) (Riddiford, 1994, *Adv. Insect Physiol.*, 24:213-274; Gilbert et al., 2000, *Insect Biochem. Mol. Biol.*, 30:617-644; Thummel, 2002, *Insect Biochem. Mol. Biol.*, 32:113-120). It appears that ecdysteroids are responsible for initiating metamorphosis, and in some insects, regulating adult fertility. In contrast, JH appears to be required for reproductive processes such as adult female vitellogenesis (Wyatt, G. R., and K. G. Davey, 1996, *Adv. Insect Physiol.*, 26:1-15). Also, the simultaneous presence of ecdysteroids and juvenile hormone (JH) leads to larval-larval molting.

The insect ecdysteroid receptor is a heterodimer comprised of two nuclear receptors, the ecdysone receptor (EcR; Koelle et al, 1991, *Cell*, 4:59-77), and Ultraspiracle (USP; Oro et al, 1990, *Nature*, 347, 298-301; Henrich et al, 1990; Shea et al, 1990), that are stabilized by the presence of the insect molting hormone, 20-hydroxyecdysone (20E; Yao et al, 1992, *Cell*, 71:63-72; Yao et al, 1993, *Nature*, 366: 476-479; Thomas et al, 1993, *Nature*, 362:471-475). The heterodimer can interact with any one of several defined DNA sequence elements to regulate the transcription of target genes (Antoniewski et al, 1993, *Insect Biochem. Mol. Biol.*, 23:105-114; Vogtli et al, 1998, *Nuc. Acids Res.*, 10:2407-2414). Both EcR and USP appear to be required for the normal progression of premetamorphic development in *Drosophila melanogaster* (Hall and Thummel, 1998, *Development*, 125:4709-4717; Bender et al, 1997, *Cell*, 91:777-788; Li and Bender, 2001,; Henrich et al, 2000). Ecdysteroids represent the only endogenous class of steroid hormones known in *D. melanogaster* and other insects, and this single class can lead to both cell-specific and generally shared transcriptional changes (Riddiford et al, 2000, *Vitam. Horm.*, 60:1-73; Thummel, 2002).

There may also be mammalian counterparts to the insect receptor for ectdysteroids. Thus, EcR structurally resembles the vertebrate farnesoid X-activated receptor (FXR) (Forman, B. M., et al., 1995, *Cell*, 81:687-695). FXR is a member of the steroid receptor family that includes receptors for glucocorticoids, estrogen, vitamins A and D, thyroid hormones, and fatty acids. Also, there is evidence to suggest that USP may be the insect orthologue of the vertebrate retinoid X receptor (RXR) (Oro, et al., 1990). Comparisons of amino acids in the FXR and EcR DNA-binding domains reveal 60% identity, and the ligand binding domains (LBD) regions of these two receptors share about 45% identity. Nevertheless, the possible functional analogy between FXR/RXR and EcR/USP has yet to be resolved. For example, it has been shown that the vertebrate RXR is activated by methoprene acid but not JHIII or methoprene (Harmon, M. A., et al., 1995, *Proc. Natl. Acad. Sci. USA*, 92:6157-6160). In contrast, the insect USP complexes with JHIII and methoprene but not their acid metabolites (Jones, G. et al., 1997, *Proc. Natl. Acad. Sci. USA*, 94:13499-13503).

The diversity of ecdysteroid responses found among developing *Drosophila* tissues may involve the distinct roles of the three natural isoforms of EcR-EcRA, EcRB1, and EcRB2 (Talbot et al, 1993, *Cell*, 73:1323-1337). Expression of these isoforms appears to be regulated by different EcR promoters (A and B forms; Sung and Robinow, 2000, *Mech. Dev.*, 91:237-248) and alternative splicing (B1 and B2) of a single gene, such that the level and distribution of each isoform may vary among tissues (Talbot et al, 1993). Distribution of EcR isoforms in different tissues, however, has not yet been clearly correlated with isoform-specific phenotypic disruptions (Cherbas et al, 2003, *Development*, 130:271-284). Still, the B isoforms have been associated with larval functions (Schubiger et al, 1998, *Development*, 125:2053-2062). The B1 isoform is appears to be the isoform that is solely capable of mediating the ecdysteroid response in salivary gland cells (Bender et al, 1997). B2 seems to be the most efficient isoform for rescuing larval development in EcR mutants (Li and Bender, 2001). Thus, there appears to be a functional distinction between the two B isoforms. By contrast, the A isoform has been implicated in the remodelling of neurons during metamorphosis (Robinow et al, 1993, *Development*, 119: 1251-1259). Isoform-specific mutations of EcR further reveal the distinct functional roles during development. Generally, such mutations are lethal prior to metamorphosis. For example, many, although not all, mutations of EcR coding regions shared by the three isoforms cause death during embryogenesis (Bender et al, 1997; Carney and Bender, 2000, *Genetics*, 154:1203-1211).

*Drosophila* USP appears to be essential for metamorphosis (Hall and Thummel, 1998). Interestingly, the absence of USP during the late third instar induces subtly different phenotypic effects than the absence of EcR, suggesting divergent roles for these two proteins as metamorphosis approaches (Li and Bender, 2001). An interspecial chimeric USP has further revealed distinct larval and metamorphic functions for USP (Henrich et al, 2000). Also, evidence indicates that USP performs separable repressive and inductive functions (Schubiger and Truman, 2000, *Development*, 127:1151-1159; Ghbeish et al, 2001, *Proc. Natl. Acad. Sci., USA*, 98:3867-3872; Ghbeish and McKeown, 2002, *Mech. Devel.*, 111:89-98).

Cell culture studies have demonstrated that the individual *Drosophila* EcR isoforms may not be equivalent in their performance. Despite these differences, each of the isoforms appear to mediate elevated transcription levels in response to ecdysteroids (Mouillet et al, 2001, *Eur. J. Biochem.*, 268: 1811-1819). Also, each of the isoforms are potentiated by the simultaneous presence of JHIII with an activating ecdysteroid (Henrich et al, 2003, *Insect Biochem. Mol. Biol.*, 33:1239-1247).

Thus, insect development is regulated on a variety of levels. There is a need for the development of compounds that can interrupt insect morphogenesis and growth in a highly specific manner, so as to avoid any untoward side effects. Also, there is a need to develop species-specific and/or developmental stage-specific insecticides, so that insects that are detrimental may be specifically targeting while minimizing adverse effects on beneficial species.

SUMMARY

Embodiments of the present invention comprise compositions, systems and methods for the identification of species-specific or developmental stage-specific insecticides. The present invention may be embodied in a variety of ways.

For example, embodiments of the present invention comprise a system for the identification of species-specific or stage-specific insecticides. In one embodiment, the system comprises a plurality of isolated nucleic acid molecules, each nucleic acid molecule comprising a DNA sequence that encodes a polypeptide comprising at least a portion of an Ecdysone receptor (EcR) isoform from a distinct species, such that in combination, the isolated nucleic acid molecules comprise DNA sequences that encode for EcR isoforms from at least two different species. In another embodiment, the system comprises a plurality of isolated nucleic acid molecules, each nucleic acid molecule comprising a DNA sequence that encodes a polypeptide comprising at least a portion of an Ultraspiracle (USP) protein from a distinct species, such that in combination, the isolated nucleic acid molecules comprise DNA sequences that encode for USP polypeptides from at least two different species. In yet another embodiment, the system may comprise a plurality of isolated nucleic acid molecules, each nucleic acid molecule comprising a DNA sequence that encodes a polypeptide comprising at least a portion of an Ecdysone receptor (EcR) isoform from a distinct species, such that in combination, the isolated nucleic acid molecules comprise DNA sequences that encode for EcR isoforms from at least two different species; and a plurality of isolated nucleic acid molecules, each nucleic acid molecule comprising a DNA sequence that encodes a polypeptide comprising at least a portion of an Ultraspiracle (USP) protein from a distinct species, such that in combination, the isolated nucleic acid molecules comprise DNA sequences that encode for USP polypeptides from at least two different species.

In another embodiment, the present invention may comprise a method for the identification of species-specific and stage-specific insecticides. The method may comprise generating a first and second cell, where each cell comprises at least one of a species-specific (or stage-specific) EcR protein or a species-specific (or stage-specific) USP protein. The method may additionally comprise exposing each of the first and second cells to an EcR activating hormone, and adding the compound to be tested for insecticidal activity to both the first and the second cell.

For example, the method may comprise the steps of: transfecting a first mammalian cell with a first vector comprising a nucleotide sequence that encodes at least a portion of a USP polypeptide comprising at least a portion of an Ecdysone receptor (EcR) isoform; transfecting a second mammalian cell population with a vector comprising a nucleotide sequence that encodes for at least a portion of a USP polypeptide from a second species and a second vector comprising a DNA sequence that encodes a polypeptide comprising at least a portion of an Ecdysone receptor (EcR) isoform; and comparing the ability of the compound of interest to increase transcription of the reporter gene in the first and second cell populations.

In yet another embodiment, the method may comprise transfecting a first mammalian cell population with a first vector comprising a nucleotide sequence that encodes for at least a portion of an EcR polypeptide from a first species, and a second vector comprising a DNA sequence that encodes a polypeptide comprising at least a portion of a USP polypeptide; transfecting a second mammalian cell population with a vector comprising a nucleotide sequence that encodes for at least a portion of an EcR polypeptide from a second species and a second vector comprising a DNA sequence that encodes a polypeptide comprising at least a portion of a USP polypeptide; and comparing the ability of a compound of interest to increase transcription of the reporter gene in the first and second cell populations.

The present invention also comprises compounds that act as insecticides by their ability to inhibit insect growth, reproduction, and/or morphogenesis. Thus, in another embodiment, the present invention comprises a composition for use as a stage-specific or species-specific insecticide comprising a compound that increases EcR-mediated transcription (and/or FXR-mediated transcription) mixed with a suitable carrier for application to plants.

Certain embodiments of the present invention may provide certain advantages. Thus, embodiments of the systems, methods and DNA or protein constructs of the present invention may provide species-specific and/or developmental stage specific insecticides.

Also, embodiments of the systems, methods and constructs of the present invention may provide a systematic approach for classifying specific EcR and USP proteins (and protein domains) in terms of their effects on a variety of molecular parameters. For example, analysis of the effects of the mutated proteins on the ability of modulators to change the function of the protein may allow for the development of insecticides that are specific to particular species or particular stages of insect development.

Also, the present invention comprises methods and systems to identify natural compounds derived from plants that have the ability to increase EcR-mediated transcription and/or FXR-mediated transcription and thus, may be potential insecticides. Such natural compounds are potentially nontoxic insecticides; some of the compounds may even form part of the human diet.

Further details on each of these aspects of the present invention are set forth in the following description, figures, and claims. It is to be understood that the invention is not limited in its application to the details set forth in the following description, figures and claims, but is capable of other embodiments and of being practiced or carried out in various ways.

DETAILED DESCRIPTION

Definitions

Figure 1A:
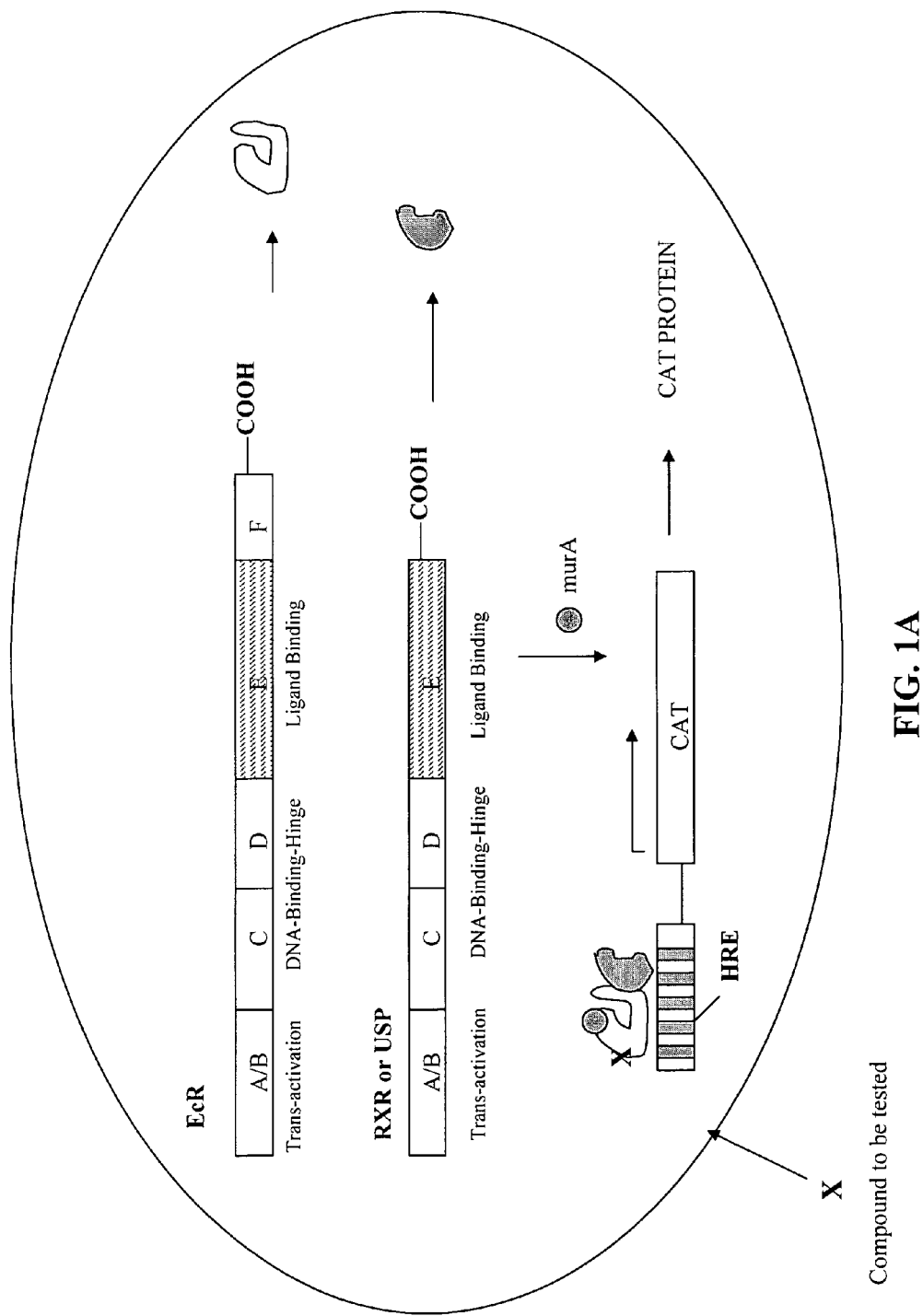
FIG. 1 shows a schematic diagrams of cell-based assay systems for detecting insecticides in accordance with example embodiments of the present invention where (1A) shows activation of EcR-mediated transcription potentiated by an ecdysteroid by compound X, and (1B) shows activation of FXR-mediated transcription by compound X.

The following definitions may be used to understand the description herein. Unless defined otherwise, all technical and scientific terms used herein have the same meaning as commonly understood by one of ordinary skin in the art.

The term "a" or "an" as used herein may refer to more than one object unless the context clearly indicates otherwise. The term "or" is used interchangeably with the term "and/or" unless the context clearly indicates otherwise.

As used herein, "stage-specific" or "developmental stage-specific" insecticides are insecticides that display increased toxicity at one stage of insect development as compared to other stages of insect development. As used herein, "species-specific" insecticides are insecticides that display increased toxicity for a particular species of insect as compared to other species of insects.

As used herein, a "ligand" is a molecule that interact either directly or indirectly with a receptor to form a complex. An "agonist" comprises a compound that binds to a receptor to form a complex that elicits a pharmacological response specific to the receptor involved. An "antagonist" comprises a compound that binds to an agonist or a receptor to form a complex that does not give rise to a substantial pharmacological response and can inhibit the biological response induced by an agonist.

"Polypeptide" and "protein" are used interchangeably herein to describe protein molecules that may comprise either partial or full-length proteins. As used herein, a "polypeptide domain" comprises a region along a polypeptide that comprises an independent unit. Domains may be defined in terms of structure, sequence and/or biological activity. In one embodiment, a polypeptide domain may comprise a region of a protein that folds in a manner that is substantially independent from the rest of the protein. Domains may be identified using domain databases such as, but not limited to PFAM, PRODOM, PROSITE, BLOCKS, PRINTS, SBASE, ISREC PROFILES, SAMRT, and PROCLASS.

A "nucleic acid" is a polynucleotide such as deoxyribonucleic acid (DNA) or ribonucleic acid (RNA). The term is used to include single-stranded nucleic acids, double-stranded nucleic acids, and RNA and DNA made from nucleotide or nucleoside analogues.

The term "vector" refers to a nucleic acid molecule that may be used to transport a second nucleic acid molecule into a cell. In one embodiment, the vector allows for replication of DNA sequences inserted into the vector. The vector may comprise a promoter to enhance expression of the nucleic acid molecule in at least some host cells. Vectors may replicate autonomously (extrachromasomal) or may be integrated into a host cell chromosome. In one embodiment, the vector may comprise an expression vector capable of producing a protein derived from at least part of a nucleic acid sequence inserted into the vector.

The term "fusion protein" may refer to a protein or polypeptide that has an amino acid sequence derived from two or more proteins. The fusion protein may also include linking regions of amino acids between amino acids portions derived from separate proteins. Unless specifically stated, there is no required order of linking polypeptides to form a fusion protein.

The term "percent identical" or "percent identity" refers to sequence identity between two amino acid sequences or between two nucleic acid sequences. Percent identity can be determined by aligning two sequences and refers to the number of identical residues (i.e., amino acid or nucleotide) at positions shared by the compared sequences. Sequence alignment and comparison may be conducted using the algorithms standard in the art (e.g. Smith and Waterman, *Adv. Appl. Math.*, 1981, 2:482; Needleman and Wunsch, 1970, *J. Mol. Biol.*, 48:443); Pearson and Lipman, 1988, *Proc. Natl. Acad. Sci. USA,* 85:2444) or by computerized versions of these algorithms (Wisconsin Genetics Software Package Release 7.0, Genetics Computer Group, 575 Science Drive, Madison, Wis.) publicly available as BLAST and FASTA. Also, ENTREZ, available through the National Institutes of Health, Bethesda Md., may be used for sequence comparison. In one embodiment, percent identity of two sequences may be determined using GCG with a gap weight of 1, such that each amino acid gap is weighted as if it were a single amino acid or nucleotide mismatch between the two sequences.

An "effective amount" as used herein means the amount of an agent that is effective for producing a desired effect. Where the agent is being used to achieve a insecticidal effect, the actual dose which comprises the effective amount may depend upon the route of administration, and the formulation being used.

As used herein, "modulation of insect growth" includes the modulation of the growth of an individual insect or an insect population and includes modulation of insect reproduction, morphogenesis, and survival. As used herein, "insect growth" comprises growth and development of an individual insect and/or an insect population and thus, refers to the growth, morphogenesis, and survival of an individual insect, or an insect population.

As used herein, an "increase in transcription" comprises an increase from a measurable basal level to a higher level. Alternatively, an "increase in transcription" may comprise an increase from an undetectable level to a measurable level. As used herein, "activation of FXR" or "activation of EcR" describes increasing FXR-mediated transcription or EcR-mediated transcription, respectively. As used herein, "FXR-mediated transcription" comprises a gene transcription event that requires binding of the activated farnesoid-X-receptor to a promoter upstream of the gene being transcribed. As used herein, "EcR-mediated transcription" comprises a gene transcription event that requires binding of the activated ecdysone receptor to a promoter upstream of the gene being transcribed. As used herein, "potentiation" of hormone activated transcription comprises an increase in transcription induced by hormones that bind to hormone response elements upstream of the gene being transcribed.

A "hormone response element" (HRE) comprises a nucleotide region upstream of a gene that mediates the effect of a steroid hormone. An "isoform" is a variant form of a protein that has the same general function as another protein but which may have small differences in its sequence either because it is encoded by a different gene, is expressed by a different promoter in the same gene, or is derived by alternative splicing of the same pre-mRNA. For example, EcR may exists in at least three versions having trans-activating regions that differ in sequence to provide isoforms EcRA, EcRB, and EcRB2, each of which can activate transcription of a gene having an EcR HRE in its promoter. EcRA is derived from a different promoter of the EcR gene, and B1 and B2 are derived from alternative splicing of a pre-mRNA. A "ligand binding domain" is that portion of a protein or polypeptide involved in binding of a ligand.

A "juvenile hormone mimetic" is a compound that functions like any one of the natural juvenile hormones such as JHI, JH II, or JH III. The normal physiological functions of the naturally-occuring compounds are compromised by ectopic or exogenous administration of any number of juvenile hormone mimetic compounds.

An "insecticide synergist" is a compound that acts in synergy with an insecticide to provide a response that is greater than additive.

A "monoterpene" is an acyclic or cyclic $C_{10}$ hydrocarbon composed of two isoprene units and their oxygenated derivatives. Common monoterpenes include geraniol, limonene, α-pinene, camphor. A "sesquiterpene" is an acyclic or cyclic $C_{15}$ hydrocarbon and their oxidized derivatives composed of three isoprene units. A "diterpene" is a acyclic or cyclic $C_{20}$ hydrocarbon and their oxidized derivatives composed of four isoprene units. A "triterpene" is a acyclic or cyclic $C_{30}$ hydrocarbon and their oxidized derivatives composed of six isoprene units. As used herein "coumarin" is 2H-1-Benzopyran-2-one. A "furocoumarin" is a psoralen derivative of coumarin such as bergamotin. As used herein "phenylpropanoid" is a compound derived from phenylalanine and cinnamic acid. A "flavonoid" is a phenolic compound build up of two aromatic rings and held together by a C3 unite. Flavonoids include chalcones, isoflavanoids (rotenone), flavolignans (silybin). As used herein, a "polyketide" included molecules synthesized form acetyl CoA, propionyl CoA, butyryl CoA, malonyl CoA, methylmalonyl CoA, and ehtylmalonyl CaA intermediates.

Identification of Species-Specific Insecticide Compounds

Embodiments of the present invention provide methods and systems for the identification of compounds that act as species-specific insecticides or modulators of insect growth and/or development. Bioassays assembled using these receptors may be employed to guide the rational design of novel chemicals that specifically target insect pests. The present invention recognizes that there are nuclear receptor-gated signaling pathways in insects that may uniformly respond to a broad range of natural and synthetic insecticides. For example, the compounds of the present invention may target the ecdysone receptor (EcR) to act as species-specific insect growth regulators and/or to interfere with insect development.

In other embodiments, the present invention provides compositions comprising compounds that may function as species-specific or developmental stage-specific insect growth regulators for the control of pests. The compounds used as growth regulators may be natural compounds, isolated from everyday plants such as sesame seeds, hops, coffee, and bergamot oil found in tea.

The present invention may be embodied in a variety of ways.

In one embodiment, the present invention may comprise a system for the identification of species-specific and/or stage-specific insecticides. In an embodiment, the system may comprise a plurality of isolated nucleic acid molecules, wherein each nucleic acid molecule comprises a DNA sequence that encodes a polypeptide comprising at least a portion of an Ecdysone receptor (EcR) isoform from a distinct species. For example, the system may comprise a DNA sequence that encodes a polypeptide comprising at least a portion of an Ecdysone receptor (EcR) isoform from a first insect species, and a DNA sequence that encodes a polypeptide comprising at least a portion of an Ecdysone receptor (EcR) isoform from a second insect species, and a DNA sequence that encodes a polypeptide comprising an Ecdysone receptor (EcR) isoform from a third insect species.

In an alternative embodiment, where the system is being used for the development of stage-specific insecticides, the EcR isoforms may each be from the same species, but specific to a particular stage of insect development. For example, the system may comprise a DNA sequence that encodes a polypeptide comprising at least a portion of an Ecdysone receptor (EcRA) isoform, and a DNA sequence that encodes a polypeptide comprising at least a portion of an Ecdysone receptor (EcRB1) isoform and a DNA sequence that encodes a polypeptide comprising an Ecdysone receptor (EcRB2) isoform.

The system may also comprise a second plurality of isolated nucleic acid molecules, each nucleic acid molecule comprising a DNA sequence that encodes a polypeptide comprising at least a portion of an Ultraspiracle (USP) protein from a distinct species. The USP polypeptides may comprise proteins from the same species as the EcR polypeptides (e.g., the first, second, and third species), or from different species (e.g., a fourth, fifth and sixth species). In an alternative embodiment, where the system is being used for the development of stage-specific insecticides, the USP polypeptide may each be from the same species, but specific to a particular stage of insect development.

The system may also comprise a first and second cell population, where each cell population comprises at least one of a species-specific (or stage-specific) EcR protein or a species-specific USP protein. For example, the system may comprise a first mammalian cell population transfected with a first vector comprising a nucleotide sequence that encodes for at least a portion of a USP polypeptide from a first species and a second vector comprising a DNA sequence that encodes for a polypeptide comprising at least a portion of an Ecdysone receptor (EcR) isoform. The system may also comprise a second mammalian cell population transfected with a second vector comprising a nucleotide sequence that encodes a USP polypeptide from a second species and a second vector comprising a DNA sequence that encodes a polypeptide comprising at least a portion of an Ecdysone receptor (EcR) isoform. In alternate embodiments, the EcR isoform may be from the same species as the EcR isoform used in the first cell population or from a different species than the EcR used in the first cell population. Also, in certain embodiments, at least one of the EcR isoforms may be from the same species as at least one of the USP polypeptides.

Alternatively, the system may comprise a first mammalian cell population transfected with a first vector comprising a nucleotide sequence that encodes for at least a portion of an EcR isoform from a first species and a second vector comprising a DNA sequence that encodes a polypeptide comprising at least a portion of a USP polypeptide. The system may also comprise a second mammalian cell population transfected with a second vector comprising a nucleotide sequence that encodes at least a portion of an EcR isoform polypeptide from a second species and a second vector comprising a DNA sequence that encodes a polypeptide comprising at least a portion of a USP polypeptide. In an embodiment, the USP polypeptide may be from the same species as the USP polypeptide used in the first cell population or from a different species. Also, in certain embodiments, at least one of the USP polypeptides may be from the same species as at least one of the EcR isoform polypeptides.

In an embodiment, the portion of the EcR or USP polypeptide used in the systems of the present invention may be derived from an insects. Any insect comprising a EcR and/or USP protein or analogous proteins may be used for the methods of the present invention. In an embodiment, the insect may comprise at least one of a diptheria, hemiptera, coleoptera, neuroptera, lepitdoptera, or ants. In certain embodiments, the insect species comprises at least one of aphids, scale insects, leaf hoppers, white fly and blowflies. For example the insect species may comprise insects that are found on alfalfa, such as the alfalfa caterpillar (e.g., *Colias eurytheme*), Alfalfa Weevil (e.g., *Hypera postica*) Beet Armyworm (e.g., *Spodoptera exigua*), Blister Beetles (e.g., *Epicauta* spp., *Lytta* spp.), Blue Alfalfa Aphid (e.g., *Acrythosiphon kondoi*) and Pea Aphid (e.g., *Acrythosiphon pisum*), Cowpea Aphid (e.g., *Aphis craccivora*), Egyption Alfalfa Weevil (e.g., *Hypera brunneipennis*), Alfalfa Grasshoppers (e.g., *Melanoplus* spp; *Trimerotropis* spp), Alphafa Leafhoppers such as the Garden Leafhopper (e.g., *Empoasca solana*), Potato Leafhopper (e.g., *E. fabae*), Mexican Leafhopper (e.g., *E. mexara*), the Alphafa Mormon Cricket (e.g., *Anabrus simplex*), Spider Mits (e.g., *Tetranychus urticae, Tetranychus* spp.), Spottted Alfalfa Aphid (e.g., *Therioaphis maculata*), Variegated and Other Cutworms such as the Granulate cutworm (e.g., *Agrotis subterranea*), Variegated cutworm (e.g., *Peridroma saucia*), the Webworm (e.g., *Loxosteg* spp.), or the Western Yellowstriped Armyworm (e.g., *Spodoptera praefica*). Or, the insect species may comprise insects that are found on apples such as the Apple Magot (e.g., *Rhagoletis pomonella*), Apple Pandemis (e.g., *Pandemis pyrusana*), Caodling Moth (e.g., *Cydia pomonella*), Cribrate Weevil (e.g., *Otiorhynchus cibricollis*), European Red Mite (e.g., *Panonychus ulmi*) Eyespotted Bud Moth (e.g., *Spilonota ocellana*), Fruittre Leafroller (e.g., *Archips argyrospila*), Green Apple Aphid (e.g., *Aphis pomi*), Green Fruitworms such as the Speckled Green Fruitworm (e.g., *Orthosia hibisci*), Humped Green Fruitworm (e.g., *Amphipyra pyramidoides*), Leafhoppers such as the white apple leafhopper (e.g., *Typhlocyba pomaria*) or the Rose Leafhopper (e.g., *Edwadsiana rosae*), Leafminers (e.g., *Phyllonorycter* spp.), Lygus Bugs (e.g., *Lygus hesperus, Lygus ellisus*), Obliquebanded Leafroller (e.g., *Choristoneura rosaceana*), Omnivorous Leafroller, Orange Tortrix, Rosy Apple Aphid, and the like. Or the insect species may comprise insects that are found on small grains such as Armyworms (e.g., *Pseudaletia unipuncta*) and the Western Yellowstriped Armyworm (e.g., *Spodoptera praefica*), Bird Cherry-oat Aphid (e.g., *Rhopalosiphum padi*), Black Grass Bug (e.g., *Irbisia* spp), Corn Leaf Aphid (e.g., *Rhopalsiphum maidis*), Greenbug (e.g., *Schizaphis graminum*), Range Crane Fly (e.g., *Tipula* spp), Russian Wheat Aphid (e.g., *Diuraphis noxia*), Wheat Stem Maggot (e.g., *Meromyza americana*), Wireworms (e.g., *Aeolus* sp., *Anchastus* spp. *Melanotus* spp., *Limonius* spp.), Potato Tuberworm (e.g., *Phthorimaea operculella*), Flea Beetles (e.g., *Epitrix* spp), or Siverleaf Whitefly (e.g., *Bemisia argentifolii*). Or, the insect species may comprise insects that are found on corn such as Armyworms (e.g., *Pseudaletia unipuncta*), the Western Yellowstriped Armyworm (e.g., *Spodoptera praefica*), or the Beet Armyworm (e.g., *Spodoptera exigua*), Corn Earworm (e.g., *Helicoverpa zea*), Corn Leafhopper (e.g., *Dalbulus maidis*), Corn Leafminer (e.g., *Agromyza* sp.), Cucumber Beetles such as the Western Spotted Cucumber Beetle (e.g., *Acalymma trivittatum*), the Banded Cucumber Beetle (e.g., *Diabrotica Balteata*), the Spotted Cumber Beetle (e.g., *Diabrotica undecimpunctata howardi*), the Seedcorn Maggot (e.g., *Delia platura*), Thrips (e.g., *Frankliniella occidentalis, Frankliniella williamsi*), or False Church Bug (*Nysius raphanus*) and the like. Or insects that are found on celery, such as the Omnivorous leafroller (e.g., *Platynota stultana*), False celery Leafteri (e.g., *Udea profundalis*). Additional insects may comprise insects found on strawberries such as the Cycalmen Mite (e.g., *Phytonemus pallidus*), European Earwig (e.g., *Forficula auricularia*), Garden Symphylan (*Scutigerella immaculata*), or Root Beetles such as the Black vine weevil (e.g., *Otiorhynchus sulcatus*), Crbrate weevil (*Otiorhynchus cribricollis*), Fuller rose weevil (e.g., *Pantomorus cervinus*), Woods weevil (e.g., *Nemocetes incomptus*), or the Hoplia beetle (e.g., *Hoplia dispar; H. callipyge*). Or the insect may comprise a Pink Bollworm (e.g., *Pectinophora gossypiella*), Saltmarsh Catterpillar (e.g., *Estigmene acrea*), or Tabacco Budworm (e.g., *Heliothis virescens*). Or the insect may comprise a slug such as the Garden slug (e.g., *Arion hortensis*), Little Gray Slug (e.g., *Deroeras reticulatum*). Or the insect may comprise an insect found in trees such as the Hemlock Woolly Adelgid (e.g., *Adelges tsugae*), Pine Bark Beetle, and the like.

The system may also be used to test whether a compound is insectacidal to a beneficial insect as it may be desired to develop insectides that do not target such species. For example, a beneficial insect may comprise Monarch butterfly, honeybee, and a lady bug.

For example, the species may comprise a fly (e.g., *Drosophila melanogaster*). Or, the species may comprise a beetle (e.g., *Leptinotarsa decemlineata*). Or the insect species may comprise a bud worm (e.g., *Chroristoneura fumerifana*). Or, other insect species including *Manduca sexta* (Lepidoptera), *Locusta migratoria* (Orthoptera), *Heliothis virescens* (Lepidoptera), *Apis mellifera* (Hymenoptera), *Aedes aegypti* (lower Diptera), and *Tenebrio molitor* (Coleoptera) may also be employed.

The constructs of the invention may comprise USP polypeptides that include various domains and/or regions that may be important for biologicial activity. Thus, in one embodiment, the DNA sequence that encodes the USP polypeptide may comprise the hinge region and the ligand binding domain of the USP protein. Alternatively, the DNA sequence that encodes the USP polypeptide may comprise the DNA binding domain, the hinge region, and the ligand binding domain of the USP protein. In other embodiments, the DNA sequence that encodes the USP polypeptide may comprise the transactivation (A/B) domain, the DNA binding domain, the hinge region, and the ligand binding domain of the USP protein. In yet another embodiment the USP polypeptide may comprise mutations.

The system may comprise a mammalian cell-based system to reduce non-specific background. Thus, in one embodiment, the USP sequences may be operationally linked to a mammalian nuclear receptor transactivation domain.

In various embodiments, various species-specific EcR polypeptides, or EcR polypeptide isoforms may be used for the systems of the invention. Also, the EcR isoforms may, in certain embodiments, comprise mutations. In an embodiment, the mutations allow for identification of a potential insecticide that may interact with the EcR and/or USP proteins. Thus, in an embodiment, at least one EcR polypeptide comprises a mutation at the residue corresponding to lysine (L) 497 of the native *Drosophila melanogaster* EcR protein, wherein the lysine is changed to a glutamate (E). Additionally or alternatively, at least one EcR polypeptide may comprise a mutation at the residue corresponding to methionine (M) 504 of the native *Drosophila melanogaster* EcR protein, wherein the methionine is changed to an arginine (R). In yet another embodiment, at least one EcR polypeptide comprises a mutation at the residue corresponding to alanine (A) 483 of the native *Drosophila melanogaster* EcR protein, wherein the alanine is changed to a (T) threonine.

Other embodiments of the present invention may comprise methods for the identification of species-specific and stage-specific insecticides. The method may comprise generating a first and second cell population, where each cell population comprises at least one of a species-specific (or stage-specific) EcR protein or a species-specific USP protein. The method may additionally comprise exposing each of the first and second cell populations to an EcR activating hormone, and adding a compound to be tested for insecticidal activity to both the first and the second cell population.

For example, in an embodiment, the method may comprise the steps of: (a) transfecting a first mammalian cell population with a first vector comprising a nucleotide sequence that encodes at least a portion of a USP polypeptide from a first species, and a second vector comprising a DNA sequence that encodes a polypeptide comprising an Ecdysone receptor (EcR) isoform; (b) transfecting a second mammalian cell population with a second vector comprising a nucleotide sequence that encodes at least a portion of a USP polypeptide from a second species and a second vector comprising a DNA sequence that encodes a polypeptide comprising an Ecdysone receptor (EcR) isoform; and (c) comparing the ability of a compound of interest to increase transcription of the reporter gene in the first and second cell populations. Alternatively, the method may comprise the steps of: (a) transfecting a first mammalian cell population with a first vector comprising a nucleotide sequence that encodes an EcR polypeptide from a first species, and a second vector comprising a DNA sequence that encodes a polypeptide comprising at least a portion of a USP polypeptide; (b) transfecting a second mammalian cell population with a second vector comprising a nucleotide sequence that encodes a EcR polypeptide from a second species and a second vector comprising a DNA sequence that encodes a polypeptide comprising at least a portion of a USP polypeptide; and (c) comparing the ability of a compound of interest to increase transcription of the reporter gene in the first and second cell populations.

In an embodiment, the portion of the EcR or USP polypeptide used in the systems of the present invention may be derived from an insects. Any insect, including insects that are considered to be "pests" or beneficial insects comprising a EcR and/or USP protein or analogous proteins may be used for the methods of the present invention. The insects used for the methods of the invention may comprise any of the insects described herein. In an embodiment, the species from which the nucleic acid molecules encoding the USP polypeptide or the EcR polypeptide comprise *Drosophila melanogaster, Leptinotarsa decemlineata, Chroristoneura fumerifana, Manduca sexta, Locusta migratoria, Heliothis virescens, Apis mellifera, Aedes aegypti*, or *Tenebrio molitor*.

Although the method may be used for the identification of species-specific insecticides, the method may also be used for the identification of insecticides that are specific to a particular stage of insect development (as such developmental stages may be regulated at least in part by specific EcR and/or USP proteins) and/or a particular isoform of either the EcR protein or the USP proteins. In an alternative embodiment, where the method is being used for the development of stage-specific insecticides, the EcR isoforms may each be from the same species, but specific to a particular stage of insect development. For example, the cell populations may be transfected a DNA sequence that encodes a polypeptide comprising at least a portion of an Ecdysone receptor (EcRA) isoform, or a DNA sequence that encodes a polypeptide comprising at least a portion of an Ecdysone receptor (EcRB1) isoform; or a DNA sequence that encodes a polypeptide comprising an Ecdysone receptor (EcRB2) isoform rather than species-specific isoforms. For example, in an embodiment, the method may comprise the steps of: (a) transfecting a first mammalian cell population with a first USP vector comprising a nucleotide sequence that encodes a polypeptide comprising at least a portion of a USP protein and an EcR vector comprising a DNA sequence that encodes a polypeptide comprising at least a portion of a first Ecdysone receptor (EcR) isoform; (b) transfecting a second mammalian cell population with a second USP vector comprising a nucleotide sequence that encodes a polypeptide comprising at least a portion of a USP protein, and a vector comprising a DNA sequence that encodes a polypeptide comprising at least a portion of a second Ecdysone receptor (EcR) isoform; (c) co-transfecting both the first and the second mammalian cell population with a reporter gene linked to a hormone-responsive element (HRE); (d) exposing both cell populations to a EcR activating hormone; (e) adding the compound to be tested to both the first and the second mammalian cell population; and (f) comparing the ability of the compound of interest to increase transcription of the reporter gene.

The constructs of the invention may comprise USP polypeptides that include various domains and/or regions that may be important for biologicial activity. Thus, in one embodiment, the DNA sequence that encodes the USP polypeptide may comprise the hinge region and the ligand binding domain of the USP protein. Alternatively, the DNA sequence that encodes the USP polypeptide may comprise the DNA binding domain, the hinge region, and the ligand binding domain of the USP protein. In other embodiments, the DNA sequence that encodes the USP polypeptide may comprise the transactivation (A/B) domain, the DNA binding domain, the hinge region, and the ligand binding domain of the USP protein. In yet another embodiment the USP polypeptide may comprise mutations.

The system may comprise a mammalian cell population-based system to reduce non-specific background. Thus, in one embodiment, the USP sequences may be operationally linked to a mammalian nuclear receptor transactivation domain.

In various embodiments, various species-specific EcR polypeptides, or EcR polypeptide isoforms may be used for the methods of the invention. Also, the EcR isoforms may, in certain embodiments, comprise mutations. In an embodiment, the mutations allow for identification of a potential insecticide that may interact with the EcR and/or USP proteins. Thus, in an embodiment, at least one EcR polypeptide comprises a mutation at the residue corresponding to lysine (L) 497 of the native *Drosophila melanogaster* EcR protein, wherein the lysine is changed to a glutamate (E). Additionally or alternatively, at least one EcR polypeptide may comprise a mutation at the residue corresponding to methionine (M) 504 of the native *Drosophila melanogaster* EcR protein, wherein the methionine is changed to an arginine (R). In yet another embodiment, at least one EcR polypeptide comprises a mutation at the residue corresponding to alanine (A) 483 of the native *Drosophila melanogaster* EcR protein, wherein the alanine is changed to a (T) threonine.

In an embodiment, the method may further comprise co-transfecting both the first and the second mammalian cell population with a reporter gene linked to an mammalian hormone-responsive element (HRE). For example, in an embodiment, step (c) may further comprising the steps of: (i) exposing both cell populations to a EcR activating hormone; (ii) adding the compound to be tested to both the first and the second mammalian cell population; and (iii) comparing the ability of the compound of interest to increase transcription of the reporter gene.

Thus, in an embodiment, the present invention may comprise a method for the identification of species-specific and stage-specific insecticides comprising: (a) transfecting a first mammalian cell population with a first vector comprising a nucleotide sequence that encodes a USP polypeptide from a first species operationally linked to a mammalian transactivating domain, the USP polypeptide comprising a USP hinge region and ligand binding domain, and a second vector comprising a DNA sequence that encodes a polypeptide comprising at least a portion of an Ecdysone receptor (EcR) isoform; (b) transfecting a second mammalian cell population with a vector comprising a nucleotide sequence that encodes a USP polypeptide from a second species operationally linked to a mammalian transactivating domain, the USP polypeptide comprising a USP hinge region and ligand binding domain, and a second vector comprising a DNA sequence that encodes a polypeptide comprising at least a portion of an Ecdysone receptor (EcR) isoform; (c) co-transfecting both the first and the second mammalian cell population with a reporter gene linked to an mammalian hormone-responsive element (HRE); (d) exposing both cell populations to an EcR activating hormone; (e) adding the compound to be tested to both the first and the second mammalian cell population; and (f) comparing the ability of the compound of interest to increase transcription of the reporter gene in the first and second cell populations. Alternatively, the method may comprise: (a) transfecting a first mammalian cell population transfected with a first vector comprising a nucleotide sequence that encodes at least a portion of a USP polypeptide operationally linked a mammalian transactivating domain, and a second vector comprising a DNA sequence that encodes a polypeptide comprising at least a portion of an Ecdysone receptor (EcR) isoform from a first species (or specific to a particular stage of insect development); (b) transfecting a second mammalian cell population transfected with a second vector comprising a nucleotide sequence that encodes a USP polypeptide operationally linked to a mammalian transactivating domain, and a second vector comprising a DNA sequence that encodes a polypeptide comprising at least a portion of an Ecdysone receptor (EcR) isoform from a second species (or specific to a particular stage of insect development); (c) co-transfecting both the first and the second mammalian cell population with a reporter gene linked to an mammalian hormone-responsive element (HRE); (d) exposing both cell populations to an EcR activating hormone; (e) adding the compound to be tested to both the first and the second mammalian cell population; and (f) comparing the ability of the compound of interest to increase transcription of the reporter gene in the first and second cell populations.

Embodiments of the present invention also comprise nucleic acid constructs. In certain embodiments, the nucleic acid constructs comprise species-specific Ultraspiracle (USP) polypeptides. In an embodiment, such constructs may be insecticidal. In an embodiment, the portion of the EcR or USP polypeptide used in the systems of the present invention may be derived from an insects. Any insect, including insects that are considered to be "pests" or beneficial insects comprising a EcR and/or USP protein or analogous proteins may be used for the methods of the present invention. The insects used for the methods of the invention may comprise any of the insects described herein. In an embodiment, the species from which the nucleic acid molecules encoding the USP polypeptide or the EcR polypeptide comprise *Drosophila melanogaster, Leptinotarsa decemlineata, Chroristoneura fumerifana, Manduca sexta, Locusta migratoria, Heliothis virescens, Apis mellifera, Aedes aegypti*, or *Tenebrio molitor*.

Thus, in one embodiment, the present invention comprises a nucleic acid molecule encoding a *Drosophila* Ultraspiracle (USP) polypeptide comprising a portion of the A/B region, the DNA binding domain, the hinge region, and the ligand binding domain of USP. In another embodiment, the present invention may comprise a nucleic acid molecule encoding a *Drosophila* Ultraspiracle (USP) polypeptide comprising the DNA binding domain, the hinge region, and the ligand binding domain of USP. Also, the present invention may comprise a nucleic acid molecule encoding a portion of a *Drosophila* Ultraspiracle (USP) polypeptide comprising the hinge region and the ligand binding domain of USP.

In certain embodiments, the nucleic acid constructs comprise species-specific or stage-specific Ecdysone receptor (EcR) polypeptides. In an embodiment, such constructs may in themselves be insecticidal.

For example, the nucleic acid constructs may comprise an EcR polypeptide or isoform isolated from a particular species. In other embodiments, the EcR polypeptide may comprise a mutation to alter activity of the polypeptide. In one embodiment, the present invention comprises a nucleic acid molecule encoding an Ecdysone Receptor (EcR) polypeptide comprising a mutation at the residue corresponding to lysine (L) 497 of the native *Drosophila melanogaster* EcR protein, wherein the lysine is changed to a glutamate (E). In another embodiment, the present invention comprises a nucleic acid molecule encoding an Ecdysone Receptor (EcR) polypeptide comprising a mutation at the residue corresponding to methionine (M) 504 of the native *Drosophila melanogaster* EcR protein, wherein the methionine is changed to an arginine (R). Also, in yet another embodiment, the present invention comprises a nucleic acid molecule encoding an Ecdysone Receptor (EcR) polypeptide comprising a mutation at the residue corresponding to alanine (A) 483 of the native *Drosophila melanogaster* EcR protein, wherein the alanine is changed to a (T) threonine.

a. Potentiation of Ecdysone Receptor-Dependent Transcription in a Mammalian Culture System The present invention recognizes that a variety of natural and synthetic insecticides can act to modulate transcriptional activity programmed by EcR and its mammalian counterpart, FXR. Thus, embodiments of the present invention comprise compounds that activate EcR (and/or FXR) as potential insecticides. In other embodiments, the present invention also provides compositions that comprise such EcR-activating and/or potentiating compounds isolated from plants or plant metabolites as environmentally friendly insecticides.

The present invention recognizes that there may be overlap between the mammalian FXR/RXR system and the insect EcR/USP systems, and provides numerous plant-derived and man-made JHs that have the ability to increase transcriptional activity programmed by EcR and/or FXR. Thus, in various embodiments, the present invention comprises assay systems and methods to test various EcR isoforms and chimeras as having the ability mediate a transcriptional response to ecdysteroids and JHs. In addition, the present invention comprises assay systems and method to test species specific EcR isoforms and USP proteins for the development of species-specific insecticides.

Applicants have described a mammalian cell-based assay system that provides the ability to reconstitute ecdysteroid responsive transcriptional effects in an otherwise non-responsive mammalian cell culture (see U.S. Patent Publication No.: 2005/0049230). Because the assay is performed in mammalian cells which normally lack endogenous EcR or FXR activity, components required for activity may be controlled.

Thus, embodiments of the present invention comprise methods and systems to evaluate the ability of specific compounds to activate either EcR-mediated transcription (or FXR-mediated transcription), wherein compounds exhibiting the ability to activate EcR-mediated transcription or FXR-mediated transcription comprise potential modulators of insect growth and/or insecticides. In an embodiment, the EcR and/or FXR components are derived from specific species and/or are active during specific stages of insect development.

Figure 1B:
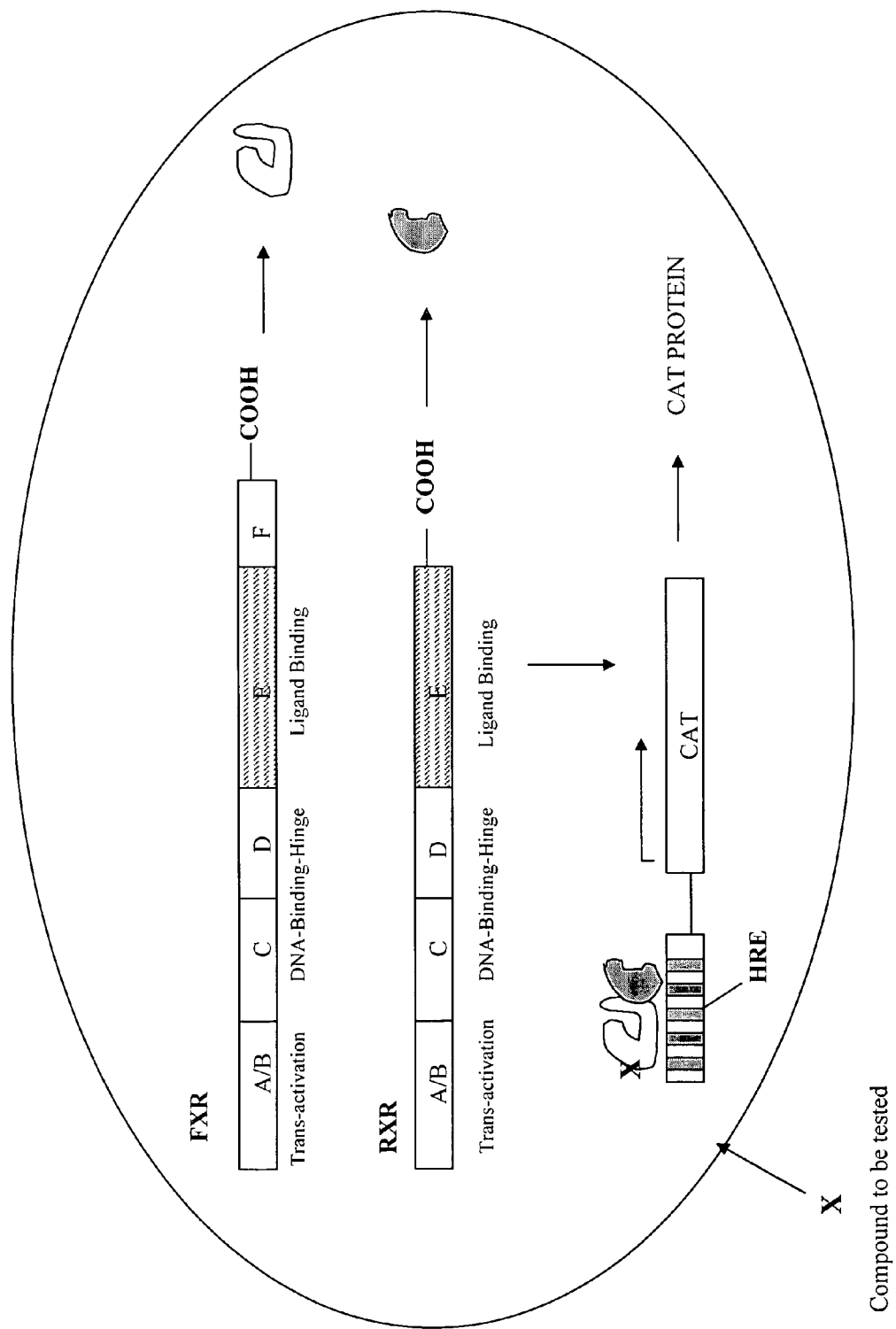

Example embodiments of assay systems of the present invention are depicted schematically in FIGS. 1A and 1B. The assay systems as depicted in FIGS. 1A and 1B are non-limiting in that the mechanism of interaction of the various assay components may vary from that depicted in the drawing, while still providing a functional assay system. For example, in one embodiment, the compound to be tested, (X), may bind directly to FXR or EcR protein as indicated schematically in FIG. 1. Alternatively, compound (X) may modify FXR (or EcR) activity without directly binding to the protein, but indirectly in some manner.

As shown in FIG. 1A, the assay system may comprise four components. The first component may comprise a DNA construct that encodes a functional EcR. For example, in one embodiment, a cell (shown as the large oval in FIG. 1) may be transfected with a plasmid comprising sequences that encode an EcR polypeptide. In one embodiment, the EcR polypeptide may comprise an EcR chimera comprising a mammalian (e.g., human) glucocorticoid receptor (GR or hGR) transactivation domain (A/B) attached to an insect (e.g., Drosophila) EcR DNA binding domain and hinge (DBD) (C/D) and ligand binding domain (LBD) (E). Also, in some cases the construct may contain a region (F) that may function as a transactivation domain (Palli et al., 2003, Eur. J. Biochem., 270:1308-1315).

The second component of the assay may comprise the binding partner needed for EcR activity. In one embodiment, a cell may therefore be co-transfected with a second expression plasmid comprising sequences that encode an insect USP. These proteins may also comprise a trans-activating domain (A/B) and a DNA binding domain (C) and hinge (D), and a ligand binding domain (E). In an embodiment, RXR and/or USP may not necessarily comprise an (F) domain. The plasmids may be co-transfected into a mammalian cell population, such as a Chinese Hamster Ovary (CHO) cell, so that there is no endogenous EcR or ecdysteroid present.

The third component of the assay system may be an exogenous ecdysteroid such as muristerone A (murA), that may act to induce EcR dependent transcription. Finally, the assay system may comprise a means to measure EcR-mediated transcription or FXR-mediated transcription. The response of transfected cells to a compound (X) that is able to increase EcR-mediated transcription FXR-mediated transcription or may be measured using a reporter plasmid bearing a EcR (or FXR) hormone responsive element (HRE). In one embodiment, the reporter plasmid may comprise a construct having multiple copies of the hormone-responsive element inserted upstream of a gene having a measurable gene product. In one example embodiment, multiple copies of an ecdysone-responsive element, hsp27 EcRE, are inserted into the mouse mammary tumor virus (MTV) promoter positioned upstream of the bacterial chloramphenical acetyltransferase (CAT) gene to generate an $(EcRE)_5$-ΔMTV-CAT reporter plasmid. The compound to be tested (X) may then added to the cells, and the effect on EcR or FXR activated transcription of the CAT gene is determined.

In an alternative embodiment, the reporter gene may comprise the luciferase gene (LUC) or a green fluorescent protein (GFP). For example, in an embodiment, the reporter plasmid comprises an $(EcRE)_5$-ΔMTV-LUC construct produced as described herein. Using the luciferase gene may allow for FXR or EcR activated transcription to be measured in-situ by monitoring the luminescence of the cells or organism being used in the assay.

FIG. 1B shows a non-limiting example embodiment of an assay system for FXR-mediated transcription and measurement of the ability of a compound, (X), to modulate FXR-mediated transcription. In this assay system, a hormone, such as murA, may not be required. Thus, in the assay system shown in FIG. 1B, compound (X) may modify transcription of the reporter gene that is mediated by FXR, but that does not require or employ murA. As described for FIG. 1A, the compound to be tested, (X), may bind directly to FXR or EcR protein, or it may modify FXR (or EcR) activity without directly binding to the protein, but indirectly in some manner.

b. Chimeric Constructs

Figure 2:
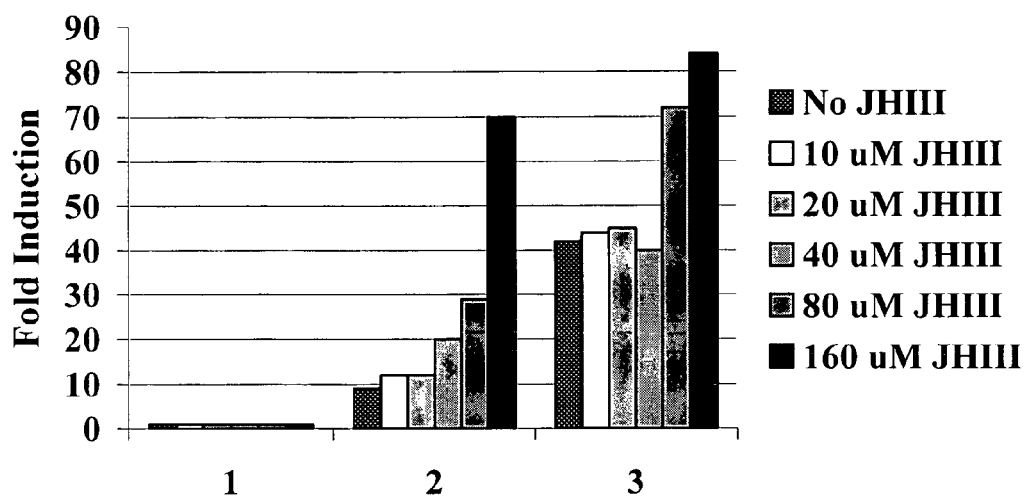
FIG. 2 shows the potentiating effects of juvenile hormone III (JHIII) dosage on the muristerone-A (murA) induced response mediated by a GRdEcR chimera and mouse RXR (mRXR) using a chloramphenical acetyltransferease (CAT) reporter construct (EcRE)$_5$-ΔMTV-CAT in mammalian Chinese Hamster Ovary (CHO) cells in accordance with example embodiments of the present invention. Sets 1, 2 and 3 correspond to 0, 0.01 and 0.1 μM murA.

Potentiation may be demonstrated with EcR and/or USP constructs that comprise chimeras having various portions of the protein derived from different species. For example, cells may be transfected with plasmids comprising a GRdEcR chimera that consists of the rat glucocorticoid receptor (GR) activation domain (A/B) attached to the Drosophila melanogaster (d or Dm) EcR DNA binding domain (DBD) (C/D) and ligand binding domain (LBD) (E), and a second plasmid comprising mouse RXR (mRXRα) or an insect USP. The response of transfected cells to the ecdysteroid, murA, may be measured using a $(EcRE)_5$-ΔMTV-CAT reporter plasmid that carries five tandem repeats of the hsp27 EcRE linked to the MTV promoter and the chloramphenicol acetyltransferase (CAT) gene. In an embodiment, using the assay system of the present invention, a response (an increase in CAT activity) is detected upon addition of the EcR ligand, muristerone A (murA), at doses as low as 0.1 μM (FIG. 2). For FIG. 2, sets 1, 2 and 3 correspond to 0 mur A, 0.01 μM murA and 0.1 μM murA. In these experiments, only amounts of hormone (e.g., muristerone A) that comprise submaximal levels of induction of EcR transcription are added to the assay system to detect signals from test compounds. Thus, in alternate embodiments, the dose of hormone may range from 0.001 μM to 5.0 μM, or from 0.005 μM to 0.5 μM, or from 0.01 μM to 0.1 μM.

As described above, the transfected cells may comprise mammalian cells. By using mammalian cells as the host, cofactors and transcription factors are present, but there may be minimal background activity due to endogenous ecdysone receptor and/or ligands. Any cell type that does not normally respond to ecdysteroids, but has the required transcription factors is a potentially suitable cell type for the assay.

Various combinations of the steroid activation pathway may be employed in the assay of the present invention. Thus, in one embodiment, the present invention comprises the use of specific receptor isotypes to evaluate potential insecticides. For example, in an embodiment, the assay may use an arthropod (e.g., insect) ecdysone receptor (EcR), an insect USP, and a suitable reporter gene construct (e.g., CAT or luciferase linked to a HRE specific to FXR or EcR). Alternatively, the assay may comprise using an insect EcR with a mammalian RXR, and a suitable reporter gene construct. In yet another embodiment, the assay may comprise use of an FXR construct in combination with a mammalian RXR construct. Or, the assay may comprise using FXR in combination with USP. Several non-limiting example embodiments for assay systems of the present invention are summarized in Table 1.

worm) USP. In another embodiment, the VP16 trans-activating domain may be linked to the *Drosophila* USP protein DBD and LBD to generate the contruct, VP16-DmUSPDBD-DmUSPLBD. Or, natural isoforms of Dm EcR with A/B domains A, B1 or B2 with the F domain deleted (Mouillet et al., 2001) may be used. Table 2 provides several non-limiting constructs that may be used with the methods and systems of the present invention, utilizing nomenclature that is standard in the art.

TABLE 1

| Ligand binding | Heterologue | Reporter construct | Hormone | Assay System | Application |
|---|---|---|---|---|---|
| GCdEcR | USP | (EcRE)$_5$-ΔMTV-LUC/CAT | Yes | Mammalian | Cell-based assay for insecticides |
| VP16-EcR | USP | (EcRE)$_5$-ΔMTV-LUC/CAT | Yes | Mammalian | Cell-based assay for insecticides |
| GCdEcR | RxR | (EcRE)$_5$-ΔMTV-LUC/CAT | Yes | Mammalian | Cell-based assay for insecticides |
| VP16EcR | RxR | (EcRE)$_5$-ΔMTV-LUC/CAT | Yes | Mammalian | Cell-based assay for insecticides |
| FXR | RxR | (EcRE)$_5$-ΔMTV-LUC | No | Mammalian | Environmental Screening |
| FXR | RxR | (EcRE)$_5$-ΔMTV-CAT/LUC | No | Mammalian | Cell based assay for insecticide |
| EcRA | USP | (EcRE)$_5$-ΔMTV-LUC/CAT | Yes | Mammalians | Cell-based assay for insecticides |
| EcRB1 | USP | (EcRE)$_5$-ΔMTV-LUC/CAT | Yes | Mammalians | Cell-based assay for insecticides |
| EcRB2 | USP | (EcRE)$_5$-ΔMTV-LUC/CAT | Yes | Mammalians | Cell-based assay for insecticides |

As indicated in Table 1, the DNA constructs used for the present invention may be chimeras. Nuclear receptors, such as EcR and FXR, may comprise three general domains structural domains: (1) a transcriptional activating domain—A/B; (2) a DNA binding (DBD)—C; and (3) a hinge (D) and ligand binding domain (LBD) (E) (FIG. 1). As used herein, the hinge (D) may be considered as part of the DBD (C) or the LBD (E) when describing various nuclear receptor protein constructs. Also, for some receptors, a C-terminal (F) domain may comprise trans-activation characteristics. For example, in one example embodiment, the EcR construct, GCdEcR, may comprise the human glucocorticoid receptor (GC) or (hGC) activating domain (e.g., A/B) and the *Drosophila* (d or Dm) EcR DNA binding domain (C) and the *Drosophila* hinge-ligand binding domain (D/E). Or, a VP16EcR construct comprising the VP16 activating domain (VP16) in combination with *Drosophila* EcR DBD and LBD domains (EcR) may be used. The assay may also comprise a construct, GGEc, comprising the human glucocorticoid receptor (G) trans-activating domain and DBD with the *Drosophila* EcR (Ec) LBD. The assay may also comprise a construct, GEcEc, comprising the human glucocorticoid receptor (G) activating domain and the *Drosophila* (Ec) DBD and LBD. In yet another embodiment, the assay may comprise a construct, GGF, comprising the human glucocorticoid receptor (G) activating domain and DBD with the FXR (F) LBD derived from vertebrate species (avian, rodent, human). In yet another embodiment, the assay comprises a construct, VP16CfUSP, comprising the VP16 activation domain directly linked to the LBD (i.e., D/E domains) of *Choristoneura fumerifana* (Cf) (spruce bud-

TABLE 2

Receptor Domain Composition of Plasmid Expression Vectors

| Construct | A/B -Trans-Activation | C - DNA Binding Domain (DBD) | D/E -Hinge - Ligand Binding Domain (LBD) |
|---|---|---|---|
| GCdEcR or GEcEc or GRdEcR* | hGR | Dm EcR | Dm EcR |
| GGEc | hGR | hGR | Dm EcR |
| GGF | hGR | hGR | FXR |
| VP16EcR | VP16 | Dm EcR | Dm EcR |
| VP16CfUSP | VP16 | — | Cf USP |
| VP16DmUSPDmUSP | VP16 | Dm USP | Dm USP |
| EcRA | EcRA | Dm EcR | Dm EcR |
| EcRB1 | EcRB1 | Dm EcR | Dm EcR |
| EcRB2 | EcRB2 | Dm EcR | Dm EcR |
| VP16USPF1 | VP16/DmA/B fusion | Dm USP | Dm USP |
| VP16USPF2 | VP16 | Dm USP | Dm USP |
| VP16USPF3 | VP16 | — | Dm USP |
| mRXRα | Mouse RXR | Mouse RXR | Mouse RXR |

*As used herein, glucocorticoid receptor elements may be designated as G, GC, or GR.

c. Potentiation

In an embodiment, juvenile hormones (JHs) can potentiate the effect of EcR ligands. For example, a GRdEcR chimera, that consists of the human glucocorticoid receptor activation domain (GR) attached to the *Drosophila melanogaster* (d) EcR DBD and LBD was cotransfected with mouse RXR (mRXR) into CHO cells. Using an (EcRE)$_5$-ΔMTV-CAT reporter gene, it was found that juvenile hormone III (JHIII) may potentiate the response of murA in a dose-dependent manner (using 20, 40, 80, and 160 μM JHIII) at submaximal ecdysteroid dosages (0.1 μM and 1 μM murA) (FIG. 2, sets 2 and 3, respectively). Also, although JHs can potentiate the effects of ecdysteroid ligands, JHIII may not increase the response above the maximal response seen with high concentrations of the ecdysteroid. Thus, using the assay described for FIG. 2, JHIII does not evoke a response that is greater than the maximal level induced by 10 µM murA.

The use of a mammalian cell-based assay system may allow for controlled addition of the components required for activity. Thus, in one embodiment, juvenile hormones do not interact with unbound EcR, but require addition of submaximal levels of exogenous hormone for activity. For example, despite the structural resemblance between the LBDs of EcR and the vertebrate FXR, which is highly responsive to JHIII alone (Forman et al., 1995), JHIII alone shows no effect on transcription mediated by the GRdEcR chimera with RXR (FIG. 2, set 1).

Using the assay system of the present invention, the interaction between various molecular components of the insect developmental pathway may be optimized. For example, ecdysteroid responsiveness and JHIII potentiation in EcR chimeras may depend, at least in part, upon the activating ligand being used. Ecdysteroid responsiveness and JHIII potentiation in EcR chimeras may also depend upon and the heterodimeric partner used in the assay system. In an embodiment, transfection of mammalian CHO cells with the VP16 activation domain linked to the DBD and LBD of *Drosophila melanogaster* (Dm or d) EcR, results in a sensitive and robust ecdysteroid response to muristerone A.

The assay of the present invention may also provide for the use of different EcR (or FXR) isoforms, either natural or generated by mutagenesis, as a means to evaluate the activity of various test compounds. In an embodiment, the isoforms may be specific to a particular insect species. Or, the isoforms may be generated by mutagenesis. As described above, the B isoforms may be functionally distinguished from the EcRA isoform, and recent studies have distinguished biological roles for B1 and B2. Also, the B2 N-terminal domain is shorter than the B1 N-terminal domain, and is capped with an amphipathic helix (Talbot et al., 1993; Hu et al, 2003, *Mol. Endocrinol.*, 17:716-731). Interestingly, alternative isoforms in the rat FXR also differ greatly in their ability to mediate ligand-dependent transcriptional activity (Zhang et al., 2003, *J. Biol. Chem.*, 278: 104-110).

As an example embodiment, to evaluate the activity of the various EcR isoforms, selected EcR isoforms, such as the three natural *Drosophila melanogaster* EcR isoforms, EcRA, EcRB1, and EcRB2, may be cotransfected into CHO cells with either USP or RXR expression plasmids such as, but not limited to, the VP16CfUSP and/or VP16CRXR fusion proteins. The different EcR isoforms (e.g., *Drosophila* A, B1, and B2) may be selected to differ at the N-terminal region of the protein, which is the part of the protein involved in dimerization of EcR with either USP, RXR or other appropriate partners. In an embodiment of the assay of the present invention, the isoforms (e.g., A, B1, and B2) may display unique expression profiles among each other and as compared to VP16dEcR/RXR (not shown).

The activity observed among the three EcR isoforms may depend, at least in part, upon the identity of the heterologous partner used. For example, when tested in the absence of hormone, the EcRB1/VP16CfUSP combination shows a relatively high level of ligand-independent transcription, with between 10 and 20-fold higher basal levels than other EcR constructs. Also, the EcRA isoform in combination with VP16CfUSP may also show a basal level of transcription that is 2 to 3 fold higher than the basal level of transcription obtained with EcRB2 isoform. In contrast, the basal activity of the EcRB2/VP16CfUSP dimer may be about the same as the basal activities produced by VP16dEcR/RXR and GREcR/RXR (not shown).

Figure 3:
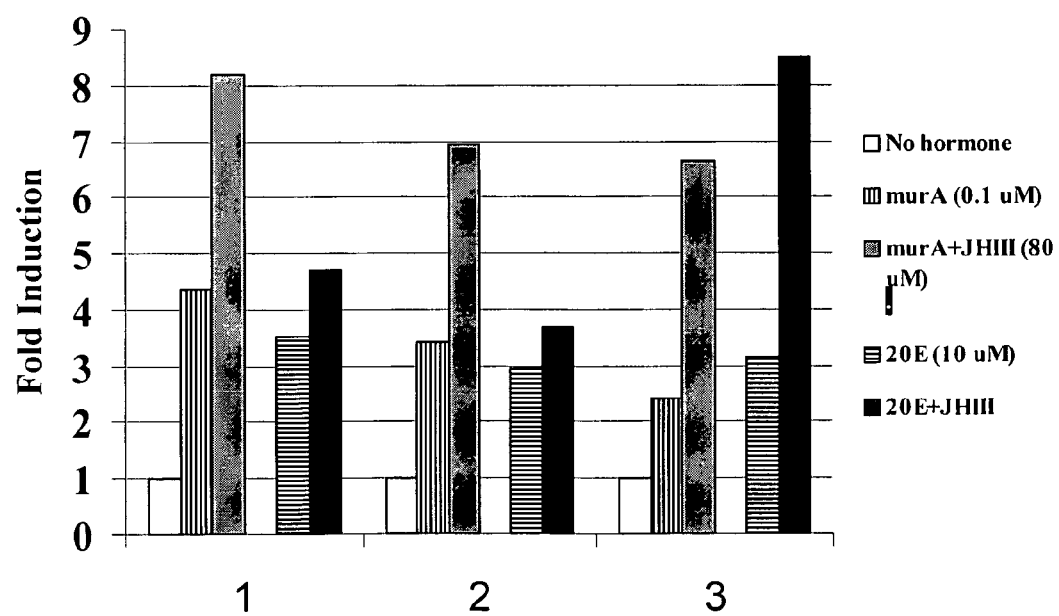
FIG. 3 shows the effects of murA, 20E, and JHIII on RLU activity induced by (EcRE)$_5$-ΔMTV-LUC in CHO cells cotransfected with *Drosophila* EcR isoforms and VP16CfUSP in accordance with example embodiments of the present invention where sets 1, 2, and 3 in the figure correspond to EcRA, EcRB1 and EcRB2, respectively.

In an embodiment, with VP16CfUSP, all three *Drosophila* isoforms (A, B1 and B2) may be induced by about 30-40 fold at 1 µM murA. Also in an embodiment, the response of all EcR isoforms in the presence of VP16CfUSP is potentiated by the presence of 80 µM JHIII in the presence of 0.1 µM murA. Data showing induction of isoforms A (set 1), B1 (set 2) and B2 (set 3) by murA, and potentiation by JHIII is shown in FIG. 3. In a further embodiment, the JH potentiation is dose-dependent, similar to the results seen with GrdEcR.

d. USP-Mediated Potentiation

Responsiveness of the natural EcR isoforms to the ecdysteroid 20E may require USP (rather than RXR) as a dimeric partner. In yet a further embodiment, among the three isoforms (EcRA, EcRB1, and EcRB2), JHIII potentiation in the presence of 20E may occur primarily with EcRB2 isoform and USP. For example, at a dosage of 10 µM 20E, all three *Drosophila* EcR isoforms and VP16CfUSP generate a consistent and discernible transcriptional response. Only the EcRB2/VP16CfUSP dimer (FIG. 3, set 3) is potentiated significantly by the additional presence of JHIII, however. That only the B2 EcR isoform is potentiated by JHIII in the presence of 20E indicates that activation by JHIII may depend upon both the N-terminal domain of EcR and the activating ecdysteroid.

Figure 4:
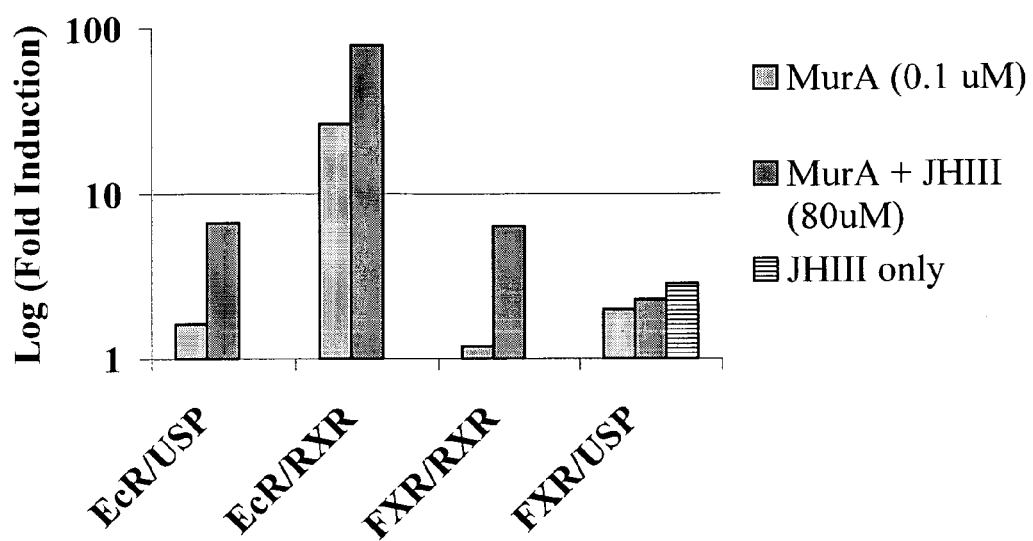
FIG. 4 shows the response of various combinations of nuclear receptors and their binding partners to muristerone A and JHIII in CHO cells in accordance with example embodiments of the present invention, where EcR refers to VP16dEcR, USP refers to VP16CfUSP, and FXR and RXR refer to natural mammalian forms.

Specific combinations of the EcR N-terminal domain and the heterodimeric partner (e.g. VP16 and RXR, B2 and USP) may therefore result in a functional receptor that is capable of showing an ecdysteroid response and/or JHIII potentiation. Also, in one embodiment of the assay system, the potentiation by JHs is not due to the activation of RXR by either JHIII or a JHIII metabolite, as JHIII by itself shows no potentiation of transcriptional activity. For example, in selected embodiments of the present invention, combinations of EcR/USP, EcR/RXR, and FXR/RXR show a response to murA that may be potentiated by JH (FIG. 4). In contrast, the combination of FXR with USP may not respond to JHIII. Thus, whereas the FXR activator JHIII can potentiate the transcriptional response of EcR induced by ecdysteroids, it appears that in at least some embodiments, the JHIII response exhibited by FXR may require RXR, and not USP, as a heterodimeric partner. Thus, in at least some systems, USP and RXR may not be interchangeable. Also, the presence of a ligand-bound EcR may be a prerequisite for observing the potentiative effects of JHIII on EcR. Assays using the various EcR forms indicate that multiple factors may influence receptor activity, including the activating ecdysteroid, the N-terminal domain of EcR, and the heterodimeric partner.

A summary of ecdysteroid responsiveness and JHIII potentiation among various combinations of EcR with either RXR or USP proteins (Table 3) shows that murA may exhibit activity with a wider range of ecdysteroid receptor heterodimers and may be more potent than 20E. Further, the EcR combination may influence responsiveness. For example, all three isoforms (EcRA, EcRB1, and EcRB2) may be potentiated by JHIII when murA is the activating ligand. In contrast, for 20E, only the B2/USP may be substantially potentiated by JHIII. Also, in an embodiment, of the three isoforms, only EcRB1 acts with RXR. In contrast to the activity seen with murA, the three isoforms may respond to 20E only in conjunction with their natural partner, USP. Thus, it appears that 20E responsiveness may involve a compatibility between the N-terminal domain of EcR and the heterodimeric partner. In one embodiment, the high level of B1 basal activity may relate to a cell-specific aspect of CHO cultures, as this effect has not been seen in HeLa cells. The selectivity of the 20E responsiveness may be further substantiated by the ability of the VP16dEcR/VP16CfUSP combination to respond only to murA, but not to 20E.

TABLE 3

A summary of ecdysteroid responsiveness and JHIII potentiation among various cominations of EcR with either RXR or USP proteins

| Ecdysone Receptor Description | MurA RXR USP | | MurA + JHIII RXR USP | | 20E RXR USP | | 20E + JHIII RXR USP | |
|---|---|---|---|---|---|---|---|---|
| GRdEcR  | +  | n.d | +  | n.d | −  | n.d. | −  | n.d. |
| VP16dEcR | ++ | +   | +  | +   | +  | −    | −  | −    |
| EcRA    | −  | +   | −  | +   | −  | +    | −  | −    |
| EcRB1   | +  | +   | +  | +   | −  | +    | −  | −    |
| EcRB2   | −  | +   | −  | +   | −  | +    | −  | +    |

Proteins are described in Examples 1 and 2. (+) designates a change in transcriptional level that exceeds 2.5-fold, (++) indicates a response at a lower dosage than other EcR forms. Responses are based on dosages of 0.1 μM murA, 10 μM 20E, and 80 μM JHIII. For murA and 20E, (+) indicates inducibility; for columns involving JHIII, (+) indicates observed potentiation that exceeds 2-fold above the levels observed with ecdysteroid alone.

e. Activating Hormones

The activating ecdysteroid may also determine the ability of JHIII and other modulators to potentiate a response in other EcR dimers. For instance, the VP16dEcR/RXR combination is generally responsive to both 20E and murA; but when 20E is used, JHIII may not be capable of potentiating the response, whereas JHIII strongly potentiates the murA response.

The EcR modulator may be one of several compounds known to interact with EcR and its heterologous binding partner. In one embodiment, the EcR modulator may bind to the ligand binding domain (LBD) of EcR. Or, the EcR modulator may bind to other portions of the EcR polypeptide. For example, the EcR modulator may comprise an ecdysteroid. Thus, in an embodiment, the EcR modulator may comprise muristerone A (murA). Alternatively, the EcR modulator may comprise or 20-hydroxyecdysone (20E). In additional and/or alternative embodiments, the modulator may comprise ponasterone A, 3-dehydro-20-hydroxyecdysone, ecdysone, makisterone A, nonsteroidal agonist including RH5849, RH5992, RH2485, and the like. Or other modulators as described herein may be used. The modulator may be added to the assay system as a polypeptide. In another embodiment, the EcR modulator may be transfected into the cell as a DNA construct.

In an embodiment, EcR, bound to its cognate ligand, may acquire a conformation that allows further activation by JHIII or other potentiating agents either directly or via an indirect interaction. Also, the amount of ligand-bound EcR may be limiting factor in the cell-based assay of the present invention. For example, while the amount of potentiation may remain constant over a range of submaximal murA doses, the absolute transcriptional activity attributable to a fixed potentiator dose may increase as ecdysteroid molarity increases, indicating that the number of ligand-activated EcR proteins may be a rate-limiting factor.

The mechanism of potentiation for EcR/USP may be different from effects of the effects of potentiators on RXR. RXR may be activated through its LBD. For example, methoprene acid with the retinoic acid receptor (RAR) generates a response to the ligand through a direct repeat element (Harmon et al., 1995). Known RXR ligands may also increase the responsiveness of VP16dEcR to murA via the hsp27 response element (Saez et al., 2000, Proc. Natl. Acad. Sci. USA, 97:14512-14517) to supra-maximal levels. In contrast, potentiation of EcR by JHIII may occur at a submaximal hormone response through already activated EcR molecules. Also, RXR ligands may activate the VP16EcR/RXR complex even when ecdysteroids are not bound to the EcR partner (Saez et al., 2000). By contrast, the effects of JHIII in the assay of the present invention may require the simultaneous presence of ecdysteroids for any response to be observed.

f. Species-Specific USP and EcR Polypeptide Constructs

Embodiments of the present invention comprise nucleic acid constructs comprising specific regions of the USP protein. For example, to provide a system capable of inducing ecdysteroid-dependent transcription in mammalian cells, the N-terminal domain of an insect USP may be replaced with the mammalian VP16 activation domain. With this form of mammalian-insect hybrid USP, a mammalian cellular system that is devoid of basal activity may be responsive to murA.

Figure 5B:
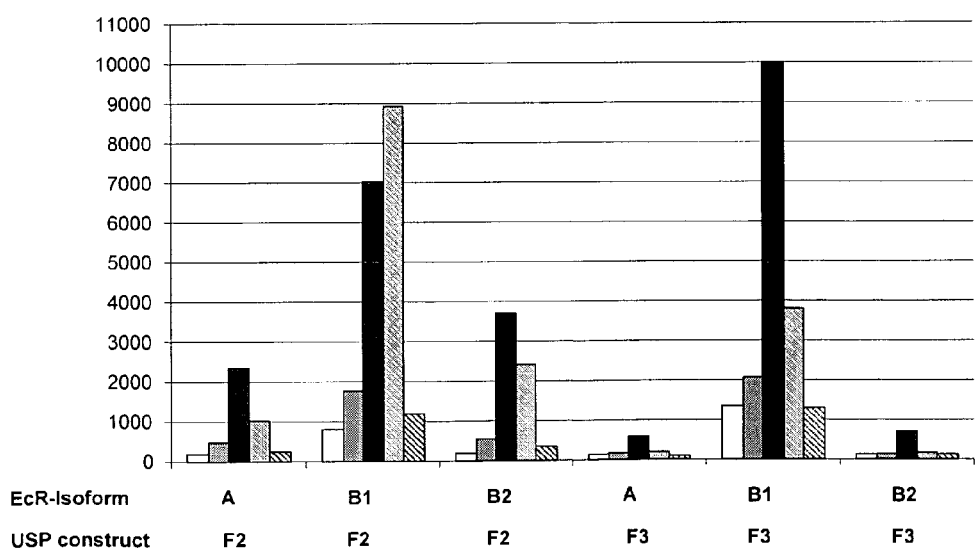
FIG. 5 shows a schematic representation of the structure of three *Drosophila melanogaster* isoforms for EcR and various USP constructs used in a mammalian cell assay system in accordance with embodiments of the present invention. 5A shows a diagrammatic representation of the DNA constructs used; 5B shows transcriptional activity of three DmEcR isoforms (A, B1, and B2) and two VP16-DmUSP (F2 and F3) fusion proteins, as indicated by normalized luciferase activity in accordance with an embodiment of the present invention. In 5B, from left to right, open and unshaded boxes indicates activity after 24 hours in the absence of hormone. Gray and dark boxes indicate effects of 0.1 uM murA and 1.0 uM murA, respectively. Hatched gray boxes indicates effects of 0.1 uM murA and 80 uM JHIII, and hatched, open boxes indicate effects of JHIII alone.
Figure 5A:
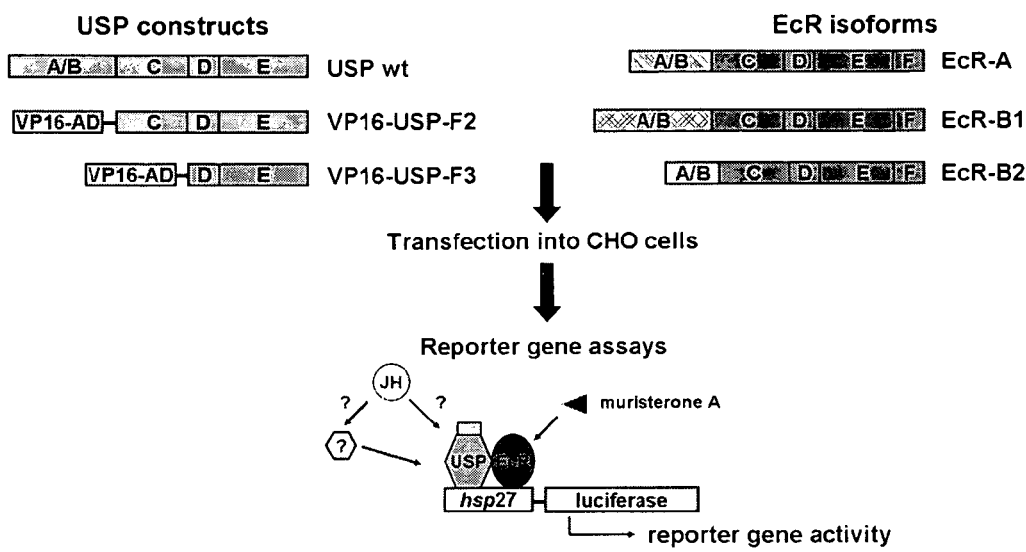

For example, in one embodiment, the present invention may comprise a nucleic acid molecule encoding an Ultraspiracle protein (USP) comprising a mammalian transactivation (A/B) region, and an insect DNA binding domain, hinge region, and the ligand binding domain (LBD). For example, in one embodiment, the dUSP-F1 fusion protein includes the codons for six amino acids (aa 98-103) that are conserved among all insect USP sequences along with the DBD, hinge region, and LBD of DmUSP (aa 104-507) (FIG. 5A).

In another embodiment, the present invention may comprise a nucleic acid molecule encoding a portion of a Drosophila Ultraspiracle protein comprising the DNA binding domain, the hinge region, and the ligand binding domain of USP. For example, in one embodiment, the dUSP-F2 fusion protein includes the codons for the DBD, hinge region, and LBD of DmUSP (aa 104-507). Thus, the dUSP-F2 construct may comprise a very similar sequence as dUSP-F1, except that these six conserved amino acids are not included (FIG. 5A). In an embodiment, the F2 fusion protein exhibits about the same levels of inducibility in conjunction with the EcR isoforms, suggesting that these conserved regions may have minimal effect upon hsp27-mediated transcription.

In another embodiment, the present invention may comprise a nucleic acid molecule encoding a portion of a Drosophila Ultraspiracle protein comprising the hinge region, and the ligand binding domain of USP. For example, in one embodiment, the dUSP-F3 fusion protein carries only the hinge region and LBD of USP (FIG. 5A). The dUSP-F3 fusion protein may be analogous to a Choristoneura fumiferana (Cf) USP fusion protein described previously (Henrich et al, 2003).

For each of the constructs shown as USP-F1, USP-F2 and USP-F3, a mammalian A/B domain may be used.

It has been shown that in vivo mutations of the DmUSP DBD do not appear to reduce induction of ecdysteroid-responsive genes. However, the same mutations may derepress specific target genes, indicating that the DmUSP DBD may play a repressive role for some genes (Shubiger et al.). Based on these findings, it might be expected that the removal of the DBD would cause a higher level of induction. Surprisingly, the activity seen with dUSPF2 (+DBD) may be similar to that reported previously with CfUSPF3, which lacks a DBD (DBD−). For example, a VP16-dUSPF2 which includes the DNA binding domain (i.e., a VP16 A/B linked to a Drosophilia C/D/E region of USP) may actually confer greater responsiveness to murA than VP16-dUSPF3 which lacks the DNA binding domain (i.e., a VP16 A/B linked to a Drosophilia D/E region of USP) for the A and B2 isoforms of a Drosophila EcR. In contrast, the B1 isoform shows an elevated responsiveness to murA in the presence of dUSP-F3 (FIGS. 5A and 5B).

In an embodiment, the EcR isoform may be important for potentiation. For example, the B1 isoform (in conjunction with dUSPF3 and dUSPF2) shows basal and murA-induced levels of transcription that are 5-10-fold higher than those of the other two isoforms (FIG. 5B). As measured by Western blotting, B1 generated the weakest immunostaining signal when extracts were tested by Western blotting (not shown) indicating that. In an embodiment, when paired with dUSPF2, the A isoform may be the least responsive to murA treatment, while B1 and B2 may show about equivalent potentiation of murA activation by JHIII (FIG. 5B) or other potentiators (e.g., JHI; data not shown). These differences may not be attributable to significant differences in ligand-binding affinity since all three EcR isoforms show virtually the same level of ligand affinity (data not shown).

g. Species-Specific Hormones and Insecticides

In one embodiment, the present invention utilizes various EcR isoforms and/or species-specific polypeptides for the identification of compounds that may function as either stage-specific and/or species specific modulators of insect growth. At least three isoforms of EcR exist in *Drosophila melanogaster*: EcRA, EcRB1, and EcRB2. The three isoforms differ in the amount of N-terminal transactivating sequences (FIG. 5A). The three *D. melanogaster* EcR isoforms may show different transcriptional and inductive capabilities in a heterologous cell culture system (Mouillet et al, 2001; Henrich et al, 2003). The three *D. melanogaster* EcR isoforms also show varying levels of potentiated transcriptional activity with the addition of the juvenoid JHIII. Interestingly, in at least some embodiments, juvenoids exert no effect on EcR activity in the absence of a steroid.

In one embodiment, a mammalian cell-based environment is used for the methods and systems of the present invention. While EcR/mammalian fusion proteins are responsive to ecdysteroids, none of the natural *Drosophila* isoforms induces ligand-dependent transcription when partnered with RXR, the mammalian orthologue of USP. Also, the level of RXR in mammalian CHO cells is low, so that virtually any response to ecdysteroids depends upon the introduction of both EcR isoforms and USP.

Figure 6:
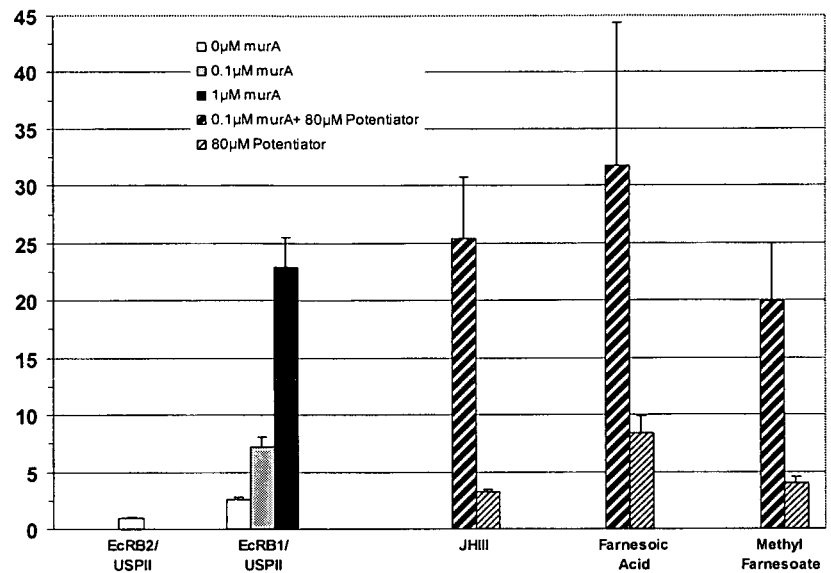
FIG. 6 shows potentiation of murA stimulation of EcRB1/DmUSPF2 complexes by JHIII and precursors farnesoic acid and methyl farnesoate in accordance with embodiments of the present invention.

Thus, as shown in FIG. 6, when cells are transfected with a *Drosophila* EcRB1 and a *Drosophila* USPF2 protein the complex may be stimulated by murA (0.1 µM and 1.0 µM). Additionally, the effect of the hormone (0.1 µM murA) is increased by the potential insecticide compounds JHIII and precursors farnesoic acid and methyl farnesoate. The mevalonate pathway may provide an indicator of nutritional status in feeding larvae. Also, in an embodiment, JHIII and/or its precursors may function as stage-specific insecticides by decreasing the amount of ecdysteroid need to induce molting.

Figure 7:
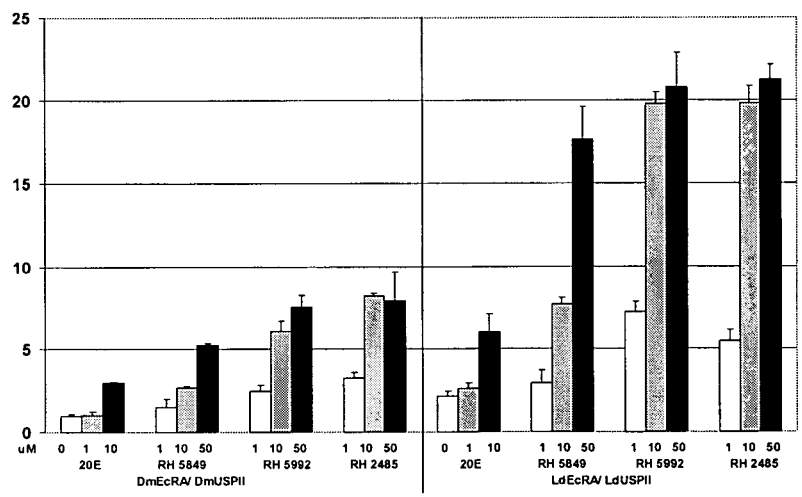
FIG. 7 shows that the EcRA isoform from *Leptinotarsa decemlineata* (Ld) (Colorado potato beetle) displays a much stronger response to diacylhydrazine insecticides than the equivalent EcRA isoform from *Drosophila melanogaster* (Dm) in accordance with embodiments of the present invention.

In an embodiment, the species specificity of the EcR isoform and/or the USP protein may be used to identify species specific insecticides. For example, in an embodiment, the EcRA isoform and USP protein from *Leptinotarsa decemlineata* (Colorado potato beetle) together display a much stronger response to diacylhydrazine insecticides than the equivalent EcRA isoform and USP from *Drosophila melanogaster*. For example, in FIG. 7, the effects of the hormone 20E, as well as insecticides RH5849, RH5992, and RH2485 are tested in a mammalian cells transfected with either: (i) *Drosophila* (Dm) EcRA and *Drosophila* (Dm) USPII (left panel) or (ii) *Leptinotarsa* (Ld) EcRA and *Leptinotarsa* (Ld) USPF2 (i.e., USPII) (left panel). Interestingly, the profile displayed in FIG. 7 is consistent with the reported differences in susceptibility of these species to the toxic effects of the compounds.

Figure 8:
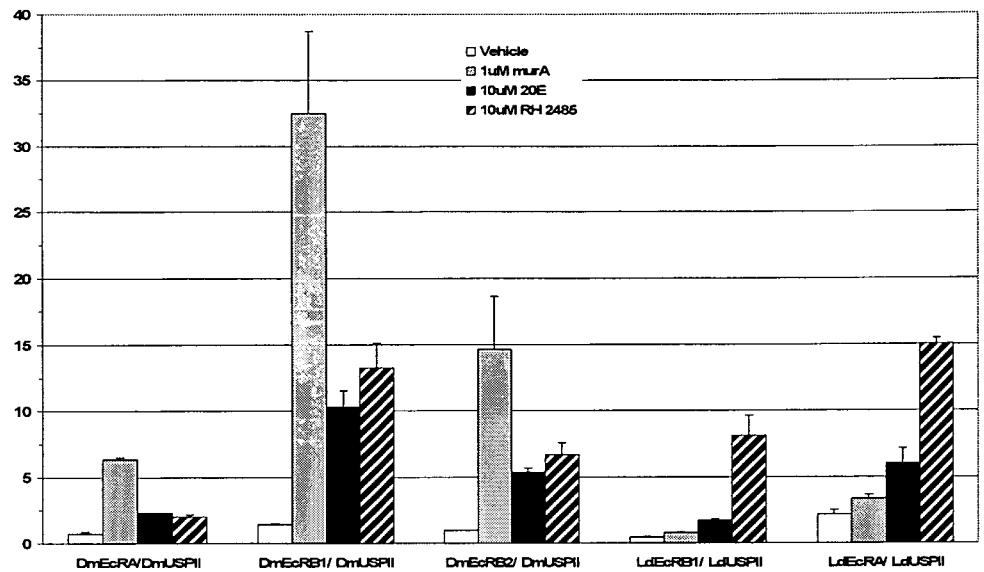
FIG. 8 shows that the EcR isoforms of *Leptinotarsa decemlineata* (Ld) and *Drosophila melanogaster* (Dm) display different profiles of responses to a variety of ecdysteroid agonists (muristerone A, 20-hydroxyecdysone, and RH2485).

In an embodiment, the EcR isoform may provide specificity with respect to activation by ecdysteroids or other agonists. For example, in an embodiment, the EcR isoforms of *Leptinotarsa decemlineata* and *Drosophila melangaster* display dramatically different responses to a variety of ecdysteroid agonists: muristerone A (murA); 20-hyroxyecdysone (20E); and RH2485. Thus, as shown in FIG. 8, *Drosophila melangaster* EcR isoforms display much greater stimulation by murA, than either 20E or RH 2485. Also, it can be seen that the B1 EcR isoform has a higher level of basal and induced activity. In contrast, *Leptinotarsa decemlineata* EcR displays a much greater stimulation by RH2485, than by murA or 20E. The results of the assay coincide with the effects of these compounds in vivo, in that *Leptinotarsa* is found to display greater sensitivity to diacylhydrazine insecticides than *Drosophila*. Interestingly, *Leptinotarsa* displays a different profile with respect to the EcRA and EcRB1 isoforms, in that the Ld EcRA displays greater basal and induced activities than the EcRB1.

Figure 9:
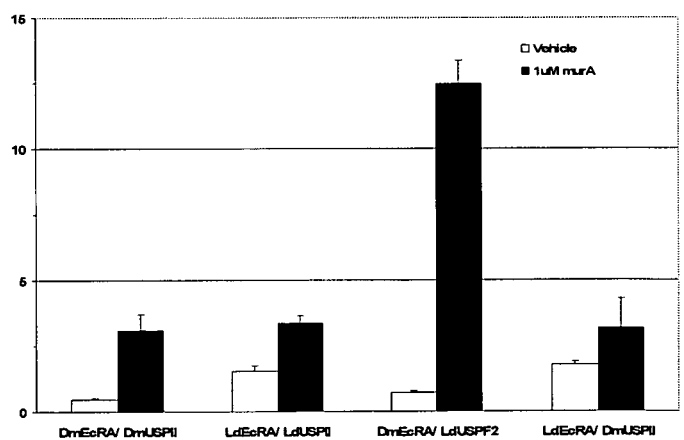
FIG. 9 shows that *Drosophila melanogaster* (Dm) and *Leptinotarsa decemlineata* (Ld) USP display different modulatory activities with EcR in accordance with embodiments of the present invention.

In an embodiment, the USP protein may provide specificity with respect to activation by ecdysteroids or other agonists. For example, in an embodiment, the USP from *Leptinotarsa decemlineata* and *Drosophila melangaster* display dramatically different responses to stimulation by ecdysteroids or other agonists. Thus, as shown in FIG. 9, the USP from *Leptinotarsa decemlineata* (LdUSPF2) and *Drosophila melangaster* (DmUSPII) do not necessarily perform identically as heterodimeric partners for EcR. For example, the LdUSPF2 appears to provide a much higher level of stimulation by murA when paired with DmEcRA. Thus, in an embodiment USP can play a species-specific role in determining the level of transcriptional activity as well as the preferred EcR binding partner. As used herein, the nomenclature is such that USPF1 is equivalent to USPI; USPF2 is equivalent to the USPII; and USPF3 is equivalent to USPIII.

h. Effects of Site Directed Mutations on Isoform Function

Other embodiments of the present invention comprise mutant EcR proteins produced by site-directed mutagenesis. For example, in certain embodiments, the methods and systems of the present invention may comprise a nucleic acid molecule that encodes a portion of the EcR protein comprising a mutation at the residue corresponding to lysine (L) 497 of the native *Drosophila melanogaster* EcR protein, wherein the lysine is changed to a glutamate (E) (i.e., K497E). In other embodiments, the methods and systems of the present invention may comprise a nucleic acid molecule that encodes a portion of the EcR protein comprises a mutation at the residue corresponding to methionine (M) 504 of the native *Drosophila melanogaster* EcR protein, wherein the methionine is changed to an arginine (R) (i.e., M504R). In yet other embodiments, the methods and systems of the present invention may comprise a nucleic acid molecule that encodes a portion of the EcR protein comprises a mutation at the residue corresponding to alanine (A) 483 of the native *Drosophila melanogaster* EcR protein, wherein the alanine is changed to a threonine (T) (i.e., A483T).

The mutant constructs of the present invention may provide the opportunity to assess the effect of specific structural changes upon receptor function, and to determine the mechanistic basis for the effects of exogenous agents on particular isoforms. Earlier studies characterized the physical interaction of the DmEcR and DmUSP LBDs by testing their ability to heterodimerize in a yeast two-hybrid system. These studies demonstrated that many mutations nonspecifically impair a variety of receptor functions, such as heterodimerization, ligand-binding, DNA-binding, and trans-activation. This category includes several missense mutations of the EcR LBD that correspond to known lethal in vivo mutations (Bender et al, 1997; Bergman et al, 2004, *Biochem. J.*, 378:779-784). A fraction of mutations tested in the two-hybrid system, however, impair specific receptor characteristics with relatively little effect on others. A few of these mutational sites were tested in each of the three EcR isoforms to determine whether the substitutions evoked the same effect in whole receptors as they did in analogous yeast two-hybrid fusion proteins (Grebe et al, 2003, *Biol. Chem.*, 384:93-104; Bergman et al, 2004). Further, these common region mutations were tested in each isoform to explore the possibility that a common region mutation can disrupt an isoform-specific function.

i. The K497E and A483T Mutations

In an embodiment, the methods and systems of the present invention comprises a nucleic acid molecule that encodes an EcR protein comprising a mutation at the residue corresponding to lysine (K) 497 of the native *Drosophila melanogaster* EcR protein, wherein the lysine is changed to a glutamate (E). In another embodiment, the methods and systems of the present invention comprises a nucleic acid molecule that encodes an EcR protein comprising a mutation at the residue corresponding to alanine (A) 483 of the native *Drosophila melanogaster* EcR protein, wherein the alanine is changed to a threonine (T).

The K497 residue lies in helix 4 of EcR and aligns with a consensus cofactor binding site in nuclear receptors. The site has also been implicated in the formation of a salt-bridge with helix 12 of EcR to mediate ligand-dependent transcriptional activity (Wurtz et al, 1995a, *Nat. Struct. Biol.*, 3:87-94; Wurtz et al, 1995b, *Nat. Struct. Biol.*, 3:206). Two different substitutions of this residue, K497A (lysine mutated to alanine) and K497E, may provide an elevated level of ligand-independent transcriptional activity in the yeast two-hybrid system (Bergman et al, 2004). The similar effects caused by the two mutations of K497 strongly suggests that a loss of function associated with the substitution of this residue results in "constitutive" EcR/USP activity. Also, it has been found that ecdysteroid affinity in the mutant fusion protein is strongly reduced (Grebe et al, 2003).

Figure 10:
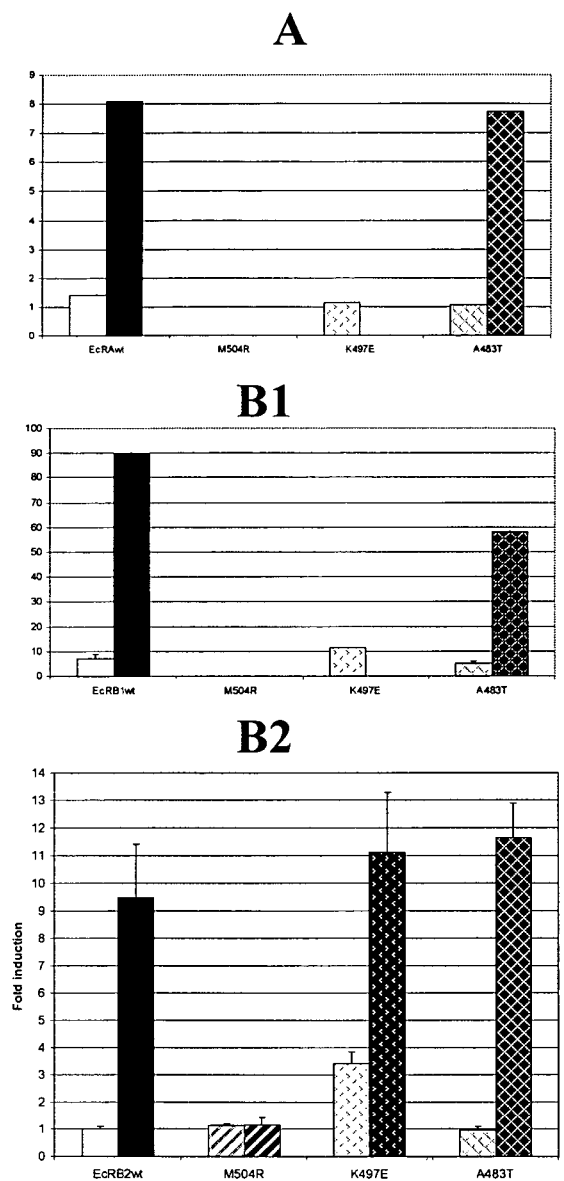
FIG. 10 shows effects of three site-directed mutations (M504R; K497E; A483T) on basal and murA-induced levels of transcription on three EcR isoforms of *D. melanogaster* in accordance with embodiments of the present invention. For each pair, light boxes (left) indicate transcriptional levels in the absence of murA, and darkened boxes (right) indicate transcriptional activity in the presence of 1 μM murA. RLU activity for individual data points were transformed relative to basal levels obtained for EcRB2 in the absence of murA, assigned a mean value of 1.0. All standard deviations based on a sample size of 3 using transformed data.

When the K497E mutation was tested in the three DmEcR isoforms with dUSPF2, an elevated level of ligand-independent (basal) transcription was observed for each isoform (FIG. 10) (light stippled bars). However, the B2 isoform was most substantially affected by the mutation as basal rates of transcription were elevated by almost four-fold above normal (FIG. 10). The substantially elevated transcription associated with B2-K497E does not appear to act via a co-repressor binding site. Thus, as shown in FIG. 10, elevated transcription mimicking that of B2-K497E may not be found in any of the isoforms carrying the A483T mutation, which disrupts a site responsible by which a physical interaction occurs between EcR and the corepressor, SMRTER.

Figure 11:
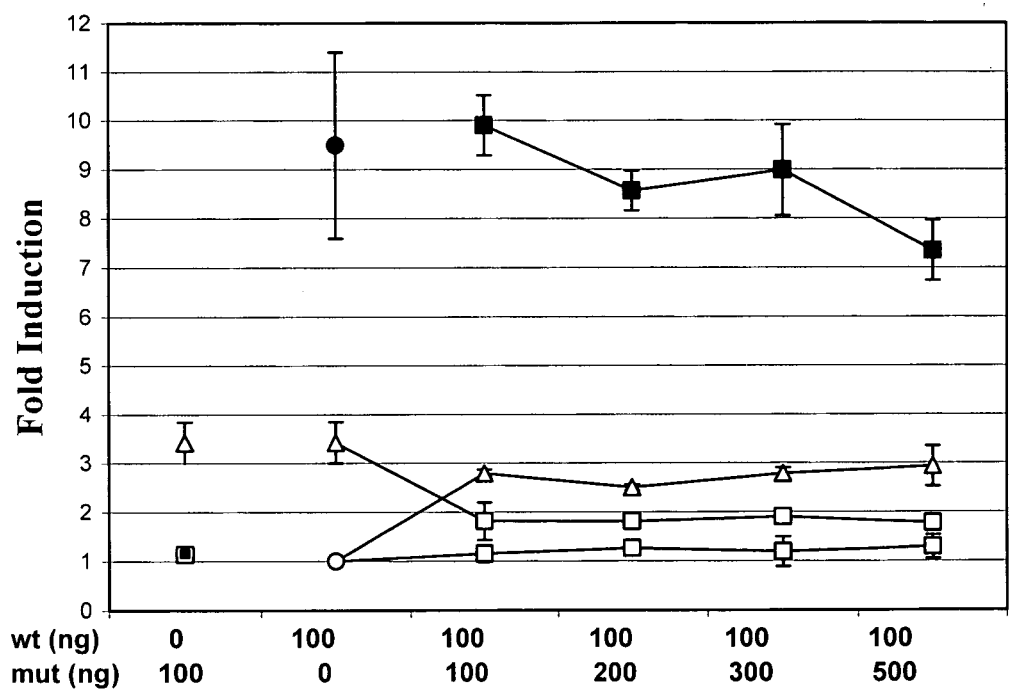
FIG. 11 shows transcription levels resulting from transfection with 100 ng of wild-type EcR-B2 and varying amounts of selected mutant EcR-B2 isoforms in the absence and presence of 1 μM murA in accordance with embodiments of the present invention. Open symbols indicate data points from incubations in the absence of murA, and solid symbols indicate incubations with 1 μM murA. Circles indicate wild-type EcR-B2 alone. Squares indicate mutant amounts of EcR-B2 (M504R) in the absence and presence of murA. Spotted square represents overlap between EcRB2 (M504R) with and without 1 μM murA. Triangles indicate mutant amounts of EcR-B2 (K497E) in the absence of hormone. EcR-B2 (K497E) was used as a proxy for wild-type EcR-B2 to compete with EcR-B2 M504R, since the K497E mutation confers a high basal level of activity allowing for competition analysis to be performed. All data points based upon three replicates. Points for which error bars are not apparent represent variations too small for graphing.

A competition assay was devised by which increasing titers of B2-K497E (0 to 500 ng) were transfected along with a fixed amount of the wild-type B2 isoform (100 ng) and transcription observed in the absence and presence of murA (FIG. 11). A gradual increase in transcriptional levels with increasing levels of B2-K497E (triangles) presumably reflects the competition of mutant and wild-type B2 for a rate-limiting amount of dUSPF2. The dose dependence of the effect further indicates that the elevated transcriptional rates seen in B2-K497E do not result from a preferential (abnormally high) affinity of the mutant B2 isoform for DmUSP in the absence of stabilizing ecdysteroids.

Figure 12:
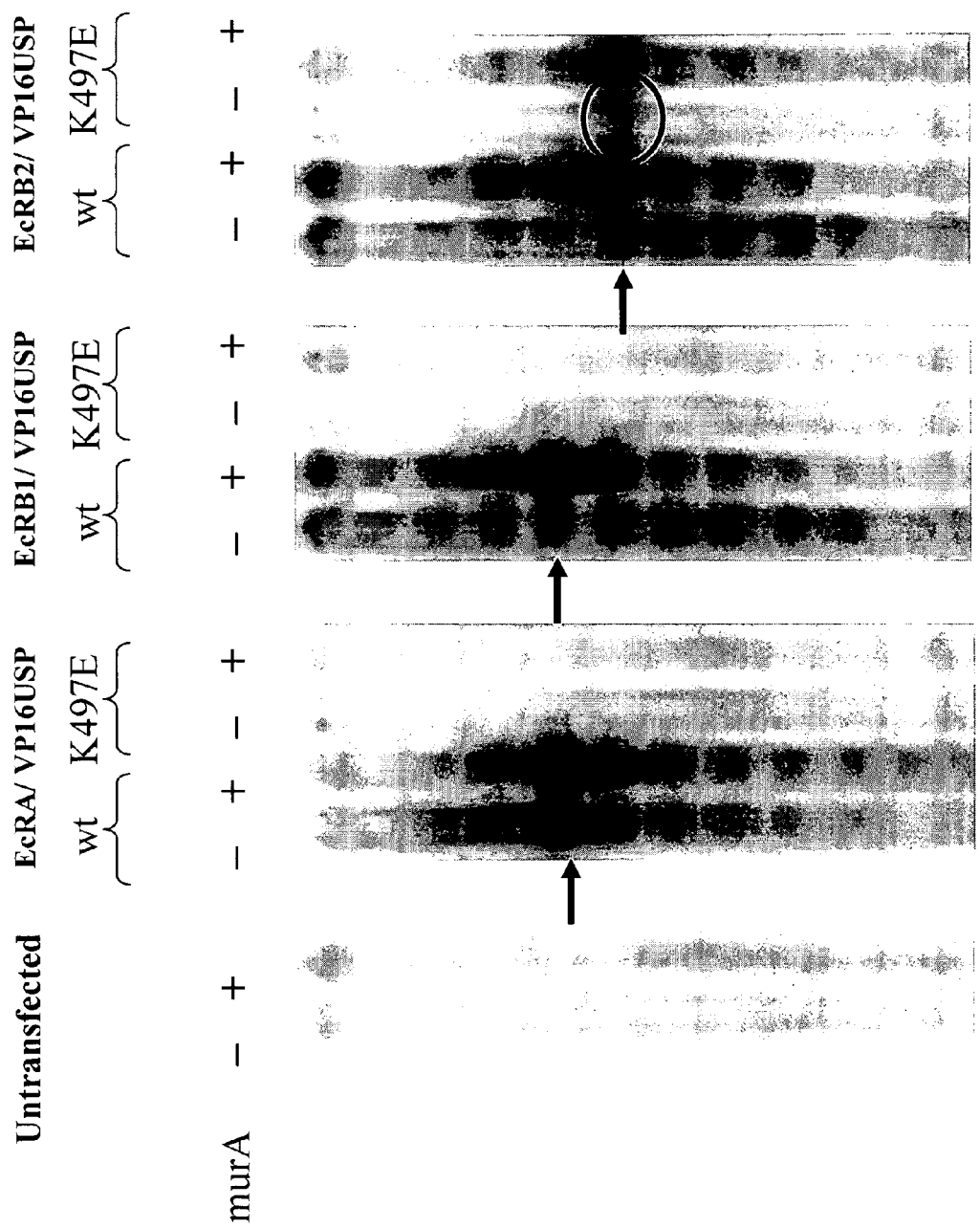
FIG. 12 shows an electrophoretic mobility shift assay (EMSA) measuring binding of EcR wild-type and mutated K497E isoforms in the absence and presence of hormone (murA) in accordance with embodiments of the present invention.

The three K497E isoforms were also tested by an electrophoretic mobility shift assay (EMSA) to determine whether the elevation of transcription is associated with a higher affinity for the hsp27 response element. In an embodiment, the K497E-B2 isoform has a stronger affinity for the hsp27 EcRE in the absence of hormone than the equivalent mutants of A or B1 (FIG. 12; circled region of the gel). Interestingly, EcRB2 is the only isoform that is potentiated by 20-hydroxyecdysone and JHIII; such potentiation is only seen with USP (i.e., not with RXR) (Henrich et al., 2002). While the affinity of these two mutated isoforms for hsp27 is higher in the presence of murA, both showed little affinity for the element in the absence of hormone.

ii. The M504R Mutation

In an embodiment, the methods and systems of the present invention comprises a nucleic acid molecule that encodes an EcR protein comprising a mutation at the residue corresponding to methione (M) 504 of the native *Drosophila melanogaster* EcR protein, wherein the methionine is changed to an arginine (R). Ecdysteroids stabilize the EcR/USP heterodimer which in turn, recognizes promoter elements to regulate transcription. It follows that a receptor that is unable to bind to hormone may also be unable to be stabilized by the hormone, and ultimately, may fail to elevate transcription in the presence of the hormone. Based on alignments of the nuclear receptor superfamily, a mutation was made at a consensus site for ligand-binding (M504) in helix 5 of DmEcR (Wurtz et al, 1995a, b), though this site does not correspond to any that are predicted to contact ecdysteroids in the *Heliothis* EcR model (Billas et al, 2003, *Nature*, 426:91-96). When tested for heterodimerization, the mutant EcR showed normal dimerization affinity for USP in the absence of hormone as measured by a two-hybrid assay, but the elevated rate of heterodimerization associated with ligand-binding is abolished, and in fact, ligand-binding is also eliminated in this mutant (Grebe et al, 2003).

Consistent with those two-hybrid results, basal levels of transcription for the construct of the present invention were unaffected by the mutation in any of the three natural EcR isoforms whereas murA-induced rates of transcription were almost completely eliminated (FIG. 10). In the absence of hormone, B2-M504R competes with K497E (which in turn, competes with wild-type EcR and served as a proxy for wild-type dimerization). In the absence of hormone, transfection with equal amounts of plasmid encoding K497E (triangles) and M504R (squares) mutant EcR-B2 (100 ng of each) reduced the abnormally high level of transcriptional activity caused by the K497E mutant (FIG. 11). By contrast, the M504R mutant receptor failed to displace wild-type receptor in the presence of murA even when a five-fold excess of mutant-encoding plasmid was transfected into cells (500 ng vs 100 ng of wild-type plasmid). This may suggest that the ligand-bound, wild-type EcR-B2 has an intrinsically higher affinity for USP than the M504R receptor, which is incapable of ligand-activation. This result is also consistent with the supposition that an ecdysteroid stabilizes the EcR/USP heterodimer by increasing the mutual affinity of EcR and USP.

The constructs of the present invention show that the native EcR isoforms possess both shared and unique characteristics that may be important for mediating ecdysteroid-mediated developmental processes. Also, the constructs of the present invention show that the native EcR isoforms possess both shared and unique results in the presence of compound that can modulate the natural hormonal response important for mediating ecdysteroid-mediated developmental processes. Thus, in an embodiment, the differences observed in the molecular action of the three EcR isoforms, when tested in cell culture with the canonical hsp27 EcRE, indicate that the three isoforms show discernibly diverse capabilities in the absence and presence of ecdysteroids. For instance, the relatively active B I is the only EcR isoform capable of rescuing polytene puffing in the *Drosophila* larval salivary gland (Bender et al, 1997). The elevated transcriptional activity of B1 observed in the presence of ecdysteroid may signify a high quantitative level of transcriptional induction that is essential for evoking puffing, which itself represents a robust response. B2 is the most effective isoform for rescuing embryonic lethality in EcR-null mutations through the larval stages, a developmental phase during which both juvenile hormone and ecdysteroid titers are periodically elevated. This isoform was also the most responsive to JH potentiation, and the only isoform that can be potentiated by JH when 20E is used as an agonist (Henrich et al, 2003).

In another embodiment, isoform-specific function may be further revealed by the effects of mutations of the EcR protein. For example, in one embodiment, an effect of the B2-K497E mutation is that ligand-independent affinity of the B2-K497E mutant for the hsp27 EcRE may be elevated (FIG. 12). While the possibility that this mutation has destroyed a cofactor binding site cannot be formally ruled out, there appears to be no difference in the size of the mutant and wild-type B2 complex seen on an EMSA, as would be expected if a cofactor interaction were involved. Moreover, if a cofactor is involved in this mutant-induced effect, it should occur in both mammalian (cell culture) and yeast (two hybrid) cells. Cell culture competition experiments (not shown) have also shown that K497E has about normal dimerization capabilities. The results shown with the contructs of the present invention indicate that the K497E mutant EcR retains some responsiveness to murA, but that ligand-binding is impaired as confirmed by a relatively low fold-induction. Interestingly, however, potentation of B2-K497E by JHIII is relatively high. In other words, while the mutation impairs ligand-binding, it does not affect JH potentiation, indicating that the latter is not necessarily dependent on ligand-binding, but may depend upon the conformation of the receptor at other regions of the protein.

In one embodiment, the K497E mutation may affect ligand-dependent transcriptional function (AF2) associated with helix 12, which normally interacts with the K497 region in the presence of an activating ligand. In an embodiment, the in vivo expression of the B2 K497E isoform will result in hormone-independent activation of at least some ecdysteroid-responsive genes in *Drosophila* tissues. Thus, the construct may provide insecticidal activity if transfected into insect cells.

A related possibility is that the mutation disrupts an interaction between K497 and the B2 domain. By corollary, the isoform specificity could arise from a steric hindrance that prevents a similar interaction between K497 and the larger N-terminal domains of A and B1. It is unlikely, however, that K497E-B2 may cause the receptor to take on a ligand-activated conformation, because K497E-B2 does not compete effectively for USP dimerization with a ligand-bound wild-type B2. For example, in an embodiment, the K497E-induced conformation of EcR does not confer the high affinity dimerization with USP that is associated with ligand-bound, wild-type B2.

From a regulatory standpoint, the effect of K497E illustrates that normal transcriptional activity is not synonymous with maximal transcriptional activity for EcR. Whatever the mechanistic basis for the constitutive activity, the effects of K497E suggest that ecdysteroid inducibility normally includes a derepressive process, which can be mutationally subverted. The K497E receptor activity profile contrasts with the one previously described for the A483T mutation, which in turn, causes conditional third instar lethality in vivo (Li and Bender, 2000, *Development,* 127:2897-2905), and which has been associated with in vitro corepressor binding (Tsai et al, 1999). Given these distinctions between the two mutational effects, it is conceivable that different molecular mechanisms confer repression of receptor activity, and these are genetically and pharmacologically separable.

The constructs of the present invention provide for an analysis of specific portions of the EcR and USP proteins. Earlier in vitro studies have shown that in vivo missense mutations of the EcR ligand-binding domain appear to cause a general and nonspecific impairment of receptor function, for which lethality results from a prolonged deficit in ecdysteroid response that ultimately leads to death. In contrast, the constructs of the present invention show that a specific mutation may evoke isoform-specific effects, illustrating that common region mutations may not affect each isoform equivalently. Thus, the constructs of the present invention provide methods and systems for the isolation of stage-specific insecticides. Also, the constructs of the present invention indicate that for some species, the USP DBD may be essential for ecdysteroid-induced transcription in a homologous (Dm-Dm) construct. Thus, in an embodiment, the constructs of the present invention provide methods and systems for the isolation of species-specific insecticides.

i. Potentiation of EcR by Compounds that Stimulate FXR

Using the methods and assay systems of the present invention, it has been determined that compounds derived from everyday plants, such as farnesol and other juvenoids, and including those that may constitute a portion of the human diet, may comprise the ability to activate FXR and/or EcR (i.e., to increase FXR-mediated transcription or EcR-mediated transcription, respectively) and thus, may function as insecticides and/or insect growth regulators (see e.g., Patent Publication No.: 2005/0049230).

In one embodiment, the compounds that increase or potentiate species-specific and/or stage specific EcR-mediated transcription comprise farnesol metabolites. Farnesyl diphosphate is metabolized to juvenile hormone III, and at least some of the intermediate metabolites may interact with FXR to induce RXR mediated transcription. For example, farnesol, nerolidol, and JHIII may induce FXR greater than 10-fold. Also, in an embodiment, farnesal, farnesoic acid, and methyl farnesoate, also interact with FXR to induce RXR mediated transcription.

Figure 13A:
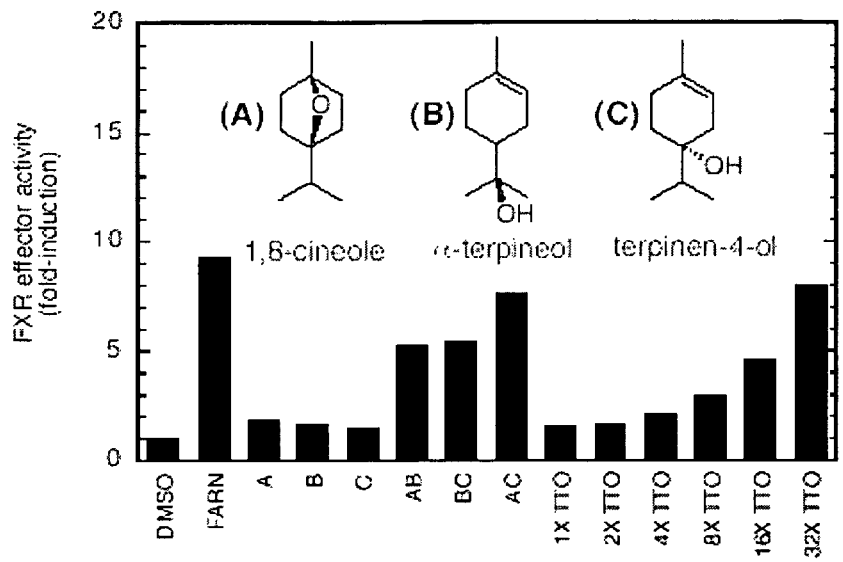
FIG. 13 shows FXR activation profiles for plant secondary metabolites and congeners in accordance with example embodiments of the present invention, wherein the following compounds were tested for FXR activation: (13A) tea tree oil and constituents α-terpineol, 1,8-cineole, and terpinen-4-ol (added individually at 800 μM or together at 400 μM and compared with increasing amounts of tea tree oil (TTO)); (13B) coffee diterpenes cafestol acetate and kahweol acetate; (13C) cucurbitacin D (cuc D) (1 μM) added to cells with, or without, farnesol (45 μM) or chenodeoxycholic acid (CDCA) (40 μM); (13D) bergamot ingredients bergamotin, 5-methoxypsoralen, and 8-methoxypsoralen; (13E) methylenedioxyphenyl compounds myristicin, methyleugenol, and safrole; (13F) rotenone and rotenonic acid with a cleaved furan ring; (13G) hops ingredients isoxanthohumol (IX); xanthohumol (XN); and 8-prenylnaringenin (8PN); and (13H) xanthines caffeine (CF), theophylline (TP), xanthine (XT), hypoxanthine, and theobromine (TB) (not shown).

Also, the compounds that increase or potentiate species-specific or stage-specific EcR-mediated transcription, may comprise juvenile hormone mimetics. For example, FXR-activating farnesoids have been described as JH agonists in insect bioassays (Schneiderman and Gilbert, 1964, *Science*, 1964, 143:325-333). Thus, in one example embodiment, the JH mimetics comprise farnesol, neorlidol, and phytol (Table 4), as well as the synthetic juvenoids methoprene, pyriproxyfen, and the ethyl ester of 7,11-dicholoro-2-ene farnesoic acid (FIG. 13A).

TABLE 4

JH and FXR Activities of Isoprenoids and Chemicals

| ISOPRENOID | JH ACTIVITY a (units/g) | FXR ACTIVITY (fold-induction) |
|---|---|---|
| cecropia oil | 1000 | N.T. |
| phytol | 32 | 3 |
| isophytol | 0 | N.T. |
| all-trans farnesol | 140 | 9 |
| farnesal | 32 | 2 |
| farnesyl acetate | 5.4 | 12 |
| farnesenic [farnesoic] acid | 7.8 | 3 |
| hexahydrofarnesol | 0 | N.T. |
| nerolidol | 8.9 | 9 |
| linalool | 0.08 | 1 |
| geraniol | 0 | 1 |
| geranyl linalool | 0.14 | N.T. |
| solanesol | 0.05 | N.T. |
| juvenile hormone III | — | 20 |
| methoprene | — | 15 |
| pyriproxyfen | — | 9 |
| fenvalerate | — | 12 | a From Schneiderman and Gilbert, Science 143: 325-329 (1964).
N.T. = not tested; FXR activity of "1" indicates that the FXR-dependent transcriptional induction was less than 2-fold when tested at doses below cytotoxicity. Chemicals were tested at a final dose of 50 ∝M.

In another embodiment, the compounds that increase or potentiate species-specific or stage-specific EcR-mediated transcription, comprise plant-derived JH agonists. In one example embodiment, the plant derived JH agonists that increase or potentiate species-specific or stage-specific EcR-mediated transcription, comprise echinacea oil, echinolone, juvocimene, juvabione, α-bisabolol, olive oil, 2-hydroxyphenethlyl alcohol, 3-hydroxyphenethlyl alcohol, or 4-hydroxyphenethlyl alcohol. In another embodiment, the compounds that increase increase or potentiate species-specific or stage-specific EcR-mediated transcription comprise insecticide synergists. In a further embodiment, the insecticide synergists that increase increase or potentiate species-specific or stage-specific EcR-mediated transcription, comprise piperonyl butoxide (PB), seasamin, sesame oil, piperine, myristicin, or apiole.

In an embodiment, the compounds that increase or potentiate species-specific or stage-specific EcR-mediated transcription, comprise monoterpenes. In a further embodiment, the monoterpenes that increase increase or potentiate species-specific or stage-specific EcR-mediated transcription, comprise tea tree oil (terpenen-4-ol, 1,8-cineole, and α-terpineol), carvacrol, thymol, perillyl alcohol, fenchyl alcohol, or pinane diol (Table 4 and FIGS. 13A and 13B).

The compounds that increase or potentiate species-specific or stage-specific EcR-mediated transcription, may also comprise diterpenes. In a further embodiment, the diterpenes that increase increase or potentiate species-specific or stage-specific EcR-mediated transcription, comprise forskolin, 1-trans-$\Delta^9$-tetrahydrocannabinol (THC), abietic acid, croton oil, and other phorbol-like diterpenes such as phorbol 12,13-dibutyrate, mezerein, and also ingenol 3,20-dibenzoate, cafestol, kahweol, or their acetate derivatives.

Also, the compounds that increase or potentiate species-specific or stage-specific EcR-mediated transcription, may comprise triterpenes. In yet a further embodiment, the triterpenes that increase or potentiate species-specific or stage-specific EcR-mediated transcription, comprise essential oils from myrrh and frankincense, β-boswellic acid, oleanolic acid, rosemary oil, or 20α- or 20R-hydroxycholesterol.

Figure 13B:
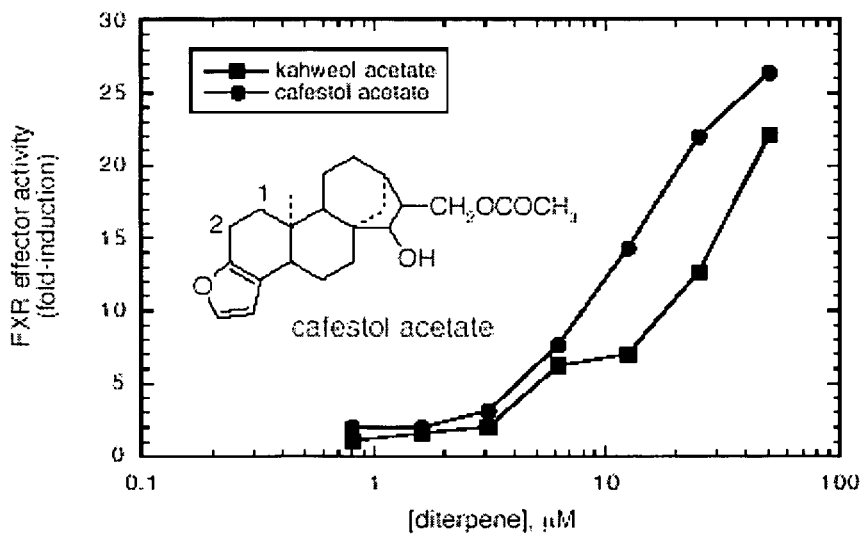
Figure 13C:
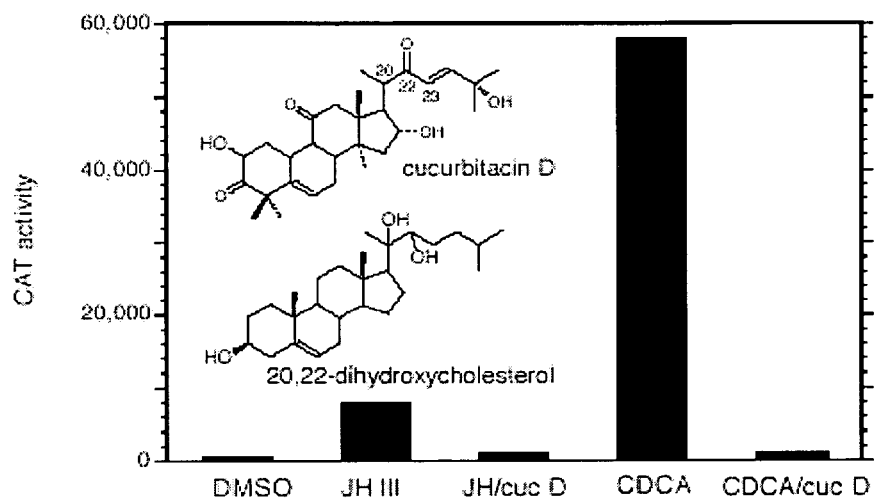

The present invention also comprises compounds that can suppress the activity of FXR or EcR in a species-specific and/or developmental stage specific manner. Compounds that inhibit the ecdysone receptor (EcR) may suppress FXR activity. Also, the compounds that inhibit FXR activity may suppress FXR activity promoted by FXR modulators. In one example embodiment, 1 μM cucurbitacin D (cuc D) may suppress FXR-dependent activity promoted by JH III and chenodeoxycholate (CDCA) (40 μM each), 7-fold and 58-fold, respectively (FIG. 13C). Also, the $\Delta^1$-unsaturated congener cucurbitacin I may inhibit farnesol-induced activity with an $IC_{50}$~50 nM (data not shown).

The compounds that increase or potentiate species-specific or stage-specific EcR-mediated transcription, may also comprise furocoumarins or phenylpropanoids. In one example embodiment, the fucocoumarins and phenylpropanoids that increase or potentiate species-specific or stage-specific EcR-mediated transcription, comprise the furocoumarins, bergamot oil and bergamotin (from Earl Grey tea) (FIG. 13D), myristicin, or apiole, or the phenylpropanoid, methyleugenol (FIG. 13E).

In other embodiments of the present invention, the compounds that increase or potentiate species-specific or stage-specific EcR-mediated transcription may comprise coumarins and flavanoids. The coumarins and flavanoids that increase EcR-dependent transcription may, for example, comprise silybin, tangeretin or a rotenonic acid (FIG. 13F) or 8-prenylnaringenin and isozantholhumol from hops.

The compounds that increase or potentiate species-specific or stage-specific EcR-mediated transcription, may also comprise linoleic acid metabolites. In yet a further embodiment, the linoleic acid metabolites that increase or potentiate species-specific or stage-specific EcR-mediated transcription, comprise cis-jasmone or methyl jasmonate.

Also, in an embodiment, the compounds that increase or potentiate species-specific or stage-specific EcR-mediated transcription comprise polyketides from hops. In yet a further embodiment, the polyketides that increase increase or potentiate species-specific or stage-specific EcR-mediated transcription, comprise humulone (FIG. 13G).

Also, in an embodiment, the compounds that increase or potentiate species-specific or stage-specific EcR-mediated transcription comprise xanthines. In yet a further embodiment, the xanthines that increase or potentiate species-specific or stage-specific EcR-mediated transcription, comprise theophylline, caffeine, 8-Br-cAMP, dibutyryl cAMP, or 8-Br-cAMP in combination with theophylline (FIG. 13H).

In an embodiment, man-made insecticides may increase or potentiate species-specific or stage-specific EcR-mediated transcription. For example, in an embodiment, man-made insecticides that increase or potentiate species-specific or stage-specific EcR-mediated transcription, comprise cinerins, pyrethrins, jasmolins, synthetic pyrethroids including cypermethrin, permethrin, phenothrin, and bioallethrin (Table 5).

TABLE 5

FXR Activation by Plant Essential Oils and Ingredients

| PLANT OIL | FXR ACTIVITY | INGREDIENT | DOSE (µM) | FXR ACTIVITY* (fold-induction) |
|---|---|---|---|---|
| allspice | 7 | | | |
| balm | 4 | | | |
| balsam fir | 3 | juvabione | | |
| basil | 10 | juvocimene | 25 | 9 |
| bergamot | 10 | bergamotin | 25 | 10 |
| | | bergapten | 100 | 1 |
| black pepper | N.T | piperine | 50 | 4 |
| cardomom | 3 | | | |
| *cassia* bark | 1 | | | |
| cedarwood | 9 | α-ionone, β-ionone | 150 | 10 |
| clove | 3 | eugenol | 200 | 1 |
| coffee | N.T | caffeine | 3000 | 12 |
| | | theophylline | 3000 | 12 |
| | | caffeic acid | 100 | 1 |
| | | cafestol | 20 | 12 |
| | | kahweol | 20 | 10 |
| *coleus forskholi* | N.T | forskolin | 10 | >100 |
| cottonseed | 1 | | | |
| croton | 3 | ingenol-3,20-dibenzoate | 10 | 5 |
| derris | N.T | rotenone | 20 | 1 |
| | | rotenonic acid | 20 | 20 |
| *Echinacea* | 7 | echinolone | | N.T. |
| Fennel | 7 | | | |
| Frankincense | 30 | β-boswellic acid | 25 | 11 |
| Ginger | 4 | | | |
| Hops | 18 | 8-prenylnaringenin | 20 | 38 |
| | | Humulone | 20 | 8 |
| | | Xanthohumol | | 1 |
| | | Isoxanthohumol | 20 | 9 |
| | | Lupulone | 20 | 1 |
| milk thistle | 4 | silybin | 100 | 10 |
| myrrh | 22 | | | |
| nutmeg | N.T. | methyleugenol | 250 | 4 |
| olive oil | 4 | phenethyl alcohols | 400 | 4 |
| orange | N.T. | limonene | 300 | 1 |
| | | perillyl alchol | 300 | 4 |
| *origanum* | 6 | carvacrol | 300 | 6 |
| | | thymol | 300 | 6 |
| parsley | N.T. | myristicin | 250 | 4 |
| | | safrole | 250 | 1 |
| pyrethrum | 10 | pyrethrin | | N.T. |
| | | cinerin | | N.T. |
| | | jasmolin | | N.T. |
| rice | N.T. | γ-tocotrienol | 20 | 1 |
| sage | 8 | | | |
| sesame | 3 | sesamin | 100 | 12 |
| | | sesamol | | 1 |
| spruce | N.T. | abietic acid | 50 | 23 |
| tea tree | 8 | 1,8-cineole | 400 | 2 |
| | | α-terpineol | 402 | |
| | | terpinen-4-ol | 400 | 2 |
| thyme | 13 | | | |
| vetiver | 24 | | | |
| ylang ylang | 17 | cis-jasmone | 1000 | 6 |
| | | methyl jasmonate | 1000 | 18 |

*FXR activity is defined as the ratio of FXR-dependent CAT activity attained in appropriately transfected cells at maximal doses of plant oil (or indicated doses of ingredients) over that for the vehicle. Activity level of "1" indicates no increase in activity over vehicle.

Figure 14:
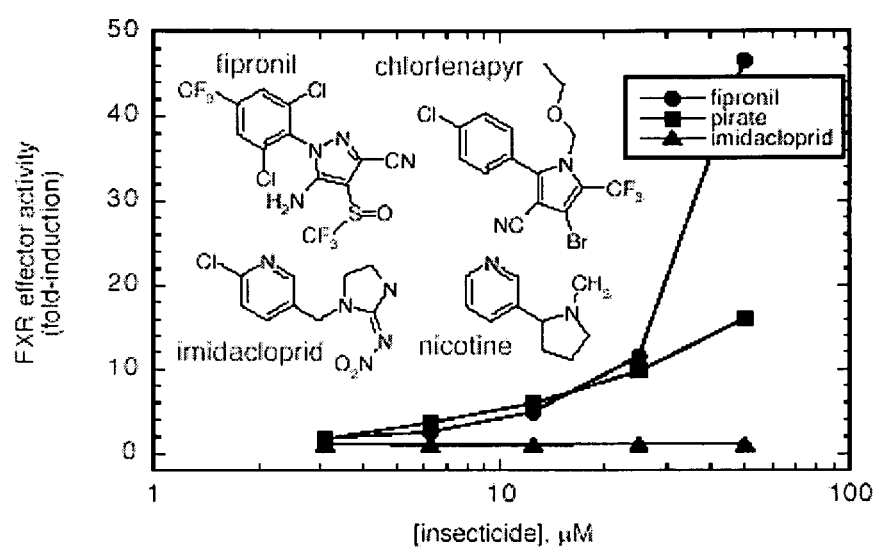
FIG. 14 shows FXR-mediated transcription may be increased by phenylpyrazole insecticides in accordance with an example embodiment of the present invention, wherein increasing doses of fipronil, chlorfenapyr (pirate), and imidacloprid were tested as indicated for the ability to increase FXR-mediated transcription.

Also, insecticides such as o,p-DDT (but not p,p-DDT), chlordane, kepone, lindane, dieldrin, toxaphenes, aroclor 1254, 2,3,7,8-tetrachlorodibenzo-p-dioxin, malathion, diazinon, chlorpyrifos, parathion, ethion, chlorfenapyr, pyrethrin, permethrin, fenvalerate, or fipronil may increase or potentiate species-specific or stage-specific EcR-mediated transcription in an embodiment of the present invention (Table 6; FIG. 14).

TABLE 6

FXR Is Activated by Synthetic Insecticides

| COMPOUND | STRUCTURE | DOSE (μM) | FXR ACTIVITY (fold-induction) |
|---|---|---|---|
| chlordane | 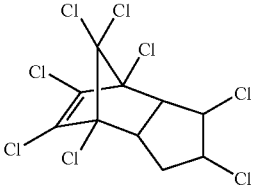 [SMILES: ClC1=C(Cl)C2(Cl)C3C(Cl)C(Cl)CC3C1(Cl)C2(Cl)Cl] | 5 | 7 |
| o,p-DDT | 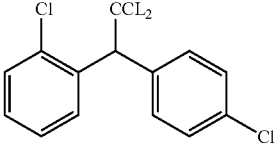 | 5 | 3.5 |
| dieldrin | 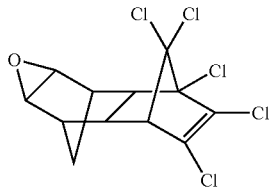 [SMILES: ClC1=C(Cl)C2(Cl)C3C4CC(C5OC45)C3C1C2(Cl)Cl] | 5 | 17 |
| tetrachloro-dibenzo-p-dioxin | 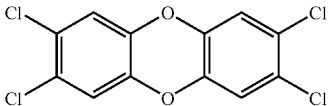 [SMILES: Clc1cc2c(cc1Cl)Oc1cc(Cl)c(Cl)cc1O2] | 0.1 | 15 |
| malathion | 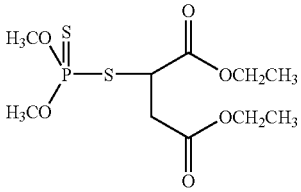 [SMILES: CCOC(=O)CC(SP(=S)(OC)OC)C(=O)OCC] | 50 | 13 |
| diazinon | 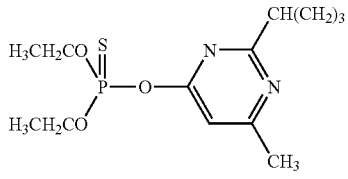 | 50 | 33 |
| phosdrin | 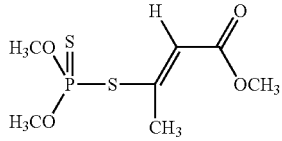 | 100 | 1 |

TABLE 6-continued

FXR Is Activated by Synthetic Insecticides

| COMPOUND | STRUCTURE | DOSE (μM) | FXR ACTIVITY (fold-induction) |
|---|---|---|---|
| pyrethrin I (pyrethrum extract) | 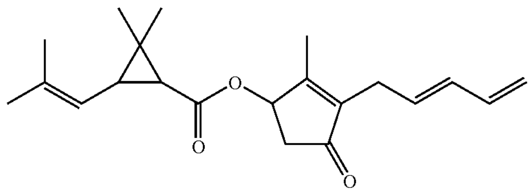 [SMILES: C=C/C=C/CC1=C(C)C(OC(=O)C2C(C=C(C)C)C2(C)C)CC1=O] | Maximum | 10 |
| permethrin | 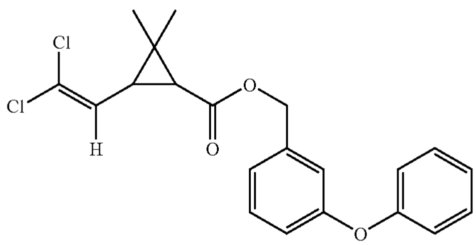 [SMILES: CC1(C)C(C=C(Cl)Cl)C1C(=O)OCc1cccc(Oc2ccccc2)c1] | 25 | 5 |
| fenvalerate | 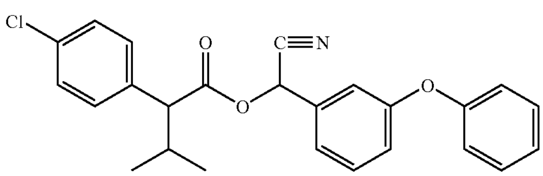 [SMILES: CC(C)C(C(=O)OC(C#N)c1cccc(Oc2ccccc2)c1)c1ccc(Cl)cc1] | 25 | 9 |

The present invention recognizes that small doses of ecdysone may prime the EcR-dependent transcriptional response provoked by JHs. Ecdysones may stabilize a conformation of EcR that permits JHs to bind more effectively. Since JH potentiators may affect the maximal transcriptional response elicited by ecdysone, this may be similar to allosteric enzymes whose effectors alter the apparent $V_{max}$ without changing the $K_m$ value. Thus, the variable cytotoxicities provoked by dietary or ectopically-applied ecdysones, JHs, or insecticides in different insects may be uniquely imparted by their pharmacologically-distinguishable EcR/USP complexes.

In one embodiment, the present invention describes the use of JH antagonists as compound that may be used to modulate insect growth. In one embodiment, the JH antagonists may increase FXR-mediated transcription and/or EcR-mediated transcription. Alternatively, the JH antagonists may inhibit FXR-mediated transcription and/or EcR-mediated transcription.

Thus, in one embodiment, transcriptional activity programmed by muristerone-primed ecdysone receptors may be potentiated by juvenile hormones, compounds derived from food sources, and insecticides (FIG. 15). The transcriptional effects may, in some embodiments, require ligand binding domain sequences of the EcR or FXR (FIG. 16). In an embodiment, mutations in the LBD of FXR or EcR may be utilized to prepare constructs specific to various types of potential insecticide compounds.

Also, natural JH's may increase or potentiate species-specific or stage-specific EcR-mediated transcription. For example, FXR may respond to the JH I analog ZR354 in which the ethyl groups of JH I ethyl are replaced by similarly bulky dimethyl groups. In one embodiment, the natural JH's that increase or potentiate species-specific or stage-specific EcR-mediated transcription, comprise all "natural" JHs, e.g., JH 0, JH1, and JH II (where ethyl groups are substituted for JH III methyl groups).

Compositions for Use as Insecticides

Species-specific activators of EcR, or compounds that potentiate EcR may be used in the form of compositions and can be applied to the crop and/or plant to be treated, simultaneously with, or in succession with, other compounds such as fertilizers, micronutrient donors or other preparations which influence the growth of plants. The compounds can also be selectively combined with herbicides, as well as, other insecticides, fungicides, bactericides, nematocides, molluscicides or mixtures of several of these preparations and, if desired together with further carriers, surfactants or application promoting adjuvants employed in the art of formulation, and as described in U.S. Pat. Nos. 6,737,383, 6,630,465, 6,586,470, 6,603,044, 6,617,341, 5,942,542, and 5,849,320.

For example, when applying the compound that comprises a species-specific and/or stage specific mediator of EcR, the compound may be applied in a form as it is without adding other active components. When the compound of the present invention is applied for plant protection purpose, the compound can be prepared into general types of formulations for plant protection use, such as wettable powder, granules, dust, emulsifiable concentrate, water soluble powder, suspension concentrate, flowable liquid, and the like.

The inert carrier used in this invention may be either solid or liquid. Where the compound of the present invention is prepared into a solid formulation, appropriate additives and carriers may be incorporated with the compound. The solid carrier may be a solid such as soybean flour, cereal flour, wood flour, bark flour, saw dust, powdered tobacco stalks, powdered walnut shells, bran, powdered cellulose, extraction residues of vegetables, powdered synthetic polymers or resins, clays (e.g. kaolin, bentonite, and acid clay), talcs (e.g. talc and pyrophyllite), silica powders or flakes (e.g. diatomaceous earth, silica sand, mica and white carbon, activated carbon, powdered sulfur, powdered pumice, calcined diatomaceous earth, ground brick, fly ash, sand, calcium carbonate powder, calcium phosphate powder and other inorganic or mineral powders, chemical fertilizers (e.g. ammonium sulfate, ammonium phosphate, ammonium nitrate, urea and ammonium chloride), and compost. These carriers may be used alone or as a mixture thereof.

Where the compound of the present invention is prepared into a liquid formulation, an appropriate solvent may be used for dissolving or dispersing the compound in the liquid type formulation. The liquid carrier is that which itself has solubility or which is without such solubility but is capable of dispersing an active ingredient with the aid of an adjuvant. The following are typical examples of the liquid carrier and can be used alone or as a mixture thereof: water; alcohols such as methanol, ethanol, isopropanol, butanol and ethylene glycol; ketones such as acetone, methyl ethyl ketone, methyl isobutyl ketone, diisobutyl ketone and cyclohexanone; ethers such as ethyl ether, dioxane, dipropyl ether and tetrahydrofuran; aliphatic hydrocarbons such as kerosene and mineral oils; aromatic hydrocarbons such as benzene, toluene, xylene, solvent naphtha and alkylnaphthalenes; halogenated hydrocarbons such as dichloroethane, chloroform, carbon tetrachloride and chlorobenzene; esters such as ethyl acetate, diisopropyl phthalate, dibutyl phthalate and dioctyl phthalate; amides such as dimethylformamide, diethylformamide and dimethylacetamide; nitriles such as acetonitrile; and dimethyl sulfoxide. In one embodiment, the composition of the invention may also applied to the plant foliage or plant stem or insect habitat as a dilute spray prepared from any of the above-said formulations.

Also, to provide uniformity and stability to the compound in the prepared compositions, it is possible to add surface active agents into each formulation upon necessity. To emulsify, disperse, dissolve and/or wet an active ingredient, a surfactant is used. There is no limitation for the surface active agent, and examples of the surface active agent that can be added to the above-mentioned formulations include nonionic surface active agents, such as polyoxyethylene-added alkyl ether, polyoxyethylene-added higher fatty acid ester, polyoxyethylene-added sorbitan higher fatty acid ester and polyoxyethylene-added tristyryl phenyl ether, a sulfate ester of polyoxyethylene-added alkyl phenyl ether, an alkyl benzene sulfonate, a polycarbonate, a lignin sulfonate, a formaldehyde condensate of alkyl naphthalene sulfonate, and a copolymer of isobutylene and maleic anhydride.

Further, to stabilize the dispersion of an active ingredient, tackify it and/or bind it, there may be used adjuvants such as casein, gelatin, starch, methyl cellulose, carboxymethyl cellulose, gum arabic, polyvinyl alcohols, turpentine, bran oil, bentonite and ligninsulfonates. Also, to improve the flowability of a solid product, there may be used adjuvants such as waxes, stearates and alkyl phosphates. Adjuvants such as naphthalenesulfonic acid condensation products and polycondensates of phosphates may be used as a peptizer for dispersible products. Adjuvants such as silicon oils may also be used as a defoaming agent. For example, adjuvants such as those described in U.S. Pat. No. 5,942,542 may be used.

While the compound of the present invention may be used alone, it can be combined for the use with one or more of various types of other plant protection chemicals, for example, fungicides, insecticides, acaricides and synergists. Also, in one embodiment, the composition may comprise a seed coating, formulated as described in U.S. Pat. No. 5,849,320.

The insecticide compounds of the present invention may be used in admixture with other agricultural and horticultural disease or pest controllers, acaricides, nematicides, bioagrochemicals, etc.; and herbicides, plant growth regulators, manures, etc. depending upon scenes using the present agricultural and horticultural insecticides, in order to expand both spectrum of controllable diseases and insect pest species and the period of time when effective applications are possible or to reduce the dosage.

The insecticide compounds of the present invention may be applied using a variety of protocols. Thus, the composition may be applied to a crop on which the insect pests are expected to appear, or to a site where the appearance of the insect pests is undesirable. The insecticide compositions of the present invention may also be applied to the plant seeds or the cultivation mediums for seeding such as soil to be seeded, the mat for raising seedlings, water, and the like, by the method of application to a nursery box, seed powdering, etc. or by the method of seed disinfection. For controlling the pest insects generated on fruit trees, cereals, upland field for vegetables, etc., it is also possible to make a plant absorb the compounds of the present invention by a seed treatment such as powder coating, dipping, etc., irrigation into seedling-raising carrier such as seedling-raising vessel, or planting hole, or by treatment of the culture solution for water culture.

The applied dosage of the insecticide compounds of the present invention may be varied depending upon various factors such as the insect pests to be controlled, the growth state of a plant, weather, environmental conditions, the preparation form, application method, application site and application time. In one example embodiment, the does may comprise a range of 0.1 g to 10 kg (in terms of the active ingredient) per 10 acres depending upon purposes. Thus, the amount of an active ingredient in each of the composition may be in a range of from 0.01 to 90% by weight, or preferably from 0.05 to 85% by weight based on the total weight of the formulation. In dusts, granules, or emulsifiable concentrates, the suitable content thereof is from 0.01 to 50% by weight. Each of the prepared formulations, such as wettable powder, emulsifiable concentrate, suspension concentrate and flowable solution, may be diluted with water or other solvent to be prepared and adjusted into the suspension or emulsion with a desired concentration to be applied to crop plants. For the formulations, such as granular and dust formulations, the formulation itself is directly applied to the target crop plants or soil.

The compositions of the present invention comprise compounds that increase FXR-mediated transcription and/or increase or potentiate EcR-mediated transcription present as non-toxic doses. JH levels in the insect support the use of FXR and EcR-activating compounds as insecticides. Thus, in alternate embodiments of the present invention, the compounds may comprise a dosage ranging from 0.01 μM to about 10 mM, or from about 0.1 μM to about 1 mM, or from about 0.5 μM to about 50 μM.

For example, JH III circulates in honeybee hemolymph at 0.5 μM (Elekonich et al., 2001, *J. Insect Physiol.*, 47:1119-1125), which matches the concentration of the JH III precursor farnesyl diphosphate found in the rat liver (Bruenger and Rilling, 1988, *Anal. Biochem.*, 173:321-327). Also, JH III titers in *Diploptera* hemolymph are 6 mM during the middle of the gonotrophic cycle and 10-fold lower at other times (Tobe et al., 1985, *Experientia*, 41:1028-1034). Purification of 1.6 mg of JH I ($M_r$=294) from 875 *Cecropia* abdomens (380 g) translates to 1.5 μM in the whole insect (Roller and Dahm, 1968, *Recent Prog. Horm. Res.,* 1968, 24:651-80). These amounts are near the doses of JH III or farnesol (2 µM) that elicit FXR-dependent activity in the CHO assay of the present invention.

EXAMPLES

Example 1

Cell Growth Conditions

Chinese hamster ovary (CHO K1) cells were grown in Dulbecco's modified Eagle medium: nutrient mixture F-12 (1:1) containing 5% fetal bovine serum and supplemented with 50 u/ml penicillin, and 50 µg/ml streptomycin (Life Technologies) in a water-jacketed incubator held at 37° C. and maintained with a 5% $CO_2$ atmosphere.

Example 2

Assay System

These experiments employed a mammalian cell culture system using Chinese hamster ovary cells (CHO) to evaluate the transcriptional function of *Drosophila melanogaster* EcR and USP using methods described previously (U.S. Patent Application Publication No: 2005/0049230; Henrich et al, 2003). Cells were seeded in 6-well polypropylene culture plates (Falcon) with $10^5$ cells per well on the day prior to transfection. Transfection was subsequently performed using either calcium phosphate (Kitareewan et al., 1996, *Mol. Biol. Cell,* 7:1153-1196) or a GenePorter reagent (Gene Therapy Systems, Inc; San Diego, Calif.) following manufacturer's protocols. Each well received 1.25 µg of $(EcRE)_5$-ΔMTV-CAT (five copies of the hsp27 EcRE inserted into an mouse mammary tumor virus (MTV) promoter upstream of the chloramphenicol acetyltransferase (CAT) gene) or $(EcRE)_5$-ΔMTV-LUC (the same promoter attached to firefly luciferase), 1.25 µg of pCH111 (SV40 early promoter linked to the β-galactosidase gene) to normalize CAT activity, and 0.25 µg of each expression plasmid (EcR, FXR, RXR, USP) that was tested. The cells were incubated with plasmid DNA for seven hours and then washed with 1×PBS. Muristerone A (murA; Alexis Biochemicals) or 20-hydroxyecdysone (20E; Sigma) dissolved in ethanol to a concentration of 10 mM was diluted as necessary to the final assay concentration (FAC) in 2 ml of fresh incubation medium that was then applied to the cells. Similarly, JHIII (Sigma) was dissolved in dimethyl sulfoxide (DMSO) to a concentration of 80 µM and diluted into the incubation medium to its final assay concentration (20, 40, 80, 160 µM). For experiments to test the effects of chenodeoxycholate (CDCA, Sigma) on FXR and EcR, CDCA was dissolved in DMSO at 20 mM and diluted in the culture medium to a final concentration of 20 µM. A corresponding volume of ethanol and DMSO were added to control cells for all experiments. For all experiments, the cells were allowed to incubate with the medium for 24 hours before collection and cell lysates were prepared by described methods (Kitareewan et al., 1996). Both β-galactosidase and CAT reporter activity were measured based on previously used methods (Kitareewan et al, 1996). Luciferase assays using luciferrin followed the specifications of the manufacturer.

Transcriptional activity, measured as $^{14}C$-chloramphenicol counts (for measuring CAT activity) or relative luciferase activity (RLU) was quantified for each cell lysate. The counts were then normalized by adjusting for differences in β-galactosidase activity, since β-galactosidase expression is controlled by a constitutive promoter and provides an estimate of cell mass. Data were normalized as fold-induction based on differences in reporter gene activity between hormonally treated and control cells.

Preliminary experiments further demonstrated that a saturable and replicable level of transcriptional activity is obtained with the transfection of as little as 25 ng of an EcR-isoform-encoding plasmid (data not shown). Unless noted otherwise, 100 ng of each EcR and USP plasmid was transfected into 2 ml of cell culture medium. As noted above, a reporter gene carrying five tandem copies of the hsp27 ecdysone response element (Riddihough and Pelham, 1986) is attached to a constitutive thymidine kinase promoter and a luciferase reporter gene (pEcREtk-LUC) and cotransfected into the cells along with vectors expressing EcR, USP, and a constitutively active β-galactosidase gene with lipofection, following manufacturer's protocols. The subsequent measure of luciferase activity reflects ecdysteroid-inducible transcription.

The *Drosophila* EcR isoform vectors (A, B1, and B2) used for these experiments have been described previously (Mouillet et al, 2001). These vectors lack the F-domain, which is also not essential for in vivo function (Cherbas et al, 2003). Additionally, three different VP16-USP vectors were utilized. Construction is of the VP16-USP vectors is described below. As in the earlier study, hsp27-EcRE mediated transcriptional activity was measured by detecting the luminescence produced by luciferase in transfected cell extracts. Luciferase activity was normalized by transfection with a plasmid that constitutively expresses the β-galactosidase gene such that enzymatic activity correlated with cellular mass.

After a 4 hour transfection period, the hormone treatment was applied by diluting stock solutions of muristerone A (murA; Alexis Corporation, San Diego, Calif.), JHI (Scitech), JHIII (Sigma, St Louis, Mo.), and/or 20E (Sigma, St Louis, Mo.) in DMSO. The cells were harvested 24 hours after treatment and the contents of the cells extracted for performing the luciferase and β-galactosidase assays.

Example 3

Description of Plasmid Vectors

Chimeric Vectors

Expression plasmids encoding *Drosophila* EcR (CMX-EcR), *Drosophila* USP (CMX-USP), rat FXR (CMX-FXR), human RXRα (CMX-hRXRα), glucocorticoid receptor (CMX-GR), and a glucocorticoid receptor trans-activating domain fused to an ecdysone DBD and LBD (CMX-GEcR) have been described (Yao et al., 1992; Yao et al., 1993; and Forman, 1995). The expression plasmids are constructed by inserting restriction fragments containing the appropriate coding sequence for the gene to be expressed into the CMXPL1 plasmid. For hRXRα, an EcoRI fragment of human RXR-α (hRXRα) was subcloned into the CMXPL1 plasmid.

The FXR expression vector (pRS-rFXR) contains DNA sequences encoding a constitutively active promoter derived from the Rous sarcoma virus long terminal repeat (LTR) fused to the complementary DNA sequence encoding the rat farnesoid-X-activated receptor (Forman et al., 1995; NCBI Accession No. U18374) which is followed by a DNA sequence specifying the SV40 polyadenylation signal. Briefly, the expression plasmid pRS-rFXR was derived from pRS-hGR as follows: pRS-hGR was digested with Kpn I and Bam HI restriction endonucleases to release DNA sequences specifying the human glucocorticoid receptor (GR) and cDNA encoding rat FXR and its 5' and 3' untranslated sequences was then inserted into Kpn I and Bam HI digested pRS-hGR.

GGF, comprising the glucocorticoid (G) amino terminus and DBD linked to the LBD of FXR, was prepared following a strategy similar to that used to construct GGEc (Christopherson et al., 1992, *Proc. Natl. Acad. Sci. USA*, 89:6314-6318), where the GR amino terminus and DBD (appending 23 amino acids downstream from the conserved gly-met) were fused to the FXR LBD. To construct GGF, the plasmid pRShGR$_{nx}$ (Giguere et al., 1987, *Nature*, 330:624-9), with Not I and Xho I sites flanking the GR DBD, was first used as a template in a polymerase chain reaction (PCR) assembled with the forward primer 5'-GGAATGATTGCATC ATCGATAAAATTCG-3' (Cla I restriction site underlined) (SEQ ID NO: 1) and the reverse primer 5'-GAGGT CTCGAGTGAGACTCCTGTA-3' (Xho I site underlined) (SEQ ID NO: 2). Cla I- and Xho I-digested pRShGR$_{nx}$ was then ligated to the 132 bp PCR product. The resulting plasmid was digested with Xho I and Bam HI and the GR-containing DNA fragment was isolated and ligated to an Xho I-Bam HI LBD fragment from an FXR variant prepared by hybridizing the oligonucleotide 5'-CTCGAGTGTATGTATACAG-GTTTGTTAACTGAA-3' (SEQ ID NO: 3) to another oligonucleotide 5'-AACAAACCTGTATACATACACTCGA-3' (SEQ ID NO: 4) which was then ligated to a Hpa I-digested fragment from the pRSV-FXR expression vector. The DBD/LBD junction in GGF is 5'-GMNLEARKTKKK-IKGIQQATTGVSQECMYTGLLTE-IQCKS-3' (SEQ ID NO: 5) where the GR residues are underlined, amino acids GM are the last two residues of DNA binding domain and amino acids from FXR are in bold (not underlined).

The GGEc vector (Christopherson et al., 1992) is derived from the rat GR expression vector pRSV.GGG (Miesfeld et al., 1986, *Cell*, 46:389) and contains the Rous sarcoma virus LTR fused to DNA encoding the rat glucocorticoid receptor (GR) amino terminus and DNA binding domain fused to a DNA sequence encoding the *Drosophila melanogaster* ecdysteroid receptor (EcR) (NCBI Assession No. M74078; Koelle et al., 1991) ligand binding domain (LBD). In GGEc, rat GR LBD amino acids 528 to 795 were replaced by EcR LBD amino acids 329 to 878).

The GEcEc (i.e., GRdEcR) vector has been described previously (Yao et al., 1993; No et al., 1996, *Proc. Natl. Acad. Sci USA*, 93:3346-3351). Briefly, GEcEc was constructed by ligation of a Not I-Bam HI fragment containing the DBD and LBD of a modified EcR cDNA, EcR$_{nx}$, in place of the DBD and LBD of the similarly modified GR expression vector construct pRShGRnx (Giguere et al., 1987). The modified EcR cDNA was constructed using site-directed mutagenesis (Kunkel, 1985, *Proc. Natl. Acad. Sci., USA*, 82:488) to insert Not I (oligonucleotide template: 5'-CCTGCGCCACGGCG-GCCGCCGGAGCTGTGCCTG-3') (SEQ ID NO: 6) and Xho I (oligonucleotide template: 5'-GTGGGTATGCGC-CTCGAGTGCGTCGTCCC-3') (SEQ ID NO: 7) sites immediately flanking the DBD. This results in conversion of amino acids 259-261 from ValGlnGlu to ArgProPro and amino acid 331 from Pro to Leu.

Reporter plasmids EcR$_5$-ΔMTV-LUC, and MMTV-LUC have also been described (Yao et al., 1992; Yao et al., 1993; and Forman, 1995). The reporter plasmids may be constructed by inserting a ecdysone reponse element (e.g., 5'-GATCCGACAAGGGTTCAATGCACTTGTCA-3'; SEQ ID NO: 8) at position-77 of a mouse mammary tumor virus (MMTV or MTV) promoter-reporter gene construct, such as MTV-CAT, MTV-LUC, MTV-GFP (Christopherson, 1992).

The (EcRE)$_5$-ΔMTV-LUC construct was produced by subcloning the promoter region of MTV into the multiple cloning site of the p-LUC plasmid (Promega); this vector resembles the (EcRE)$_5$-ΔMTV-LUC described previously (No et al, 1996).

Construction of the three *Drosophila* EcR isoform vectors (EcRA, EcRB1, EcRB2) has been described (Mouillet et al., 2001). To generate the vectors EcR-A, B1, and B2 sequences (Koelle et al., 1991; Talbot et al., 1993; NCBI Accession Nos. S63761 and S63762) generated by PCR were cloned into the BamHI and XbaI sites of the pcDNA3 vector (InVitrogen). The EcRA DNA fragment was produced by using PCR amplification of EcRA DNA with the pWT57 vector as a template (Talbot et al, 1993). The forward primer, DEAf (5'-CACCCGGATCCACCATGTTGACGAC-GAGTGGACAA) (SEQ ID NO: 9) was used with the reverse primer, DEr (5'-ACCTCTCTAGACTATGCAGTCGTC-GAGTGGTC) (SEQ ID NO: 10) to produce a fragment that was subsequently digested with BamHI and XbaI and ligated into a pcDNA3 vector digested with BamHI and XbaI. The plasmid encodes a version of EcRA that includes 849 amino acids, and deletes the F domain. The EcRB1 DNA fragment was produced by using PCR amplification with the pMK1 vector (Koelle et al, 1991; Talbot et al, 1993) using the aforementioned DEr primer with the forward primer, DEB1f (5'-CACCCGGATCCACCATGAAGCGGCGCTG-GTCGAAC) (SEQ ID NO: 11). The fragment was subsequently digested and cloned into the pcDNA3 vector as described for A. The plasmid encodes a version of EcRB1 that includes 878 amino acids, and deletes the F domain. The EcRB2 DNA fragment was produced by using PCR amplification with the pWT56 vector (Talbot et al, 1993) using the aforementioned DEr primer with the forward primer, DEB2f (5'-CACCCGGATCCACCATGGATACTTGTG-GATTAGTA-3') (SEQ ID NO: 12). The fragment was subsequently digested and cloned into the pcDNA3 vector as described for A. The plasmid encodes a version of EcRB2 that includes 669 amino acids, and deletes the F domain.

The VP16dEcR vector has also been described previously (Yao et al., 1993; No et al., 1996; Mouillet et al., 2001; Henrich et al., 2003). The VP16 EcR vector was constructed using PCR amplification with pWT57 with the reverse primer, Der (described above), together with the forward primer Def (5'-CACCCGGATCCACCATGAAGAAGG-GACCTGCGCCA-3') (SEQ ID NO: 13). The fragment was subsequently digested with BamHI and XbaI and cloned in to the multiple cloning site of pVP16 (Clontech). The resulting vector encodes a protein consisting of the VP16 activation domain linked to the C-E domain of EcR and consisting of 626 amino acids.

The VP16CfUSP vector is also previously described (Palli et al., 2003). The USP vector contains the USP LBD of *Chorisioneura fumeriferana* (NCBI Accession No. AF045891). Both VP16 chimeras contain an N-terminal domain that is active in mammalian cells (Louvion et al, 1993, *Gene*, 131:120-134). To generate VP16CfUSP, PCR amplification with a forward primer including an EcoRI site and a reverse primer including a BamHI site was used to produce a fragment that encodes the D-F domains of *Choristoneura fumiferana* USP (Accession #AAC31795). The resulting PCR product was digested with EcoRI and BamHI and cloned into the pVP16 vector (Clontech) to produce the fusion protein.

USP Dm Vectors.

Three USP constructs were made by subcloning three different *D. melanogaster* USP inserts into the pVP16 vector (Invitrogen). The VP16 vector encodes a fusion protein of the viral protein 16 (VP16) activation domain. In the vectors of the present invention, the VP16 activation domain was then fused to various carboxy-terminal fragments of the USP open reading frame. The USP portion of each fusion gene was isolated by PCR from a plasmid, pZ7-1 (Henrich et al, 1990). The forward primers were tailed with an EcoRI restriction site on the 5' end and the reverse primer was tailed with a HindIII site on the 5' end. These sites allowed for directional cloning directly into the multiple cloning site of the vector.

The VP16-dUSPF1 insert, which includes the last 6 amino acids of the N-terminal domain and the remaining carboxy-terminal portion of the open reading frame (amino acids 98-507) which includes the two cysteine-cysteine zinc fingers of the DNA-binding domain (DBD), the hinge region, and ligand-binding domain (LBD). The fragment was isolated by PCR using the forward primer (VP16-dUSPF1) 5' TTTT GAATTC AGCGGCAGCAAGCACCTCTGC 3' (SEQ ID NO: 14) and the reverse primer VP16-dUSPR 5' TTTT AAGCTT TAGAGTCGGGACCCTACTCC 3' (SEQ ID NO: 15) (underline designates restriction site).

The slightly shorter VP16-dUSPF2 starts at the beginning of the USP DBD and codes for amino acids 104-507. The USPF2 insert was isolated using the forward primer (VP16-dUSPF2) 5' TTTT GAATTC TGCTCTATTTGCGGG-GATCGG 3' (SEQ ID NO: 16) with the same reverse primer.

A third insert, VP16-dUSPF3, coding for amino acids 170-507 lacks the USP DBD, and was generated using the forward primer having the sequence 5' TTTT GAATTC AAGCGC-GAAGCGGTCCAGGAG 3' (SEQ ID NO: 17) with the VP16-dUSPR primer.

PCR reactions were cycled according to the following protocol. An initial 5 minute melting step at 94° C. was used to yield single stranded template DNA. Temperature cycling proceeded as follows: 94° C. melting for one minute, 58° C. annealing for one minute, 68° C. extension for 2 minutes, and repeated 29 more times for a total of 30 cycles. The PCR products and the pVP16 vector were double digested with the EcoRI and the HindIII restriction enzymes, the samples were electrophoresed in a 1% agarose gel, and the appropriate bands were excised from the gel (Qiagen). The gel-extracted PCR products were ligated into the pVP16 vector using T4 Ligase (New England Biolabs) and the ligation mixture was added into 45 ul Ultracompetent XL10-Gold *E. coli* (Stratagene). The cells were then streaked onto Luria-Bertani (LB) agarose plates and transformants selected with ampicillin and grown in liquid culture, plasmid DNA was extracted and the vectors verified by restriction analysis and sequencing.

Construction of Ld Vectors

*Leptinotarsa decemlineata* (Ld) USP constructs were made by sub-cloning two different LdUSP inserts into the pVP16 vector (Clontech). This vector encodes a fusion protein of the herpes simplex virus 16 kDa viral protein (VP16) activation domain (AD) fused to LdUSP. The LdUSP portion of the fusion gene was isolated by PCR in two different lengths from a plasmid, pBSKS(+)-LdUSP. The forward primer pVP16-LdUSPII 5' TTTT GAATTC TGC TCG ATT TGC GGG GAC AAG 3' (SEQ ID NO: 18) and the reverse primer pVP16-LdUSPR 5' TTTT AAGCTT CTA AGT ATC CGA CTG GTT TTC 3' (SEQ ID NO: 19) (underlining designates the EcoRI and HindIII restriction sites, respectively) were used to amplify the LdUSPII fragment. The shorter LdUSPIII fragment, which lacks the Ld DNA binding domain (DBD) was generated using the forward primer pVP16-LdUSPIII 5' TTTT GAATTC AAG CGG GAG GCG GTT CAA GAA 3' (SEQ ID NO: 20) and the reverse primer. After an initial 4 min melting step at 94° C., PCR was used to amplify the inserts under the following cycling conditions: 94° C. melting for 1 min, 58° C. annealing for 1 min, 68° C. extension for 3 min, over 30 cycles.

The PCR products and the pVP16 vector were then double digested with EcoRI and HindIII restriction enzymes, and electrophoresed on a 1% agarose gel. The appropriate bands were excised from the gel (Qiagen) and ligated into the pVP16 vector using T4 ligase (New England Biolabs). After the ligation reaction, the samples were transformed into XL10-Ultracompetent *E. coli* (Stratagene) and streaked onto Luria-Bertani (LB) agarose with ampicillin. Transformants were grown in liquid LB medium with ampicillin and the DNA extracted (Qiagen). The vectors were verified by restriction analysis.

The pcDNA3.1(+)-LdEcRA vector was constructed in a similar fashion. The forward primer pcDNA3-LdEcRAF 5' TTTT GGATCC ACC ATG ACC ACC ATA CAC TCG ATC 3' (SEQ ID NO: 21) and the reverse primer pcDNA3-LdEcRR 5' TTTT TCTAGA CTA TGT CTT CAT GTC GAC GTC 3' (SEQ ID NO: 22) (underlining designates the BamHI and XbaI restriction sites, respectively) were used to amplify the LdEcRA fragment from the plasmid pBSKS(+)-LdEcRA. This PCR product was double digested using the BamHI and XbaI restriction enzymes then ligated into pcDNA3.1(+) (Invitrogen) and transformed as described previously.

Plasmid pBSKS(+)-LdEcRB1 was restriction digested with the XbaI and BamHI restriction enzymes to yield the LdEcRB1 fragment. The pcDNA3.1(−) plasmid (Invitrogen) was linearized using the same restriction enzymes. Both restriction products were electrophoresed on a 1% agarose gel. The appropriate sized bands were excised from the gel then ligated and prepared as described previously.

Example 4

JHIII Potentiates Ecdysteroid-Induced Transcriptional Activity in a Mammalian Cell Line Transfected with EcR In an initial series of studies, a GRdEcR chimera that consists of the rat glucocorticoid receptor (GR) activation domain attached to the EcR DBD and LBD (FIG. 1) was cotransfected along with mRXRα into CHO cells. The response of transfected cells to murA was measured using a $(EcRE)_5$-ΔMTV-CAT reporter plasmid that carries five tandem repeats of the hsp27 EcRE linked to the MTV (mouse mammary tumor virus) promoter and the chloramphenicol acetyltransferase gene (CAT).

Results of a typical experiment are shown in FIG. 2. Cotransfection with GrdEcR and RXR evoked a detectable response at dosages as low as 0.1 µM murA. It was found that juvenile hormone III (JHIII) potentiated the response of murA in a dose-dependent manner (using 20, 40, 80, and 160 µM JHIII) at submaximal murA dosages (0.1 µM and 1 µM murA) (FIG. 2, sets 2 and 3, respectively). JHIII did not display the ability to evoke a response that was greater than the maximal level induced by 10 µM murA. Despite the structural resemblance between the LBDs of EcR and the vertebrate FXR, which is highly responsive to JHIII alone (Forman et al., 1995), JHIII alone did not show an effect on transcription mediated by the GEcEc chimera (FIG. 2, set 1). Thus, this experiment shows that although JH by itself may not be able to evoke a EcR mediated response, JH can potentiate the effect of EcR ligands.

Example 5

Drosophila EcR Isoforms Display Different Capabilities in Mammalian Cells that Depend Upon Ligand and Heterodimeric Partner FIG. 3 shows the effects of murA, 20E, and JHIII on RLU activity induced by (EcRE)$_5$ΔMTV-LUC in CHO cells cotransfected with a *Drosophila* EcR isoform and VP16CfUSP where sets 1, 2, and 3 in the figure correspond to EcRA, EcRB1 and EcRB2, respectively. When tested with VP16CtUSP, all three *Drosophila* isoforms were induced by about 30-40 fold at 1 µM murA. The response of all EcR isoforms in the presence of VP16CfUSP was potentiated by the presence of 80 µM JHIII in the presence of 0.1 µM murA (FIG. 3). It was found that the effect was dose-dependent (data not shown) similar to the results seen with GEcEc (i.e., GRdEcR). The range of the normalized fold inductions for each experiment was found to vary by less than 15% for each experiment.

The *Drosophila* EcR isoforms and VP16CfUSP were also tested with 20E (FIG. 3). At a dosage of 10 µM 20E, all three constructs generated a consistent and discernible transcriptional response. Only the EcRB2/VP16CfUSP dimer (FIG. 3, set 3) was potentiated significantly by the additional presence of JHIII, however. That only the B2 EcR isoform is potentiated by JHIII in the presence of 20E indicates that JHIII potentiation may depend upon both the N-terminal domain of EcR and the activating ecdysteroid.

The results indicate that ligand-independent and ligand-dependent transcription as well as JHIII potentiation may depend upon an interplay of the EcR N-terminal domain, the activating ecdysteroid, and the heterodimeric partner. Thus, it was found that responsiveness of the natural EcR isoforms to 20E requires USP (rather than RXR) as a dimeric partner. Also, among the three isoforms (EcRA, EcRB1, and EcRB2), JHIII potentiation in the presence of 20E occurred only with the EcRB2 isoform and USP. Specific combinations of the EcR N-terminal domain and the heterodimeric partner (e.g. VP16 and RXR, B2 and USP) result in a functional receptor that is capable of showing an ecdysteroid response and/or JHIII potentiation. Levels of ligand-independent transcription also depend upon both the EcR N-terminal domain and the heterodimeric partner. The potentiation observed in the experiments cannot be attributed to the activation of RXR by either JHIII or a JHIII metabolite, since JHIII showed no activity by itself on the assays (Harmon et al., 1995; Saez et al., 2000).

Example 6

Assay of FXR Interaction with USP

It is known that the FXR/RXR heterodimer may respond to JHIII. Thus, a series of experiments were carried out to determine the ability of insect USP to mediate an ecdysteroid and/or JHIII response in conjunction with FXR.

The combination of FXR and USP evoked a low level response in CHO cells to JHIII (FIG. 4). The response observed is attributable to endogenous expression of low levels of RXR in these cells (data not shown). The addition of ecdysteroids (murA or 20E) with JHIII induced no elevation of FXR-mediated activity (FIG. 4). Also, USP was unable to potentiate a response to 20 µM CDCA (Chiang et al, 2000, *J. Biol. Chem.*, 275:10918-10924), the strongest activator of FXR known to date. In addition, EcR was unresponsive to CDCA alone or as a potentiator of murA response (data not shown). These experiments indicate that whereas EcR is able to interact with USP or RXR, and FXR interacts with RXR, FXR does not interact with USP to induce transcription. For FIG. 4, all activities are normalized log (fold inductions) based on RLU activity from a simultaneous run that was repeated twice and generated similar trends, though dosage levels varied.

Example 7

Evaluation of Compounds for Activity at the Farnesoid Receptor (FXR)

In these experiments, candidate juvenoids were tested for their ability to activate FXR mediated transcription by transfecting Chinese hamster ovary (CHO) cells using the FXR plasmid, mouse RXRα, and the ΔMTV-(EcRE)$_5$-CAT reporter as described herein. An RXR-dependent CRBPII-CAT reporter plasmid was employed in parallel assays to discern activators specific for this receptor.

A. FXR Responds to Endogenously-Produced Farnesol Metabolites

Farnesoid-like molecules define a metabolic pathway that begins with farnesyl diphosphate (Weinberger, C., 1996, *TEM,* 7:1-6). Thus, in these experiments, endogenously-produced metabolites of farnesol (50 µM FAC) were assayed as FXR effectors. Transcriptional activities ranged from 2-fold increases for farnesoic acid to 20-fold inductions for juvenile hormone III when tested at 50 µM.

Thus, nerolidol induced FXR-dependent CAT activity with a potency (EC$_{50}$=15 µM) and efficacy (9-fold induction) like its farnesol isomer. Alcohol and aldehyde dehydrogenases oxidize farnesol farnesal and farnesoic acid (Christophe, J. and G Popjak, 1961, *J Lipid Res.,* 2:244-257), which exhibited 2 to 3-fold activity increases in FXR mediated transcriptional activity, respectively. Insects and mammals transform farnesoic acid into methyl farnesoate (Schooley, D. A. and F C Baker, 1985, Juvenile hormone biosynthesis. In: *Comprehensive Insect Physiology, Biochemistry, and Pharmacology* Edited by G A Kerkut, L I Gilbert, vol. 7. pp. 363-389. Oxford: Pergamon Press; 1985: 363-389) which showed a 6-fold induction of FXR mediated transcription. Methyl farnesoate is epoxidized in insects to the FXR activator JH III, which induced CAT activity 15-fold. Thus, it was found that FXR responds variably to all endogenously-produced open chain sesquiterpenoid metabolites of farnesyl diphosphate in the biochemical pathway that extends from farnesol to JH III.

B. Juvenile Hormone Mimetics Induce FXR-Dependent Transcription

FXR-activating farnesoids have been described as JH agonists in insect bioassays (Schneiderman, H. A., and L I Gilbert, 1964, *Science,* 143:325-333). Like farnesol, nerolidol was effective as a juvenoid and as an FXR effector (Table 4). The chlorophyll metabolite phytol increased activity three times, thereby evincing marginal JH activity (Table 4). In contrast, neither the monoterpenes linalool (200 µM) nor geraniol were effective as FXR activators or juvenoids.

Synthetic juvenoids (Table 4) were also evaluated. The ethyl ester of 7,11-dichloro-2-ene farnesoic acid (ZR232) (Law, J. H. et al., 1966, *Proc. Natl. Acad. Sci. USA,* 55:576-578), induced CAT activity 5-fold when added at 50 µM. In addition, the synthetic juvenoids, methoprene and pyriproxyfen, increased FXR-dependent activity with efficacies like that produced by JH III (Table 4). These results indicate that FXR activates transcription in response to isoprenoids and chemicals previously reported to have insect JH activities.

Plant-derived JH agonists were also examined as FXR effectors. Farnesol-like echinolone, an essential oil of echinacea (Jacobson, M., et al., 1975, *Lloydia*, 38:473-476) maximally induced FXR-dependent activity 7-fold. Juvocimene (found in sweet basil) and juvabione (from balsam fir), two JH mimetics WS (Bowers, W. S. et al., 1966, *Science*, 154:1020-1; Bowers, W. S. and R Nishida, 1980, *Science*, 209:1030-1032), increased RXR mediated transcription 10-fold and 3-fold, respectively. Synthetic juvocimene (25 µM) increased FXR-dependent activity 5-fold. Also, α-bisabolol (50 µM), an analog of juvabione found in chamomile, increased activity 13-fold.

Certain olive oil vehicles have been distinguished as juvenoids in insect molting assays (Carlisle, D. B. and P. E. Ellis, 1968, *Science*, 162:1393-1394). Extra-virgin olive oil or its redolent tyrosine-like 2-, 3,- and 4-hydroxyphenethyl alcohol constituents (400 µM) all elevated FXR-dependent activity 3-fold. Unsubstituted phenethyl alcohol was inert at this dose. Activation of FXR by natural and synthetic JHs offers further evidence that FXR has functional attributes of an insect JH receptor.

C. FXR is Activated by Insecticide Synergists

The observation that sesame oil and its sesamin and sesamolin ingredients increased the toxicity of insecticides led to the development of synergist analogs like piperonyl butoxide (PB) and the description of these compounds as JH agonists (Bowers, W. S., 1968, *Science*, 161:895-7). PB and sesamin (100 µM) induced FXR-dependent activity 9-fold and 12-fold, respectively. Crude sesame oil (Sigma) maximally increased activity 3-fold; three commercial brands of toasted sesame oil were more effective, however, delivering maximal activities between 8-fold and 17-fold. Also, 4-fold induction was produced by 50 µM piperine, a PB analog from black pepper, as well as by myristicin and its p-dimethoxylated congener apiole in dill and parsley (both at 250 µM FAC). The sesamolin cleavage product sesamol was inactive at 400 µM FAC as were PB analogs with small side chains such as piperonyl alcohol, piperonylic acid, and safrole. These results indicate that FXR shares functional qualities similar to those expected of an insect JH receptor, and that the synergistic actions of PB and sesamin may partly reflect intrinsic JH activities.

D. FXR is a Target for Plant Secondary Metabolites

Commercially available oils from various plants were also examined as FXR effectors. For example, cedarwood oil and its redolent sesquiterpene α- and β-ionone isomers increased FXR-dependent activity with potencies and efficacies like those induced by farnesol (Table 5). It is known that sesamin blocks liver HMG CoA reductase activity, that farnesol is anti-proliferative, and that FXR is inhibited by the hypocholesterolemia-inducing plant steroid guggulsterone (Wu, J. et al., 2002, *Mol Endocrinol.*, 16:1590-7; Urizar, N. L. et al., 2002, *Science*, 296:1703-6). Given the reported biochemical activities for sesamin, farnesol, and FXR, phytochemicals previously reported to modulate plasma cholesterol levels or growth in mammals were tested as FXR effectors. The data are summarized by molecular class in Table 5.

i. Monoterpenes:

Given that FXR responds to endogenously-produced isoprenoids, plant-derived monoterpenes were examined for activity. Tea tree oil, which contains insecticidal terpinen-4-ol (40% of mass), 1,8-cineole (eucalyptol), and α-terpineol, maximally elevated FXR-dependent CAT activity 8-fold (Table 5 and FIG. 13A). Each of these constituents induced activity only two-fold at 800 µM, but notably 400 µM of any pairwise mixture increased activity like tea tree oil itself (FIG. 13A). Carvacrol and thymol (300 µM) in oregano inhibit tumor cell growth (Case, G. L. et al., 1995, *Lipids*, 30:357-9; Burke, Y. D. et al., 1997, *Lipids*, 32:151-6) and both induced CAT activity 6-fold (Table 5). Limonene in orange oil blocks tumors, inhibits HMG CoA reductase, and is being tested as a human chemotherapeutic agent (Crowell, P. L. and M. N. Gould, 1994, *Crit. Rev. Oncog.*, 5:1-22; Elegbede, J. A. et al., 1984, *Carcinogenesis*, 5:661-4.; and McNamee, D., 1993, *Lancet* 342, 801). Limonene and limonene oxide (400 µM) were inactive in activation of FXR, but either enantiomer of its metabolite perillyl alcohol induced FXR-dependent CAT activity 4-fold (Table 5). This dose matches that required to inhibit cell growth in culture (He, L. et al., 1997, *J. Nutr.*, 127:668-674). Finally, while menthol and fenchone (fennel) were inactive (0.5 mM), 0.5 mM fenchyl alcohol induced activity 5-fold, as did 0.5 mM pine tree-derived pinane diol (Table 5).

ii. Diterpenes:

Forskolin, one of the most robust FXR effectors yet described (Howard, W. C. et al., 2000, *Tox. Appl. Pharm.*, 163:195-202), increased activity more than 100-fold when added at 2 µM. Like forskolin, 1-trans-$\Delta^9$-tetrahydrocannabinol (THC) from the cannabis plant contains a tricyclic ring. In addition to their psychoactive effects, cannabinoids block cell growth, inhibit DNA synthesis, and lower the incidence of spontaneously-arising mouse liver tumors (Carchman, R. A., et al, 1976, *Cancer Res.*, 36:95-100; Munson, A. E. et al, 1975, *JNCI*, 55:597-602). A 5-fold increase in FXR-dependent CAT activity was elicited by 15 µM THC, but not by its $\Delta^8$-isomer or by cannabinol (Table 5). Abietic acid (100 µM), another forskolin-like diterpene in ginko, spruce, and fir, induced CAT activity 50-fold (Table 5). FXR-dependent activity was also increased 3-fold by tumor-promoting croton oil at the highest non-cytotoxic dose. Phorbol-like diterpenes from croton tiglium and related plants such as phorbol 12,13-dibutyrate, mezerein, and ingenol 3,20-dibenzoate, increased activity 2, 3, and 5-fold, respectively, when added at 10 µM (Table 5). Phorbol and ingenol were inactive.

The palmitate esters of cafestol and kahweol have been identified as the mediators of the hypercholesterolemic effects of coffee in humans (but not in other primates or rodents) (see e.g., Weusten-Van der Wouw, M. P. et al., 1994, *J. Lipid Res.*, 1994, 35:721-735). Cafestol, kahweol and their acetate derivatives (20 µM) induced FXR-dependent CAT activity between 10- and 20-fold (FIG. 13B and Table 5). At this dose, the major diterpenoid-fatty acyl ester in coffee oil, cafestol palmitate, was inert.

iii. Triterpenes.

Resin from *Commiphora molmol* (myrrh) exhibits insecticidal activity in lepidoptera (Shonouda, M. L. et al., R M Farrag, O M Salama, 2000, *J Environ Sci Health B*, 35:347-56). FXR was activated by essential oils from myrrh and frankincense with maximal inductions approaching 20 times more than vehicle (Table 5). Some of the FXR-dependent activity promoted by frankincense is derived from triterpenoid components, β-boswellic acid and oleanolic acid (25 µM), which increased activity 11- and 3-fold, respectively (Table 5). Ursolic acid is a rosemary ingredient related to oleanolic acid that inhibits mouse skin tumors (Huang, M. T. et al., 1994, *Cancer Res.*, 54:701-708; Nishino, H. et al., 1988, *Cancer Res.*, 48:5210-5215). While rosemary oil maximally induced FXR-dependent activity 12-fold (Table 5), ursolic acid (50 µM) was ineffective as were its polyketide constituent rosemarinic acid and its curcumin congener.

Cucurbitacins are phytoecdysteroids that inhibit ecdysone receptor (EcR) function (Dinan, L. et al., 1997, *Biochem J.*, 327:643-50). Cucurbitacin D (1 µM) suppressed FXR-dependent activity promoted by JH III and CDCA (40 µM each), 7- and 58-fold, respectively (FIG. 13C). The $\Delta^1$-unsaturated congener cucurbitacin I also inhibited farnesol-induced activity with an $IC_{50} \sim 50$ nM (data not shown). The 22-oxo-$\Delta^{23}$-ene group of cucurbitacin is critical for EcR antagonist activity, allegedly by forming covalent adducts between its $\alpha,\beta$-unsaturated carbonyl group and amino acids in the EcR ligand binding domain (Dinan, L. et al., 1997, *Biochem J.*, 327:643-50). 22R-Hydroxycholesterol is metabolized in mammals to pregnenolone via a 20,22-dihydroxycholesterol intermediate with an apparent $K_m$ of 7 µM (Sugano, S., et al., 1966, *J Biochem (Tokyo)* 1996, 120:780-7). Coincidentally, FXR-dependent transcription was induced 10-fold by 20$\alpha$- or 22R-hydroxycholesterol (7.5 µM), but not by 22S-hydroxy-, 7-keto-, or 7$\alpha$-hydroxycholesterols (data not shown). It is possible that the 20,22-dihydroxy group can be metabolized to the 22-oxo-$\Delta^{23}$-ene functionality in insects and mammals to generate EcR or FXR antagonists.

iv. Furocoumarins and Phenylpropanoids.

Figure 13D:
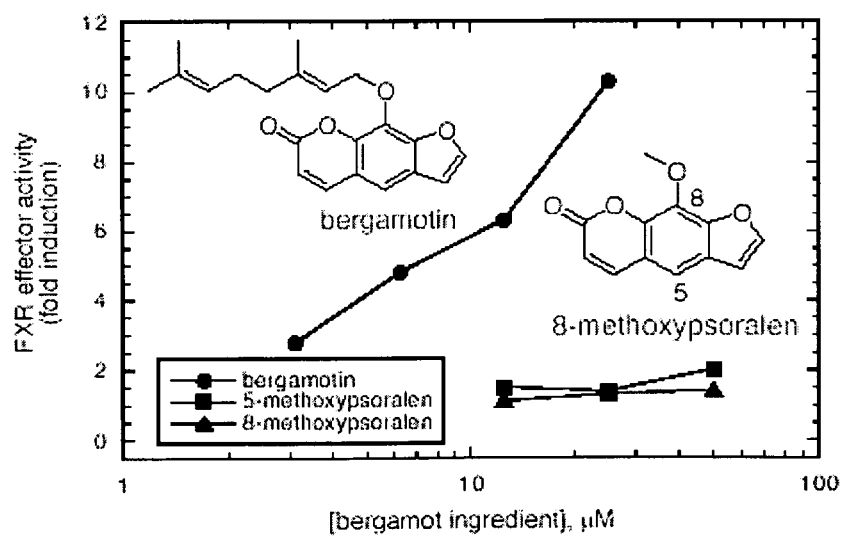
Figure 13E:
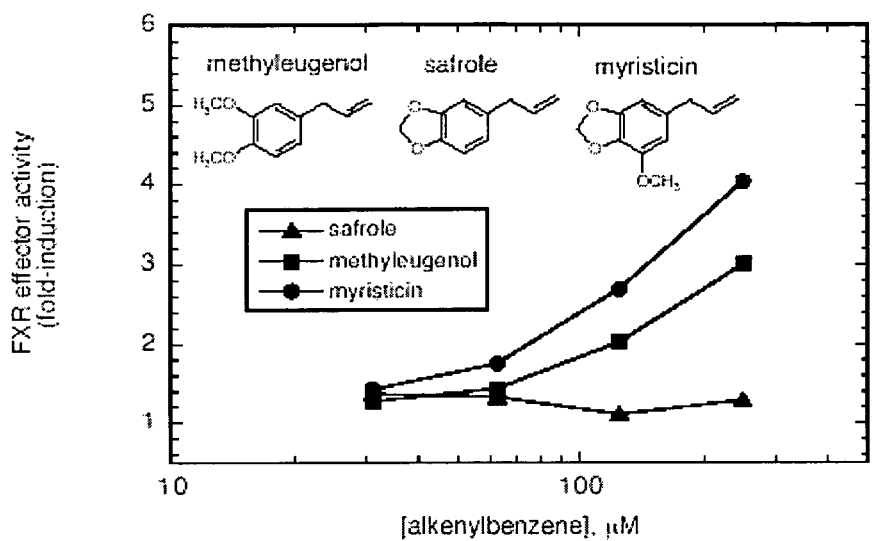

The Earl Grey tea flavoring bergamot oil and its constituent bergamotin, which possesses a geranyl group, both induced CAT activity 8-fold when tested at 25 µM (Table 5 and FIG. 13D). The unprenylated bergamot ingredients bergapten (5-methoxypsoralen) and its hepatocarcinogenic 8-methoxylated psoralen congener were inactive at 50 µM (FIG. 13D). Also, methylenedioxyphenyls like myristicin and apiole in dill and parsley weakly elevated CAT activity 4-fold at 250 µM, but their congener safrole, a rodent liver carcinogen (Miller, E. C. et al., 1983, *Cancer Res.*, 43:1124-34), was inert (FIG. 13E). While the alkenylbenzenes eugenol and caffeic acid were also inactive, methyleugenol, a multi-site rodent carcinogen (Johnson, J. D., et al., *J. Agric. Food Chem.* 2000, 48:3620-3632) found in nutmeg and other plants, induced FXR-dependent activity 4 times more than vehicle at this same dose (FIG. 13E).

v. Coumarins and Flavanoids.

The flavolignin silybin from milk thistle (silymarin) induces macromolecular synthesis in the hepatectomized rodent liver (Fausto, M. and J. Sonnenbichler, 1977, *Hoppe-Seyler's Z. Physiol. Chem.*, 358:141-147), arrests cells in the $G_1$ phase of the cycle (Zi, X. and R. Agarwal, 1999, *Proc. Natl. Acad. Sci. USA*, 96:7490-7495), and shows anti-proliferative effects (Katiyar, S. K. et al., 1997, *J. Natl. Cancer Inst.*, 89:556-66). Silybin increased FXR-dependent activity 18-fold at 50 µM (Table 5). While silymarin lowers cholesterol better than silybin (Krecman, V. et al., 1998, *Planta Med.*, 64:138-42), FXR activity was maximally increased only 4-fold by the former (data not shown). FXR may respond to other analogs of silybin in milk thistle such as silydianin, silychristin or their metabolites. Taxifolin is one silymarin component that has been shown to inhibit HMG CoA reductase activity in hepatocytes (Theriault, A., et al., 2000, *J. Lipid Res.*, 41:1969-1979). FXR was unresponsive to taxifolin or to other flavonoids such as genistein, quercetin, catechins, and gossypetin (50 µM). However, activity was increased 4-fold in response to the same dose of tangeretin, a methoxylated flavone in citrus fruits.

Figure 13F:
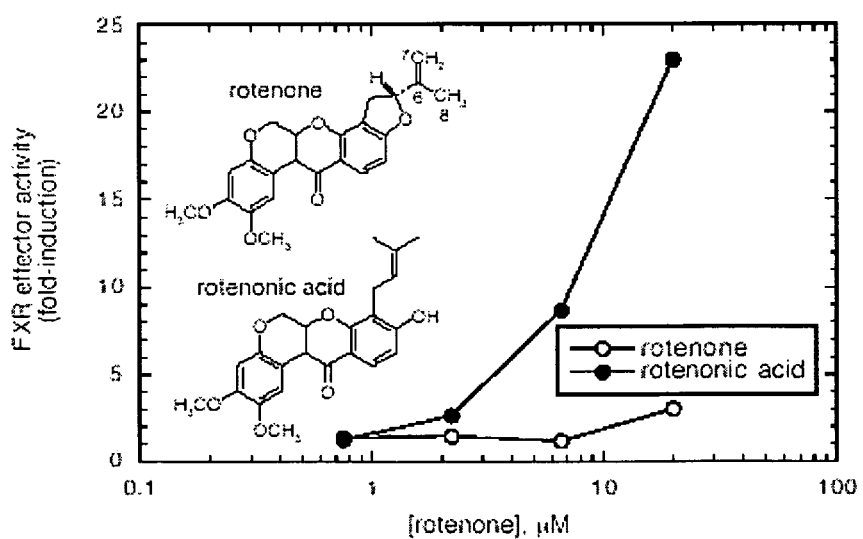
Figure 13G:
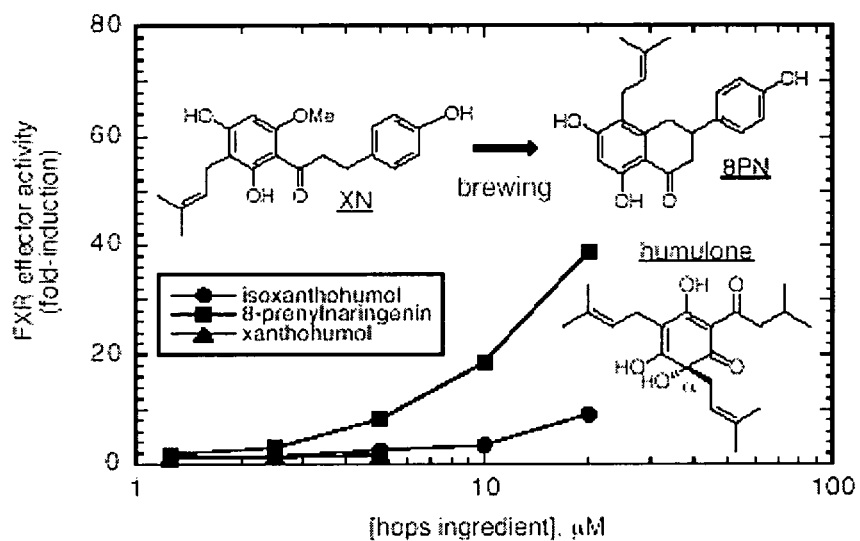
Figure 13H:
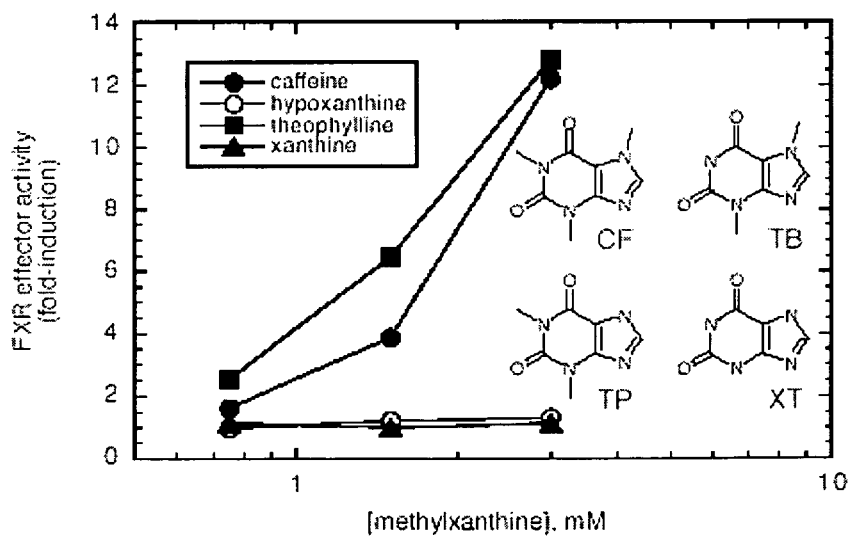

The insecticidal actions of the derris plant flavonoid-like component rotenone allegedly result from its ability to inhibit electron transport and respiration (Chance, B., and G. Hollunger, 1963, *J. Biol. Chem.*, 278:418-431). Rotenone also reduces the incidence of spontaneously-arising liver tumors in male mice. These findings animated a test of rotenone as an FXR effector. Rotenone was inactive (FIG. 13F), but its rotenonic acid derivative with a cleaved furan ring, induced FXR-dependent activity 20-fold when added at 20 µM (FIG. 13F). This may have some functional significance since metabolites of rotenone such as 6',7'-dihydro-6',7'-dihydroxyrotenone and 8'-hydroxyrotenone, which are hydroxylated in the proximity of the furan ring, can be generated using microsomal homogenates prepared from either insect or rodent tissues (Fukami, J. I. et al., 1967, *Science*, 155:713-6).

vi. Linoleic Acid Metabolites.

An oil extract of ylang ylang, which emits a jasmine-like aroma, maximally increased FXR-dependent activity 17-fold (Table 5). One of its components, cis-jasmone, a linoleic acid metabolite and defensive signal that is released by plants following herbivore damage (Birkett, M. A. et al., 2000, *Proc. Natl. Acad Sci. USA*, 97:9329-9334), elicited a 6-fold increase in activity when added at 1 mM (Table 5). An identical dose of jasmonic acid had no effect, but a 17-fold increase was produced by its methyl ester (Table 5). Due to their volatilities, it is anticipated that the high doses of jasmonoids required for FXR activation in cell culture may not correspond to the doses that mediate attractant, repellant, or insecticidal activities in the animal.

vii. Polyketides.

Since an extract of hops maximally induced FXR-dependent activity 18-fold, some individual components were tested. The flavanone 8-prenylnaringenin and its methylated isomer isoxanthohumol (20 µM) elicited 38- and 9-fold increases in activity, respectively (FIG. 13G and Table 5). However, FXR was not activated by xanthohumol, the chalcone precursor to isoxanthohumol that is produced during beer brewing (FIG. 13G). Humulone increased activity 8-fold, but lupulone, a structurally-related hops ingredient with an additional isoprenyl group, was inert (Table 5, both tested at 20 µM).

xiii Xanthines.

FXR activation by forskolin animated tests of other plant compounds that modulate cAMP levels. FXR-dependent activity was induced 12-fold by 3 mM theophylline or caffeine, but congeners such as theobromine, hypoxanthine, xanthine, adenine, and the cAMP metabolite 5'-AMP were ineffective (FIG. 8H and data not shown). Modest (4-fold) increases in CAT activity were afforded by 8-Br-cAMP or dibutyryl cAMP (1 mM). However, mixing theophylline (3 mM) with 8-Br-cAMP (1 mM) increased activity more than 100-fold like forskolin itself (data not shown). The FXR-activating theophylline dose matches its concentration (4 mM) in tobacco hornworm larvae three days after eating tomato leaves sprayed with 1% theophylline, a dose that reduces leaf consumption by half (Nathanson, J. A., 1984, *Science*, 226:184-7). Given that caffeine and theophylline are present in coffee beans and tea leaves at concentrations that kill *Manduca larvae*, xanthines may function as natural insecticides (Nathanson, J. A., 1984, *Science*, 226:184-7).

In summary, the foregoing experiments indicate that FXR activates transcription in response to a broad range of plant secondary metabolites, which were previously described as insecticides or as modulators of cholesterol or growth in higher metazoans.

E. FXR is Activated by Diverse Class of Man-Made Insecticides

FXR activation by plant-derived JHs and secondary substances provoked tests of man-made insecticides. Its sodium channel-based toxicity notwithstanding (Soderlund, D. M.,: 1985, *Neurotoxicology*, 6:35-46), a pyrethrum extract of chysanthemum flowers maximally induced FXR-dependent activity 13-fold. Candidate active ingredients are the structurally-related cinerins, pyrethrins, and jasmolins since FXR was induced by synthetic pyrethroids (25 µM) including cypermethrin (15-fold induction), permethrin (5-fold induction), phenothrin (8-fold induction), and bioallethrin (14-fold induction) (Table 6).

Organochlorine insecticides (5 µM) such as o,p-DDT (but not p,p-DDT), chlordane, kepone, lindane, dieldrin, and toxaphenes increased CAT activity 3, 7, 12, 5, 17, and 9-fold, respectively (data not shown). Other organochlorines like aroclor 1254 (5 µM) and 2,3,7,8-tetrachlorodibenzo-p-dioxin (100 nM) increased activity 5 and 15-fold, respectively (data not shown). FXR was activated by organophosphates such as malathion, diazinon, chlorpyrifos, and parathion (25 µM) with potencies and efficacies like farnesol (Table 6). Others like ethion and coumaphos were more efficacious and more potent, exhibiting 50- and 16-fold increases in activity, respectively, when tested at 5 µM. Lower molecular weight insecticides phosdrin, carbaryl, and imidan were inactive. Phenylpyrazoles such as chlorfenapyr which lowers ATP levels and structurally-related fipronil that distinctively blocks chloride channels increased FXR-dependent activity 10- and 20-fold, respectively, at 25 µM (FIG. 14). FXR was unaffected by imidacloprid, a nicotine-like compound that interferes with acetylcholine receptor function. These results indicate that FXR may activate transcription in response to structurally-diverse synthetic chemicals that manifest pleiotropic cytotoxicities through equally disparate mechanisms.

F. FXR May Be Inhibited or Activated by a Metabolite of the JH Antagonist Precocene Chromene ring-containing precocenes are plant-derived JH antagonists that hasten insect metamorphosis (Bowers, W. S. et al., 1976, *Science*, 193:542-7). Like safrole and other alkenylbenzenes, the precocenes are rodent hepatocarcinogens (Wiseman R. W. et al., 1987, *Cancer Res.*, 47:2275-83). Their alkylation of DNA and proteins and their metabolism to 3,4-diols hinted that precocenes may form reactive epoxides (Brooks, G. T., et al., 1979, *Nature*, 281:570-572; Pratt, G. E., et al., 1980, *Nature*, 284:320-323). To more firmly establish a role for FXR as a functional homolog of an insect JH receptor, precocene could was tested for its ability to function as an FXR antagonist. Instead of acting as an antagonist, precocene I and its 6,7-dimethoxy congener precocene II (both from Sigma-Aldrich) induced FXR-dependent activity 15-fold, but with reduced potencies ($EC_{50}$=150 µM) compared to farnesol. Precocene I was inactive in RAR, RXR, PPAR, or GR-based transcriptional assays, which suggests that it may be relatively specific for FXR (data not shown).

Different lots of precocene induced FXR-dependent activity with varying efficacies, prompting further analysis by thin layer chromatography (TLC). UV-absorbing material eluted from silica was tested for CAT activity and analyzed gas chromatography and mass spectrometry following trimethylsilane derivatization. Non-polar species corresponding to precocene I ($R_f$=0.44; m/z=190) did not affect FXR, but a more polar dimer ($R_f$=0.27; m/z=380) increased activity 22-fold. Its structure was inferred from the observation that FXR was activated by 5,11-dimethyltetrahydrochrysene, but not by its 6,12-dimethyl congener (Meyers, M. J. et al., 1999, *J Med Chem* 1999, 42:2456-68). The most polar species ($R_f$<0.16) elevated activity 12-fold and had molecular weights consistent with hydroxylated precocenes. These likely arose by silica gel-catalyzed air oxidation since they were not detected by GC/MS in the crude sample prior to TLC. Precocene I (25 mg, Sigma-Aldrich, 99% purity) was separated by thin layer chromatography using hexane-ethyl acetate (9:1) as the mobile phase. Aliquots (1× and 3× doses) were tested for FXR effector activity in parallel.

Given that FXR did not respond to the 3,4-diol or its precursor epoxide (data not shown) and that insects and mammals produce other hydroxylated species, experiments were performed to determine whether precocene could be metabolized to some other FXR effector. Incubations with mouse liver microsomes yielded ethyl acetate-extractable material that induced FXR activity 3-fold, which hinted at the presence of some liver activators such as farnesol or bile acids. In these experiments, NADPH and either DMSO and 100 µM precocene I were mixed with CD-1 mouse liver microsomes and incubated at 37° C. for one hour. Reaction products were extracted with ethyl acetate, dried, resuspended in DMSO, and tested for FXR effector activity. Parallel microsome incubations with 100 µM of TLC-purified inert precocene I ($R_f$=0.44; m/z=190) generated ethyl acetate-soluble products that reduced this activity by 70%. Since precocene II is O-demethylated (Soderlund, D. M. et al., 1980, *J. Agric. Food Chem.*, 1980, 28:724-731) and 6,7-methylenedioxyprecocene is not a JH antagonist (Bowers, W. S., 1969, Toxicology of the precocenes. In: *Insecticide Mode of Action* Edited by J R Coats. New York: Academic Press; 1969), it was surmised that the 6,7-catechol is the FXR antagonist produced by microsomes. Precocene I and precocene II are metabolically interconverted by methylations and demethylations. Support for this conjecture came from the finding that the FXR activity induced by farnesol was inhibited 44% by 100 µM esculetin, an analog of precocene with a similarly positioned 6,7-catechol. In these experiments, increasing amounts of esculetin were added along with 45 µM farnesol to CHO cells transfected with plasmids that express FXR and mouse RXRα, along with a ΔMTV-(EcRE)$_5$-CAT reporter plasmid. Normalized CAT activities are expressed as mean values±standard deviation calculated from triplicate well samples. The ineffectiveness of esculetin and its analog 7-hydroxy-6-methoxycoumarin as FXR agonists and the ability of 7-methoxycoumarin (all at 1 mM) to increase activity 10-fold emphasize the specificity of congeners. FXR was activated by other precocene-like JH antagonists including 3,4-dimethoxy-6-isopentenylphenol (3-fold induction at 100 µM) and a tricyclic dichromene (29-fold induction at 25 µM). It has been proposed that, like preocene, these suicide substrates disrupt metamorphosis by covalently binding to nucleophilic DNA or proteins following their oxidation to epoxides, catechols, or quinone methides (Bowers, W. S. et al., 1976, *Science*, 217:647-648). Since P450 metabolism may be impaired in cultured cells, it is not entirely unexpected to find that precocene and analogs did not inhibit FXR-dependent activity in the CHO cell-based assay.

Additional experiments were performed to determine whether analogs of precocene function as potential endogenously-produced FXR antagonists. Ubiquinone-1 (U1) with a single isoprene unit is a congener of decaprenylated U10 (coenzyme Q), which functions in electron transport. At 10 µM, U1 completely inhibited farnesol-induced FXR-dependent activity. In contrast, di-, tri-, and tetraprenylated ubiquinones (U2, U3, and U4) increased activity 7, 5, and 3-fold, respectively (data not shown). U6, U8, U9, and U10 were inactive (data not shown). U2, U3, and U4 are detected in bacteria and U6 is found in yeast (Daves, G. D. et al, 1967, *Biochemistry*, 6:2861-2866). However, only U9 and U10 have been reported in insects and mammals (Olson, R. E., 1966, *Vitam Horm.*, 24:551-74). U1, U2, U3, and U4 have not been measured in mammals and hence their physiological significance is not known. Nonetheless, these results illustrate how in situ-generated electrophilic metabolites of precocene may antagonize the effects of JHs via interactions with an FXR homolog in insects.

Example 8

Ecdysone Receptor Activity is Potentiated by JHs and Insecticides

Figure 15A:
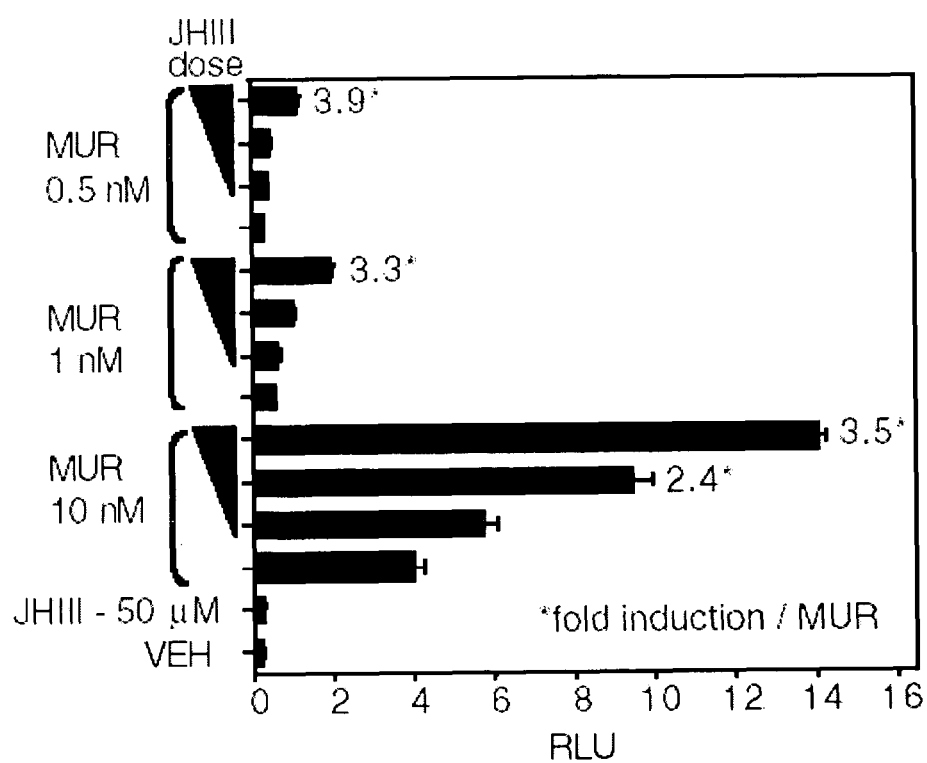
FIG. 15 shows that transcriptional activity programmed by muristerone-primed ecdysone receptors may be potentiated by juvenile hormones and insecticides in accordance with example embodiments of the present invention where: (15A) shows potentiation of ecdysone receptor activity by JH III, where muristerone A (MUR) was added at the indicated doses in ethanol vehicle, and increasing amounts of JH III (12, 25, or 50 μM) were added (underlying triangles), and numbers over bars indicate the ratio of the GEcEc-dependent activity produced by 50 μM JH III in the presence of the indicated dose of MUR to the activity produced by MUR alone; (15B) shows that JH III activity may require both EcR and RXR; (15C) shows that the JH agonist juvocimene from basil may be an EcR effector molecule where muristerone A (0.2 μM) was added alone or with 10 or 20 μM juvocimene (J) to GEcEc-transfected cells, and farnesol (farn) (45 μM) or juvocimene was added to FXR-transfected cells; (15D) shows that insecticides may potentiate EcR-dependent transcriptional activity in the presence (+) or absence (−) of muristerone A, where cells were incubated with the indicated natural and synthetic insecticides (added at 25 μM, except endosulfan which was added at 5 μM), where the numbers above the bars indicate the ratio of activity from cells treated with insecticide plus MUR divided by that treated with MUR alone (fold-induction).
Figure 15B:
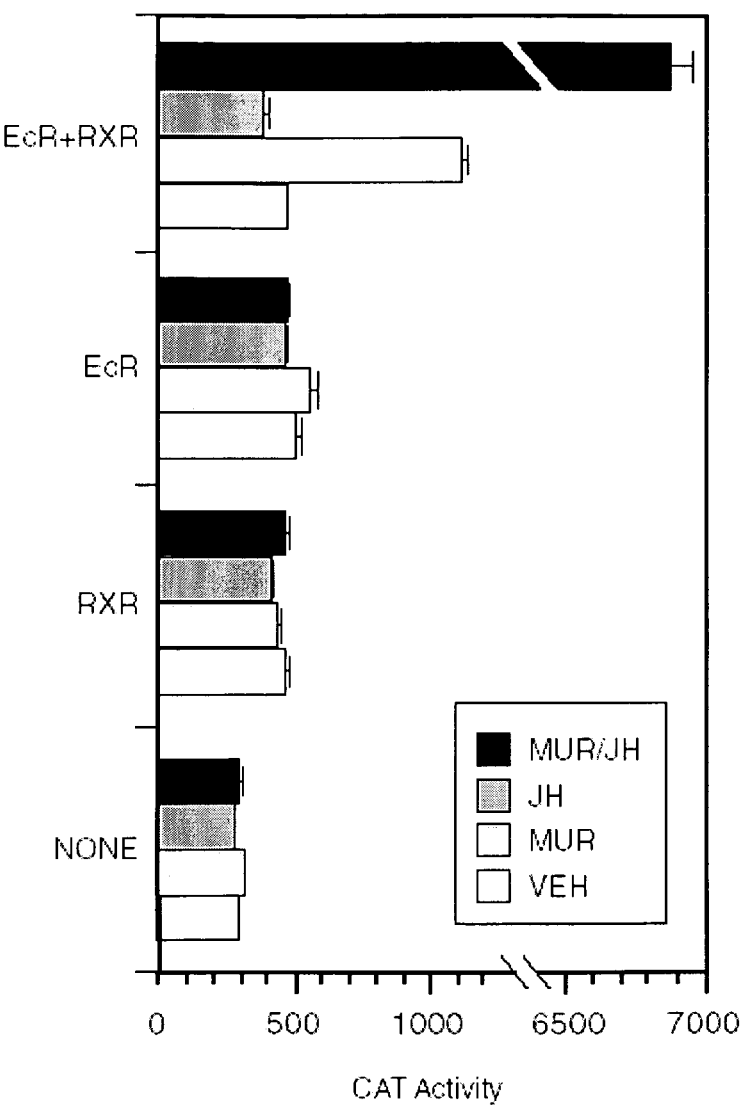

The activation of FXR by natural and synthetic JHs and its inhibition by precocene indicated that FXR may have pharmacological features of a long-postulated insect JH receptor. The prominent candidate for this JH-responsive macromolecule in insects is the structurally-related ecdysone receptor (EcR). Like FXR, EcR heterodimerizes with RXR and binds to the hsp27 ecdysone-responsive DNA element (Forman et al., 1995), but distinctively activates transcription in response to muristerone A (MurA or MUR), a synthetic ecdysone (Yao et al., 1992). Despite these similarities, a MurA-inducible chimeric receptor (GEcEc), constructed by fusing the human glucocorticoid receptor (GR) amino-terminus to the *Drosophila* EcR DNA and ligand binding domains, failed to respond to 80 µM JH III (FIG. 15A). In the experiments shown in FIG. 15A, muristerone A (MUR) was added at the indicated doses in ethanol vehicle, and increasing amounts of JH III (12, 25, or 50 µM) were added (underlying triangles). Numbers over bars indicate the ratio of the GEcEc-dependent activity produced by 50 µM JH III in the presence of the indicated dose of MUR to the activity produced by MUR alone. Relative light units (RLU) from firefly luciferase in cell lysates are expressed relative to renilla luciferase (Promega).

Given that JHs modulate ecdysone actions, it was originally anticipated that JH III might antagonize MurA inducible GEcEc-dependent signaling. In contrast, and as discussed above, the GEcEc-dependent transcriptional activity induced by MurA was increased 3-times more by the addition of 80 µM JH III (FIG. 15A). The effect was seen with as little as 0.5 nM MurA, an amount of MurA that barely elevated activity by itself. Similar JH III-mediated increases were afforded by higher doses of MurA (1 and 10 nM, FIG. 15A). Thus, farnesol (45 µM) elicited a 4-fold increase in activity over that provided by MUR alone. In the experiments shown in FIG. 15B, CHO cells were separately transfected with plasmid DNAs that express mouse RXRα or GEcEc (1.25 µg plasmid DNA per well), or transfected with both plasmids or none. MUR was added to cells at 10 nM and JH III at 50 µM. Normalized CAT activity was determined by measuring β-galactosidase activity produced by cotransfected SV40-β-gal plasmid DNA. Note that the ordinate axis is broken. The potentiative effect was also seen using a VP16-*Chironomus* Usp substituted for its mammalian homolog RXR (data not shown). Also, both RXR and GEcEc were essential for activity (15B).

Given that EcR responds to farnesol and JH III, other FXR-activating natural and synthetic JHs and insecticides were tested. For the experiments shown in FIG. 15C, CHO cells were transfected with rat FXR and mouse RXRα or GEcEc and mouse RXRα as described in Methods. Muristerone A (0.2 µM) was added alone or with 10 or 20 µM juvocimene (J) to GEcEc-transfected cells. Farnesol (45 µM) or juvocimene was added to FXR-transfected cells. Mean CAT activity is displayed±standard deviation from triplicate well samples. Juvocimene, sesamin, and piperonyl butoxide (25 µM) potentiated the MUR-inducible GEcEc-dependent activity between two and four times (FIG. 15C and data not shown).

Figures 15C, 15D:
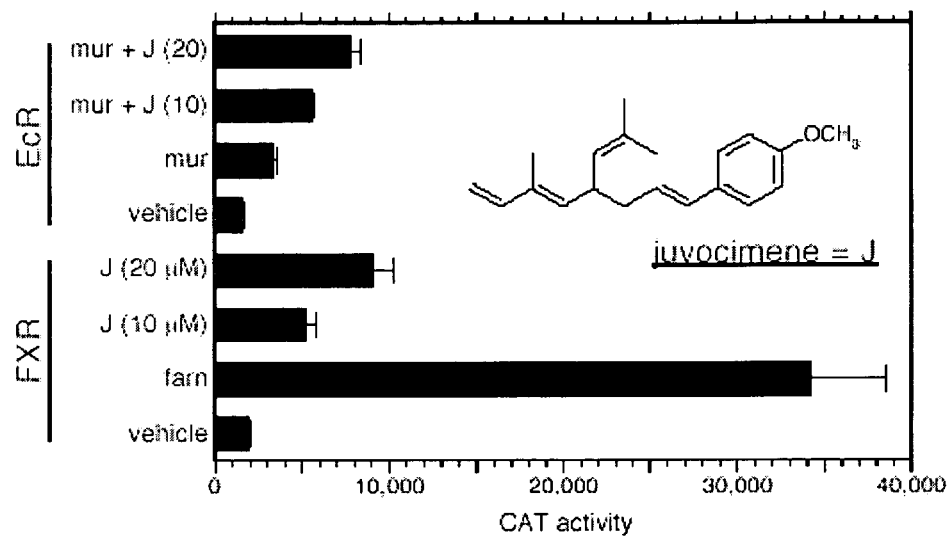

Also, GEcEc-dependent activity was induced between two and three times by other insecticides (25 µM) including diazinon, endosulfan (5 µM), coumaphos, permethrin, and precocene, while 25 µM chlorpyrifos potentiated the MUR response nine times (FIG. 15D). For the experiments shown in FIG. 15D, triplicate wells of CHO cells were transfected with GEcEc and RXR, after which muristerone A (MUR) was added at 10 nM in ethanol vehicle. Cells were incubated with the indicated natural and synthetic insecticides (25 µM), except endosulfan which was added at 5 µM. Plus and negative signs refer to MUR addition. Numbers above bars indicate the ratio of activity from a lysate of cells treated with insecticide plus MUR divided by that treated with MUR alone.

Although FXR and EcR exhibit substantial homology, FXR was unresponsive to muristerone A, ecdysone, or 20-hydroxyecdysone. Reciprocally, the FXR activator chenodeoxycholic acid (CDCA) did not induce GEcEc (data not shown). Thus, it appears that EcR and FXR may both activate transcription in response to natural and synthetic JHs and insecticides, but that the two receptors may not be seamlessly interchangeable.

Example 9

JH and Insecticide Effects Mediated Via FXR and EcR Ligand Binding Domains

The ligand binding domains (LBDs) of nuclear receptors map to their carboxyl termini (Kumar and Thompson, 1999, *Steroids*, 64:310-9). To ask whether JHs and insecticides transduce their effects via their putative LBDs, chimeric receptors that link the GR DNA binding domain (DBD) to the carboxy-terminal regions of FXR or EcR were examined.

EcR/GR Chimeras

For these experiments, the luciferase reporter construct was used. To obviate influences from other transcription factors, results were normalized using a reporter plasmid from which CAT expression is driven by a minimal promoter consisting of dimerized GREs linked upstream of a 13 base pair TATA box DNA element derived from the adenovirus E1B gene.

Figure 16A:
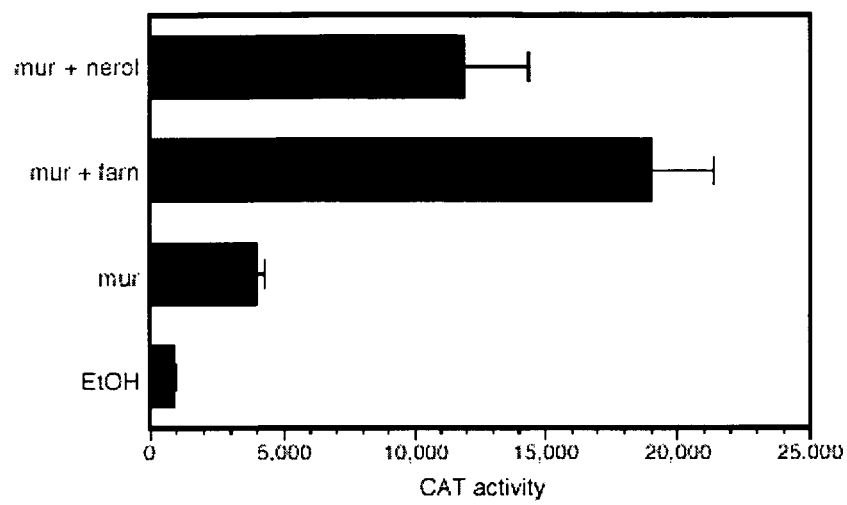
FIG. 16 shows that EcR and FXR ligand binding domains may mediate the transcriptional effects of juvenile hormones and insecticides in accordance with an embodiment of the present invention where: (16A) shows GGEc chimeric receptor activation in the presence or absence of 0.2 μM muristerone A (mur) by farnesol (farn) (25 μM) and its nerolidol isomer; (16B) shows that juvocimene may potentiate muristerone-primed GEcEc and GGEc-dependent activity; (16C) shows that GGEc may mediate the transcriptional effects of the FXR effector ubiquinone-2 (U2); (16D) shows that GGF chimeric receptor-dependent activation is increased by RXR where CHO cells were transfected with the indicated combinations of FXR- or RXR-expressing plasmid DNAs and chenodeoxycholic acid (CDCA) was added at a final dose of 40 μM (+) or is absent (−); and (16E) shows that the chimeric plasmid GGF is activated by the natural and synthetic insecticides cypermethrin, diazinon, dieldrin, precocene, methyl jasmonate, and abietic acid added at final doses of 25 μM.

The MUR-inducible GR/EcR hybrid, GGEc, that fuses the rat GR amino terminus and DBD to the *Drosophila* EcR LBD (Christopherson et al., 1992) induced transcription between two and four times more with 50 µM farnesol, its isomer nerolidol, or diazinon than with 0.2 µM MUR alone (FIG. 16A). In this experiment, GGEc and RXR were transfected into CHO cells with either a CAT or a luciferase reporter plasmid containing 1.5 kilobase pairs of the glucocorticoid-inducible mouse mammary tumor virus (MTV) promoter. Farnesol was added at 25 µM with or without 0.2 µM muristerone A. Normalized CAT activities are mean±standard deviation as measured from lysates sampled from triplicate wells. Like GEcEc, this activity required an RXR-expressing plasmid (data not shown).

Figure 16B:
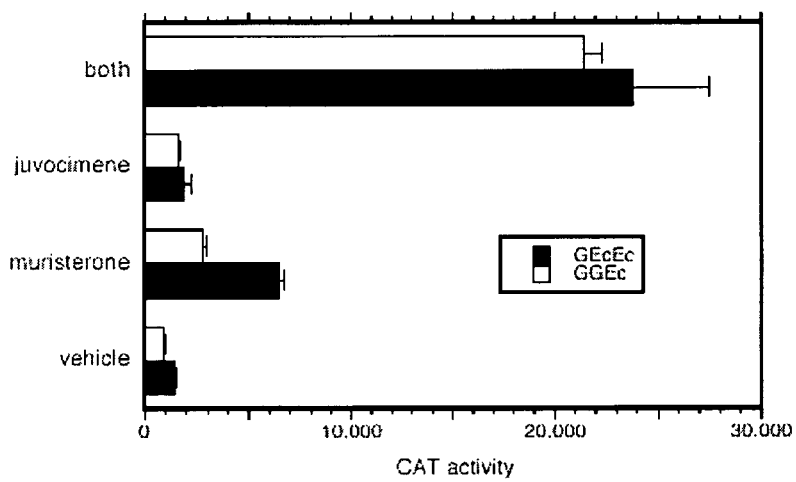

As seen for FXR, GGEc responded to juvocimene (20 µM), the JH mimetic from basil, by increasing activity 7 times more than MUR (FIG. 16B). In these experiments, CHO cells were transfected with a GGEc-expressing plasmid, a mouse RXRα expression plasmid, and an adenovirus E1b TATA-(GRE)$_2$-CAT reporter plasmid. The GGEc plasmid was eliminated from DNA mixtures added to cells transfected in parallel. CAT activities were measured from lysates of cells from triplicate wells treated with ethanol vehicle, juvocimene (20 µM), muristerone A (0.2 µM), or both.

Figure 16C:
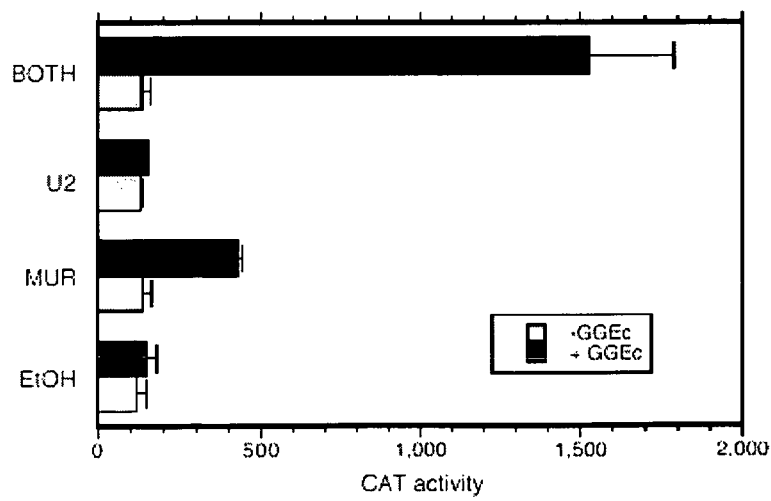

Functional harmony for FXR and EcR was underscored by the observation that the FXR effector ubiquinone-2 (10 µM) similarly increased GGEc-dependent activity 7 times more than MUR (FIG. 16C). In these experiments, CHO cells were transfected with DNAs as described above but ubiquinone-2 (10 µM) was substituted for juvocimene. None of the compounds tested in FIG. 16A, 16B, or 16C were effective in the absence of ecdysone.

FXR Chimeras

Figure 16D:
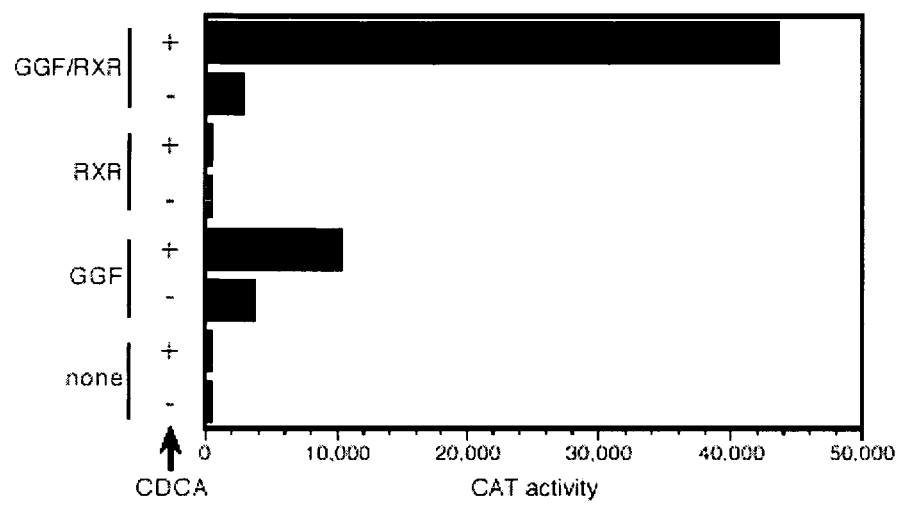

A plasmid was constructed that expresses a hybrid protein (GGF) consisting of the human GR amino terminus and DBD linked to the carboxyl terminus of FXR. GGF-dependent transcriptional activity was increased 3- and 15-fold by farnesol and CDCA (40 μM each), respectively (FIG. 16D). The limited GGF-dependent induction by farnesol was doubled by cotransfecting an RXR-expressing plasmid (FIG. 12D). Importantly, no activity was detectable without GGF.

Figure 16E:
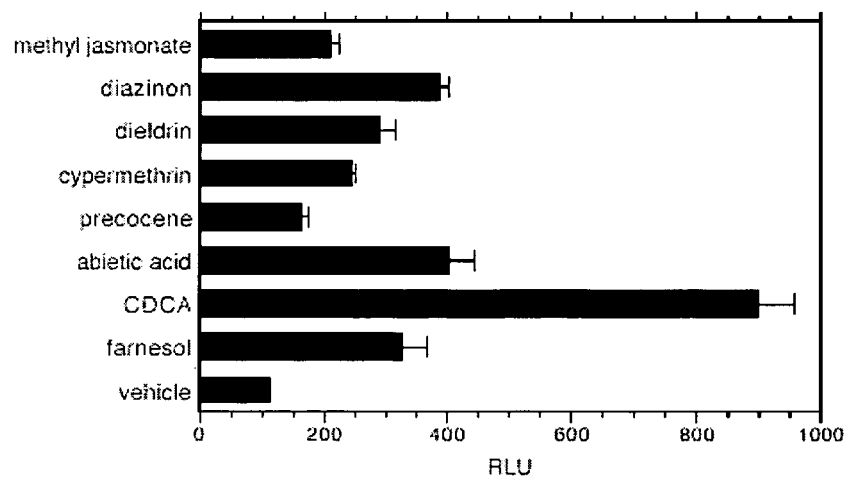

As shown in FIG. 16E, this FXR-like responsiveness led to tests of natural and synthetic insecticides as GGF effectors. In these experiments, CHO cells were transfected with receptor plasmids expressing GGF and mouse RXRα and a luciferase reporter plasmid containing the upstream 1.5 kbp of the MTV promoter. GGF-dependent activity was stimulated between 2- and 7-fold in response to micromolar doses (e.g., 25 μM) of cypermethrin, diazinon, dieldrin, fipronil, piperonyl butoxide, rotenonic acid, cafestol, precocene, methyl jasmonate, and abietic acid (FIG. 16E). Finally, esculetin inhibited CDCA-induced GGF-dependent activity by 54% just as this precocene analog repressed farnesol-induced activity in the assay using native FXR (data not shown). These results indicate that the ligand binding domains of FXR and EcR are required to mediate the transcriptional effects of JHs and insecticides.

Example 10

Site Directed Mutagenesis

Site-directed mutations were produced in each of the three EcR isoform vectors by changing one or two nucleotides in the codon corresponding to a specific amino acid position. Complementary primers carrying the mutational substitution were designed based on the actual EcR sequence in the region surrounding the site. Mutagenesis and subsequent transformation of Ultracompetent XL10-Gold E. coli proceeded according to the Quick Change II Site-directed Mutagenesis protocol (Stratagene). The transformants are cultured as described previously and plasmid DNA extracted by Qiagen midi-prep. Mutations were verified by sequencing, and the vector was further examined to ensure that no second site mutations had inadvertently been created during the procedure.

The mutations K497E, M504R, and A483T were created in all three EcR isoforms and their activity assayed in the cell culture system. Forward primers and their reverse complements were used according to manufacturer's protocols to carry out site-directed mutagenesis (Stratagene, QuikChange). The forward primer sequences were:

```
                                           (SEQ ID NO: 23)
K497E: 5' CAG ATC ACG TTA CTA GAG GCC TGC TCG TCG
       G 3';

(SEQ ID NO: 24)
M504R  5' CTC GTC GGA GGT GAG GAT GCT GCG TAT G 3';
and (SEQ ID NO: 25)
A483T  5'- G TTT GCT AAA GGT CTA CCA ACG TTT ACA
       AAG ATA CCC CAG G-3'.
```

Example 11

Electrophoretic Mobility Shift Assays (EMSAs)

Extracts transfected with the appropriate EcR and USP vectors described above were prepared according to the method described in Kitareewan et al., 1996. A double stranded hsp27 response element probe was constructed using the forward primer 5'AGCGACAAGGGTTCAATG-CACTTGT 3' (SEQ ID NO: 26) and the complementary reverse primer. The probe was end-labeled by fill-in reaction with the Klenow fragment and [α-$^{32}$P]-dCTP according to published protocols (Mouillet et al., 2001). After labeling, the oilgonucleotides were purified by centrifugation (Mini Quick Spin Columns, Roche Applied Sciences).

The binding reactions were prepared as reported previously (Mouillet et al., 2001). Protein extracts were added to the binding reactions after normalization by β-galactosidase reporter gene activity. The cell extract with the lowest β-galactosidase reporter gene activity was added at a maximum volume of 11 μl to the binding reaction. All other extracts were added proportionally based on relative β-galactosidase activity. MurA dissolved in ethanol was added to a final concentration of 10 μM with an equivalent volume of ethanol added to the control samples. Approximately 30,000 cpm of the radiolabeled hsp27 element was then added to the binding reaction and incubated with the extract for 20 min at room temperature. A 5% native polyacrylamide gel was used to separate the complexes.

Example 12

Western Blots

Cellular extracts corresponding to equal amounts of β-galactosidase activity were loaded onto lanes of a 15% polyacrylamide gel and subjected to electrophoresis (Biometra) at 15 mA. The gel was then electroblotted (MiniVE Blotter Module, Amersham Pharmacia Biotech) onto a nitrocellulose membrane (NC 45, 0.45 μm, Serva, Heidelberg) at 300 mA and 20V. The membrane was then soaked in blocking buffer (3% (w/v) milk powder, 1% (w/v) BSA, 20 mM Tris/HCl, 137 mM NaCl, 0.1% (v/v) Tween 20, pH 7.6). EcR was probed with the monoclonal IgG mouse antibody DDA2.7 diluted 1:1000 in blocking buffer; this antibody recognizes the D-domain shared by all three DmEcR isoforms. A peroxidase-conjugated secondary antibody (anti-mouse IgG, Sigma-Aldrich, Taufkirchen, Germany) was diluted 1:1000 (20 mM Tris/HCl, 137 mM NaCl, 0.1% (v/v) Tween 20, pH 7.6) to detect specific signals. The membrane was exposed to x-ray film (Hyperfilm, Amersham) and the image developed.

While the invention has been described and illustrated with reference to certain embodiments thereof, those skilled in the art will appreciate that various changes, modifications and substitutions can be made therein without departing from the spirit and scope of the invention. For example, effective dosages other than the dosages as set forth herein may be applicable as a consequence of variations in the responsiveness insect population being treated. Likewise, the specific biochemical responses observed may vary according to and depending on the particular active compound selected or whether there are present pharmaceutical carriers, as well as the type of formulation and mode of administration employed, and such expected variations or differences in the results are contemplated in accordance with the objects and practices of the present invention. All references referred to herein are incorporated by reference in their entireties.

That which is claimed is:

1. A method for the identification of species-specific and stage-specific insecticides having the ability to potentiate ecdysteroid-activated ecdysone receptor (EcR)-mediated transcription in a species-specific manner comprising the steps of:
   (a) transfecting a first mammalian cell population with a first vector comprising a nucleotide sequence that encodes an Ultraspiracle (USP) polypeptide from a first species, a second vector comprising a DNA sequence that encodes an EcR isoform polypeptide, and a reporter gene operably linked to a hormone responsive element (HRE);
   (b) transfecting a second mammalian cell population with a vector comprising a nucleotide sequence that encodes a USP polypeptide from a second species, a second vector comprising a DNA sequence that encodes for an EcR isoform polypeptide, and a reporter gene operably linked to a hormone responsive element (HRE);
   (c) adding to individual aliquots of each of the mammalian cell populations of (a) and (b) either: (i) various doses of an ecdysteroid, (ii) various doses of a compound to be tested for its ability to potentiate ecdysteroid-activated EcR-mediated transcription, or (iii) various doses of a combination of the ecdysteroid and the compound to be tested for its ability to potentiate ecdysteroid-activated EcR-mediated transcription;
   (d) measuring whether there is an increase in EcR-mediated transcription in the cells for each of the aliquots in step (c) when the compound to be tested for its ability to potentiate ecdysteroid-activated EcR-mediated transcription is added with the ecdysteroid, as compared to when only the ecdysteroid is added, or when only the compound to be tested for its ability to potentiate ecdysteroid-activated EcR-mediated transcription is added;
   (e) assessing the ability of the compound to be tested for its ability to potentiate ecdysteroid-activated EcR-mediated transcription to increase the ability of the ecdysteroid to increase EcR-mediated transcription at sub-maximal doses of the ecdysteroid up to, but not greater than the maximal response evoked by the ecdysteroid, such that a compound that increases ecdysteroid-activated EcR-mediated transcription at sub-maximal doses of the ecdysteroid but does not increase the maximal response evoked by the ecdysteroid, and does not increase EcR-mediated transcription when added alone, comprises a potentiator compound; and
   (f) comparing the ability of the compound to be tested for its ability to potentiate ecdysteroid-activated EcR-mediated transcription to potentiate ecdysteroid-activated EcR-mediated transcription of the reporter gene in the first mammalian cell population of (a) and the second mammalian cell population of (b).

2. The method of claim 1, wherein at least one of the first and second species comprise at least one of *Drosophila melanogaster, Leptinotarsa decemlineata, Chroristoneura fumerifana, Manduca sexta, Locusta migratoria, Heliothis virescens, Apis mellifera, Aedes aegypti,* or *Tenebrio molitor.*

3. The method of claim 1, wherein the DNA sequence that encodes the USP polypeptide comprises: (a) a mammalian nuclear receptor transactivation domain; and (b) a hinge region and a ligand binding domain of an insect USP protein.

4. The method of claim 3, wherein the DNA sequence that encodes the USP polypeptide further comprises a DNA binding domain of a USP protein.

5. The method of claim 1, wherein in step (a) the second vector comprises a DNA sequence that encodes for an Ecdysone receptor (EcR) isoform polypeptide from the first species and in step (b) the second vector comprises a DNA sequence that encodes for an Ecdysone receptor (EcR) isoform polypeptide from the second species.

6. The method of claim 1, wherein in step (a) the second vector comprises a DNA sequence that encodes a polypeptide comprising an Ecdysone receptor (EcR) isoform from the second species and in step (b) the second vector comprises a DNA sequence that encodes for a polypeptide comprising an Ecdysone receptor (EcR) isoform from the first species.

* * * * *